United States Patent
Lee et al.

(10) Patent No.: US 11,228,011 B2
(45) Date of Patent: *Jan. 18, 2022

(54) IONIC COMPOUND, COATING COMPOSITION COMPRISING SAME, AND ORGANIC LIGHT-EMITTING DIODE

(71) Applicant: LG Chem, Ltd., Seoul (KR)

(72) Inventors: Ho Gyu Lee, Daejeon (KR); Jaesoon Bae, Daejeon (KR); Seog Jae Seo, Daejeon (KR); Jaechol Lee, Daejeon (KR); Jiyeon Shin, Daejeon (KR); Leehyeon Baek, Daejeon (KR)

(73) Assignee: LG Chem, Ltd.

( * ) Notice: Subject to any disclaimer, the term of this patent is extended or adjusted under 35 U.S.C. 154(b) by 236 days.

This patent is subject to a terminal disclaimer.

(21) Appl. No.: 16/335,885

(22) PCT Filed: Nov. 24, 2017

(86) PCT No.: PCT/KR2017/013549
§ 371 (c)(1),
(2) Date: Mar. 22, 2019

(87) PCT Pub. No.: WO2018/097659
PCT Pub. Date: May 31, 2018

(65) Prior Publication Data
US 2020/0020858 A1   Jan. 16, 2020

(30) Foreign Application Priority Data

Nov. 25, 2016   (KR) .................. 10-2016-0158461

(51) Int. Cl.
*H01L 51/50* (2006.01)
*H01L 51/00* (2006.01)
(Continued)

(52) U.S. Cl.
CPC ............ *H01L 51/506* (2013.01); *C07C 25/02* (2013.01); *C07F 5/02* (2013.01); *C07F 5/027* (2013.01);
(Continued)

(58) Field of Classification Search
None
See application file for complete search history.

(56) References Cited

U.S. PATENT DOCUMENTS 6,465,385 B1    10/2002  Sivak et al.
2007/0020479 A1  1/2007  Uetani et al.
(Continued)

FOREIGN PATENT DOCUMENTS

CN    101185176 A    5/2008
CN    100486396 C    5/2009
(Continued)

OTHER PUBLICATIONS

International Search Report for PCT/KR2017/013549 dated Mar. 5, 2018.
(Continued)

*Primary Examiner* — Gregory D Clark
(74) *Attorney, Agent, or Firm* — Lerner, David, Littenberg, Krumholz & Mentlik, LLP

(57) ABSTRACT

The present disclosure relates to an ionic compound including an anion group of Chemical Formula 1, and a coating composition and an organic light emitting device including the same.

19 Claims, 6 Drawing Sheets

| 701 |
|-----|
| 601 |
| 501 |
| 401 |
| 301 |
| 201 |
| 101 |

(51) Int. Cl.

| | | |
|---|---|---|
| C08K 5/55 | (2006.01) | |
| C08K 5/36 | (2006.01) | |
| C08K 5/56 | (2006.01) | |
| C07F 5/02 | (2006.01) | |
| C09D 7/63 | (2018.01) | |
| C07C 25/02 | (2006.01) | |
| C09D 5/24 | (2006.01) | |
| C08K 5/03 | (2006.01) | |

(52) U.S. Cl.
CPC .................. *C08K 5/36* (2013.01); *C08K 5/55* (2013.01); *C08K 5/56* (2013.01); *C09D 5/24* (2013.01); *C09D 7/63* (2018.01); *H01L 51/005* (2013.01); *H01L 51/008* (2013.01); *H01L 51/0026* (2013.01); *H01L 51/0059* (2013.01); *H01L 51/0061* (2013.01); *H01L 51/0065* (2013.01); *H01L 51/0068* (2013.01); *H01L 51/0072* (2013.01); *H01L 51/0074* (2013.01); *H01L 51/5056* (2013.01); *H01L 51/5088* (2013.01); *H01L 51/5092* (2013.01); *C08K 5/03* (2013.01); *H01L 51/0003* (2013.01); *H01L 2251/552* (2013.01)

(56) References Cited

U.S. PATENT DOCUMENTS

| | | | |
|---|---|---|---|
| 2009/0134779 | A1 | 5/2009 | Kawami et al. |
| 2010/0109000 | A1 | 5/2010 | Mathai et al. |
| 2010/0243992 | A1 | 9/2010 | Tsuji et al. |
| 2011/0089411 | A1 | 4/2011 | Xia et al. |
| 2011/0227047 | A1 | 9/2011 | Wen et al. |
| 2012/0001127 | A1 | 1/2012 | Brown et al. |
| 2012/0037894 | A1 | 2/2012 | Okabe |
| 2012/0074360 | A1 | 3/2012 | Funyuu et al. |
| 2014/0205951 | A1 | 7/2014 | Ogihara et al. |
| 2014/0291584 | A1 | 10/2014 | Badre et al. |
| 2015/0179963 | A1 | 6/2015 | Bando et al. |
| 2016/0020395 | A1 | 1/2016 | Funyuu et al. |
| 2017/0299493 | A1 | 10/2017 | Norton |
| 2019/0019956 | A1 * | 1/2019 | Gorohmaru ......... H01L 51/0059 |
| 2019/0280206 | A1 | 9/2019 | Lee et al. |

FOREIGN PATENT DOCUMENTS

| | | | |
|---|---|---|---|
| CN | 102077381 | A | 5/2011 |
| CN | 102449799 | A | 5/2012 |
| CN | 102959009 | A | 3/2013 |
| CN | 103865220 | A | 6/2014 |
| CN | 104365180 | A | 2/2015 |
| CN | 104604332 | A | 5/2015 |
| CN | 108884114 | A | 11/2018 |
| EP | 0710663 | A1 | 5/1996 |
| EP | 1725079 | A1 | 11/2006 |
| EP | 3434682 | A1 | 1/2019 |
| JP | H08127611 | A | 5/1996 |
| JP | H08143617 | A | 6/1996 |
| JP | 11286491 | * | 10/1999 |
| JP | H11286491 | A | 10/1999 |
| JP | 2000178281 | A | 6/2000 |
| JP | 2008063329 | A | 3/2008 |
| JP | 2009196982 | A | 9/2009 |
| JP | 2011525918 | A | 9/2011 |
| JP | 2012507151 | A | 3/2012 |
| JP | 4991648 | B2 | 8/2012 |
| JP | 2014122330 | A | 7/2014 |
| JP | 2014141585 | A | 8/2014 |
| JP | 2016060764 | A | 4/2016 |
| JP | 2019516959 | A | 6/2019 |
| JP | 2019520122 | A | 7/2019 |
| JP | 2019537835 | A | 12/2019 |
| JP | 2020500421 | A | 1/2020 |
| KR | 20110037972 | A | 4/2011 |
| KR | 20110134399 | A | 12/2011 |
| KR | 20140023246 | A | 2/2014 |
| KR | 20140063462 | A | 5/2014 |
| KR | 101422454 | B1 | 7/2014 |
| KR | 20150127077 | A | 11/2015 |
| KR | 20160041124 | A | 4/2016 |
| KR | 20160117284 | A | 10/2016 |
| WO | 2005089024 | A1 | 9/2005 |
| WO | 2009158069 | A1 | 12/2009 |
| WO | 2010104184 | A1 | 9/2010 |
| WO | 2014075298 | A1 | 5/2014 |
| WO | 2017164268 | A1 | 9/2017 |
| WO | 2017207327 | A1 | 12/2017 |

OTHER PUBLICATIONS

International Search Report for PCT/KR2017/013554 dated Mar. 5, 2018.
International Search Report for PCT/KR2017/013558 dated Feb. 19, 2018.
International Search Report for PCT/KR2017/013559 dated Feb. 19, 2018.
Türp et al., "Synthesis of Nanometer-Sized, Rigid, and Hydrophobic Anions," Angewandte Chemie, International Ed., May 16, 2011, 123 (21), pp. 4962-4965.
Extended European Search Report including the Search Opinion for Application No. 17872963.8 dated Oct. 24, 2019, 8 pages.
Extended European Search Report including the Search Opinion for Application No. 17874454.6 dated Oct. 10, 2019, 8 pages.
Extended European Search Report including the Search Opinion for Application No. 17874046.0 dated Sep. 23, 2019, 8 pages.
Search Report from Office Action for Chinese Appiation No. 2017800630440 dated May 8, 2021; 4 pages.
Search Report from Office Action for Chinese Application No. 201780072188.2 dated May 8, 2021; 4 pages.

* cited by examiner

[FIG. 1]

| |
|---|
| 701 |
| 601 |
| 501 |
| 401 |
| 301 |
| 201 |
| 101 |

[FIG. 2]
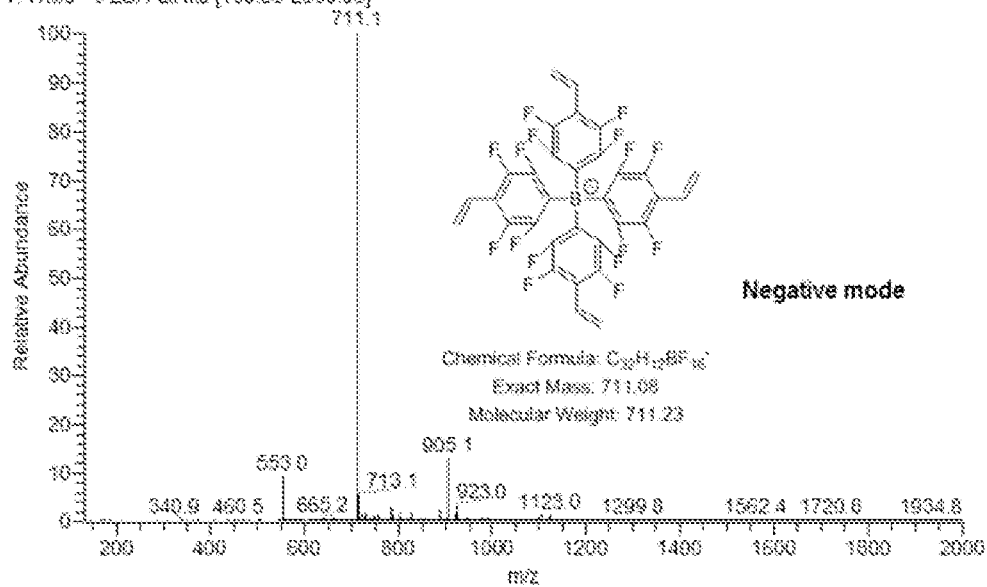
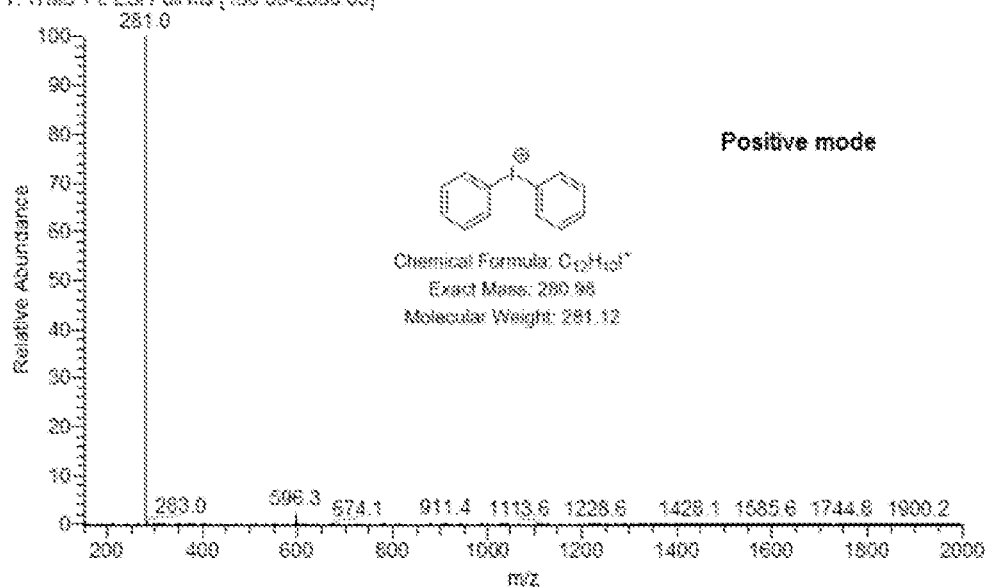

【FIG. 3】
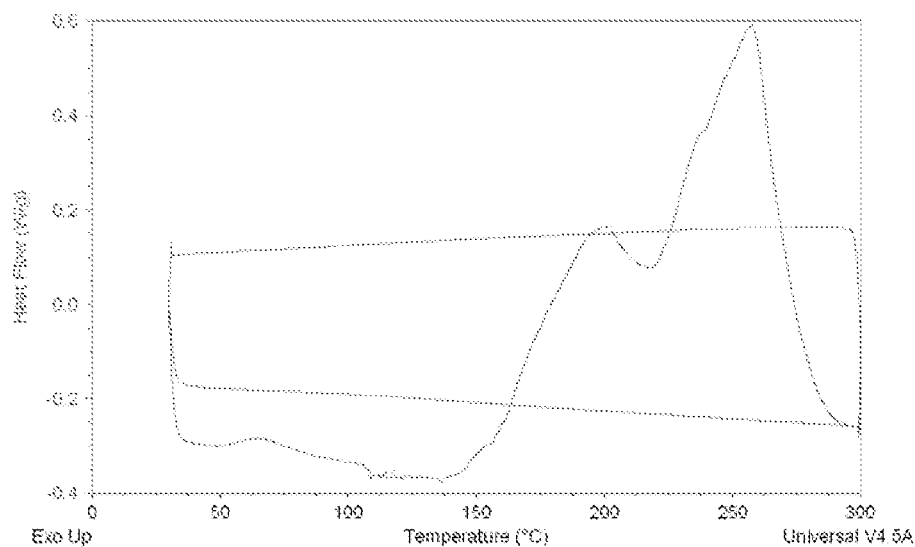
【FIG. 4】
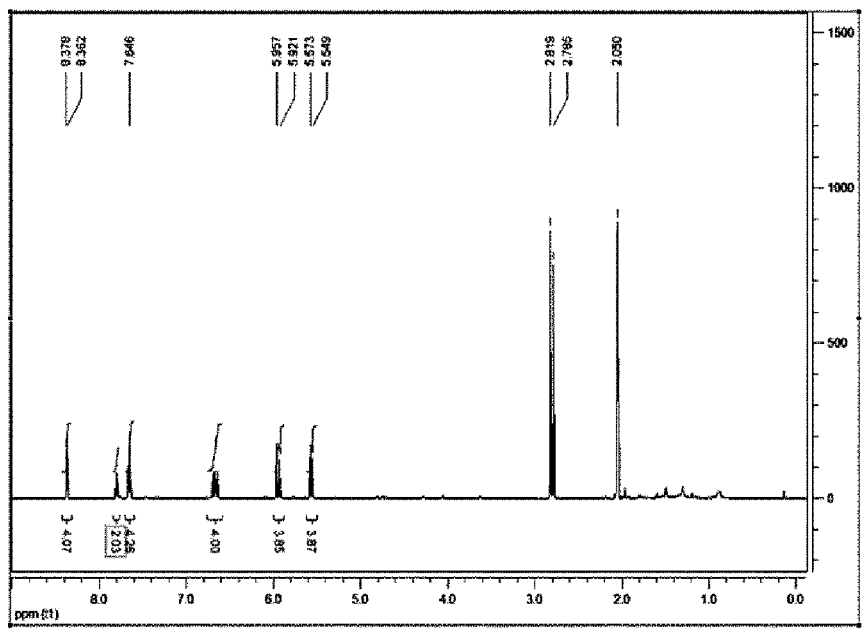

[FIG. 5]
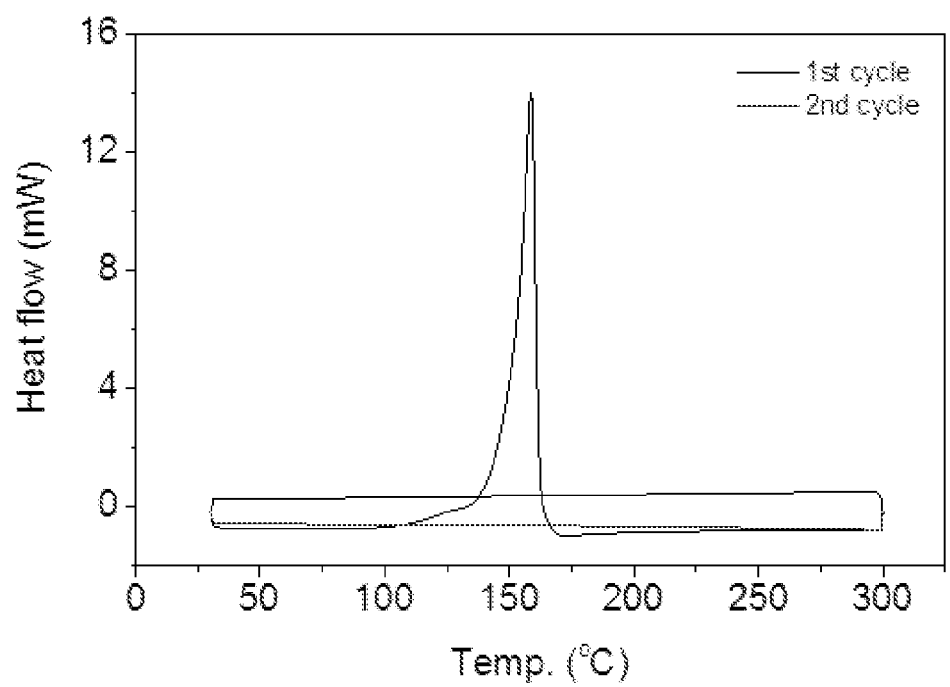
[FIG. 6]
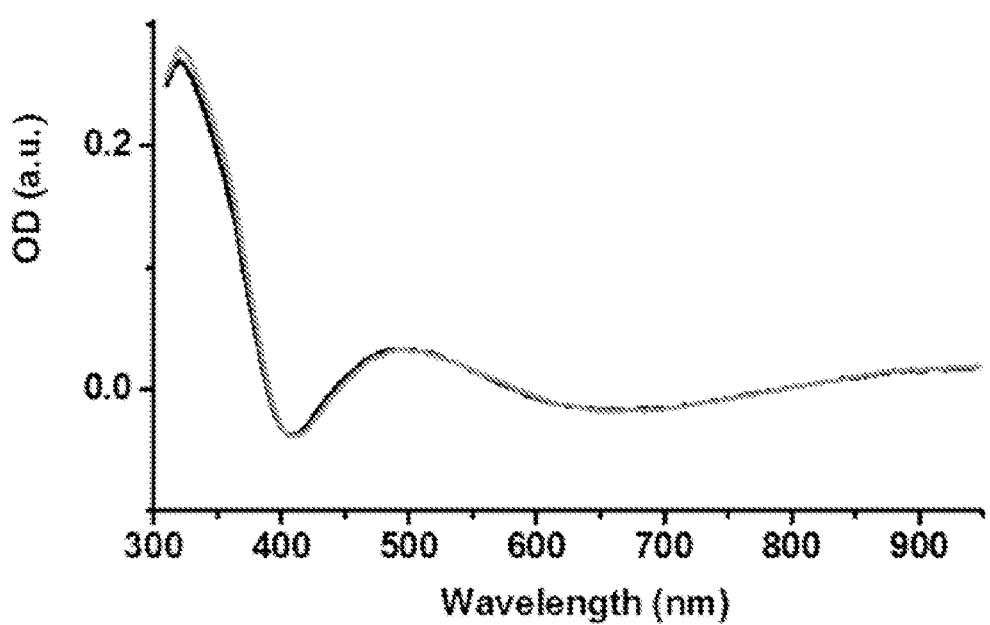

[FIG. 7]
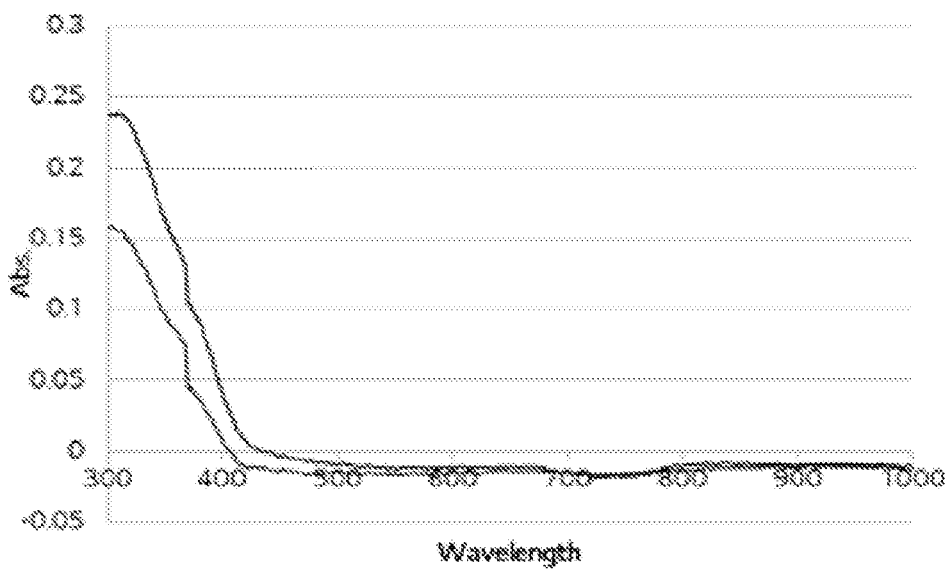
[FIG. 8]
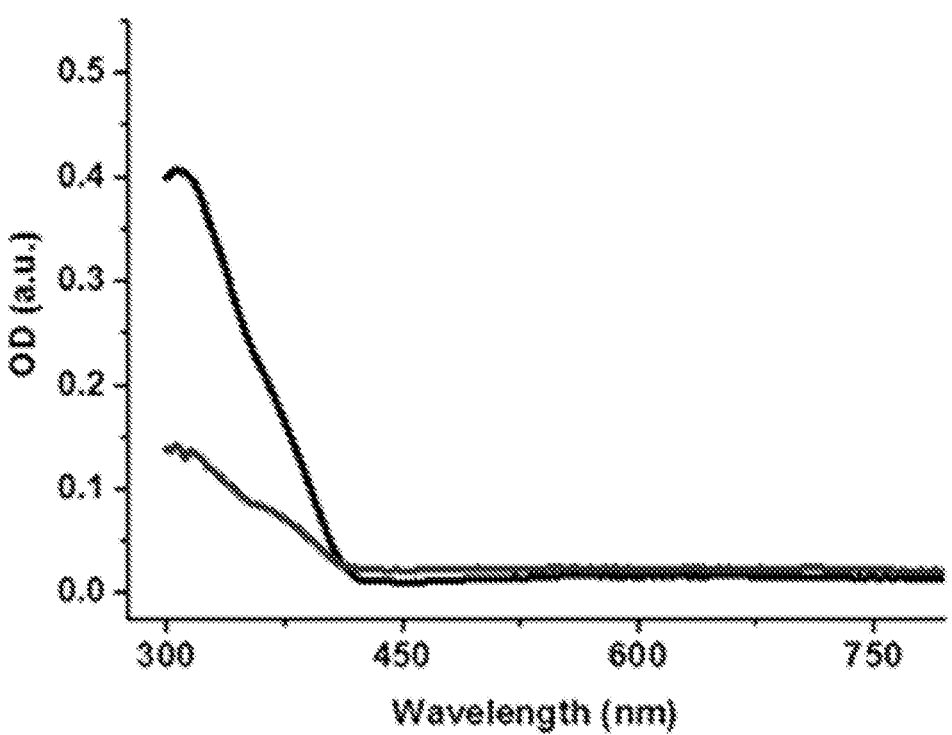

[FIG. 9]
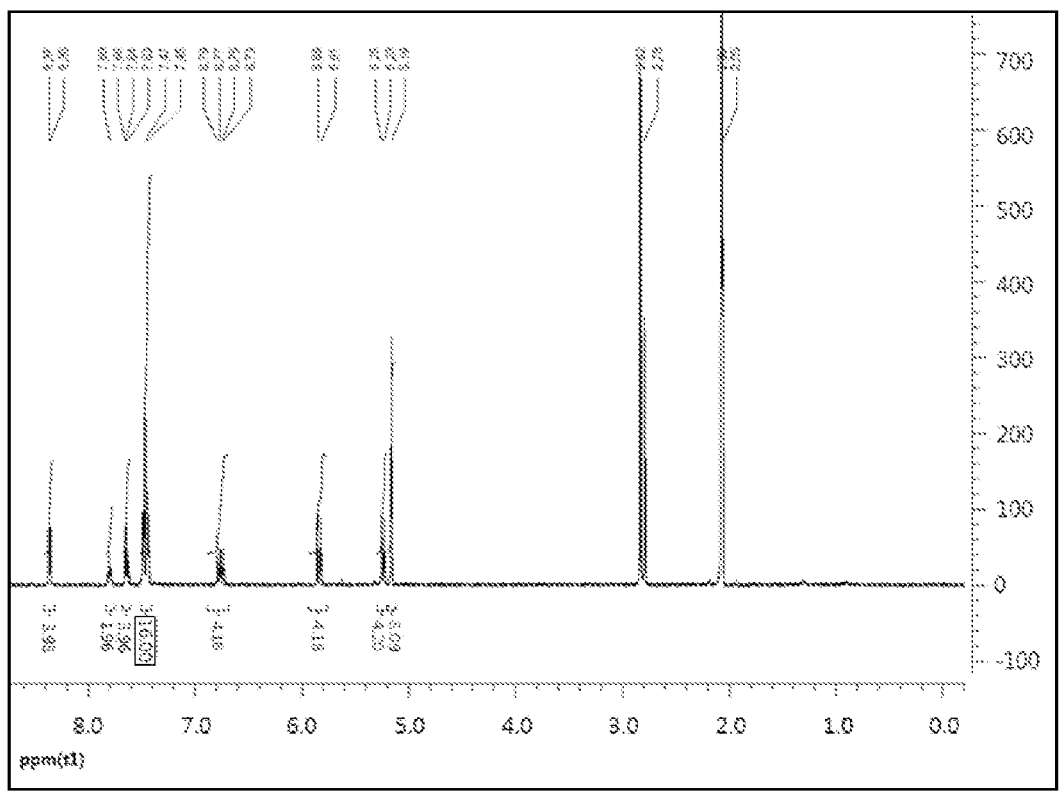

IONIC COMPOUND, COATING COMPOSITION COMPRISING SAME, AND ORGANIC LIGHT-EMITTING DIODE

CROSS-REFERENCE TO RELATED APPLICATIONS

The present application is a national phase entry under 35 U.S.C. § 371 of International Application No. PCT/KR2017/013549 filed Nov. 24, 2017, which claims priority from Korean Patent Application No. 10-2016-0158461 filed Nov. 25, 2016, all of which are incorporated herein by reference in their entirety.

TECHNICAL FIELD

The present specification relates to an ionic compound, and a coating composition and an organic light emitting device including the same.

BACKGROUND ART

An organic light emission phenomenon is one of examples converting a current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic light emitting device using such a principle may be generally formed with a cathode, an anode, and an organic material layer placed therebetween, for example, an organic material layer including a hole injection layer, a hole transfer layer, a light emitting layer and an electron transfer layer.

Materials used in an organic light emitting device are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting layer material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferred that materials used in an organic light emitting device additionally have properties as follows.

First, materials used in an organic light emitting device preferably have excellent thermal stability. This is due to joule heating produced by charge migration in the organic light emitting device. NPB normally used as a hole transfer layer material currently has a glass transition temperature of 100° C. or lower, and has a problem in that it is difficult to use in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a HOMO or LUMO energy level. PEDOT:PSS currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifetime.

In addition thereto, materials used in an organic light emitting device need to have excellent chemical stability, charge mobility, and interface property with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials also need to improve an interface with electrodes including metals or metal oxides.

Accordingly, development of organic materials fulfilling such requirements has been required in the art.

DISCLOSURE

Technical Problem

The present specification is directed to providing an ionic compound, and a coating composition and an organic light emitting device including the same.

Technical Solution

One embodiment of the present specification provides an ionic compound including an anion group represented by the following Chemical Formula 1.

[Chemical Formula 1]

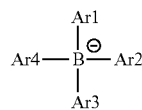

In Chemical Formula 1,

Ar1 to Ar4 are the same as or different from each other, at least one of Ar1 to Ar4 is represented by the following Chemical Formula 2, and the remaining Ar1 to Ar4 are represented by the following Chemical Formula 3,

[Chemical Formula 2]

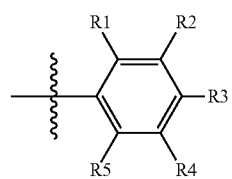

in Chemical Formula 2, at least one of R1 to R5 is F, a cyano group, or a substituted or unsubstituted fluoroalkyl group, at least one of the remaining R1 to R5 is a curing group, the remaining R1 to R5 are the same as or different from each other, and each independently hydrogen; deuterium; a nitro group; —C(O)$R_{100}$; —O$R_{101}$; —S$R_{102}$; —$SO_3R_{103}$; —COO$R_{104}$; —OC(O)$R_{105}$; —C(O)N$R_{106}R_{107}$; a substituted or unsubstituted alkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, $R_{100}$ to $R_{107}$ are the same as or different from each other, and each independently hydrogen; deuterium; or a substituted or unsubstituted alkyl group,

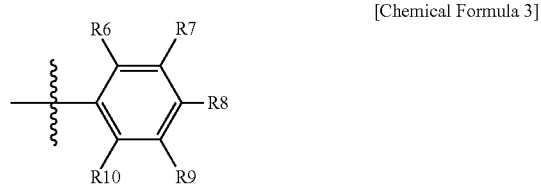

[Chemical Formula 3]

in Chemical Formula 3, at least one of R6 to R10 is a curing group, the remaining R6 to R10 are the same as or different from each other, and each independently hydrogen; deuterium; a nitro group; —C(O)$R_{100}$; —O$R_{101}$; —S$R_{102}$; —$SO_3R_{103}$; —COO$R_{104}$; —OC(O)$R_{105}$; —C(O)N$R_{106}R_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, and $R_{100}$ to $R_{107}$ are the same as or different from each other, and each independently hydrogen; deuterium; or a substituted or unsubstituted alkyl group.

Another embodiment of the present specification provides a coating composition including the ionic compound described above.

Still another embodiment of the present specification provides an organic light emitting device including a first electrode; a second electrode; and one or more organic material layers provided between the first electrode and the second electrode, wherein one or more layers of the organic material layers include a cured material of the coating composition described above.

Advantageous Effects

A compound according to one embodiment of the present specification includes a functional group polymerized by heat or light, and when providing sufficient heat or light after forming a film, tolerance to a solvent for a process is developed, and properties of the film do not change since washing off of the compound according to one embodiment of the present specification or migration of interlayer materials is prevented, and as a result, an organic light emitting device having reproducibility can be manufactured.

The compound according to one embodiment of the present specification is an ionic monomer and dissolved in a solvent coated through a solution process, and then formed to a film through heat treatment or UV treatment, and particularly, the compound according to the present specification can provide a low driving voltage, high light emission efficiency and a high lifetime property when cured at around 200° C.

DESCRIPTION OF DRAWINGS

FIG. 1 illustrates an example of an organic light emitting device according to one embodiment of the present specification.

FIG. 2 shows MS data of Compound 4 according to one embodiment of the present specification.

FIG. 3 shows DSC data of Compound 4 according to one embodiment of the present specification.

FIG. 4 is an NMR spectrum of Compound 4 according to one embodiment of the present specification.

FIG. 5 shows DSC data of Comparative Compound 1 according to one embodiment of the present specification Comparative.

FIG. 6 shows film retention rate data of Coating Composition 4 according to one embodiment of the present specification.

FIG. 7 shows film retention rate data of Coating Composition 8 according to one embodiment of the present specification.

FIG. 8 shows film retention rate data of Coating Composition 9 according to one embodiment of the present specification.

FIG. 9 is an NMR spectrum of Compound 5 according to one embodiment of the present specification.

REFERENCE NUMERAL

101: Substrate
201: Anode
301: Hole Injection Layer
401: Hole Transfer Layer
501: Light Emitting Layer
601: Electron Transfer Layer
701: Cathode

MODE FOR DISCLOSURE

Hereinafter, the present specification will be described in more detail.

In the present specification, a description of a certain member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

Throughout the specification of the present application, the term "combination thereof" included in a Markush-type expression means a mixture or a combination of one or more selected from the group consisting of constituents described in the Markush-type expression, and means including one or more selected from the group consisting of the constituents.

One embodiment of the present specification provides a coating composition including an ionic compound including an anion group represented by Chemical Formula 1.

In one embodiment of the present specification, the coating composition is for coating an organic material layer of an organic light emitting device.

In one embodiment of the present specification, compounds having solubility for proper organic solvents are preferred as the ionic compound including the anion group represented by Chemical Formula 1.

In the present specification, a "curing group" may mean a reactive substituent crosslinking compounds by being exposed to heat and/or light. The crosslinking may be produced while linking radicals produced by decomposing carbon-carbon multiple bonds or cyclic structures through heat treatment or light irradiation.

In one embodiment of the present specification, the curing group is selected from a group of the following curing groups.

[Group of Curing Groups]

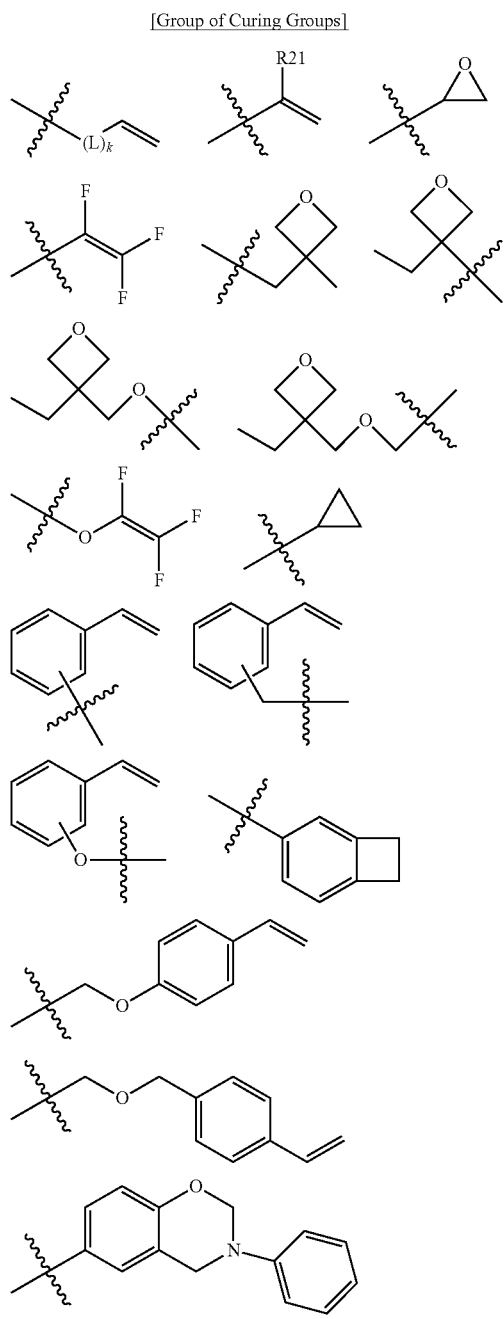

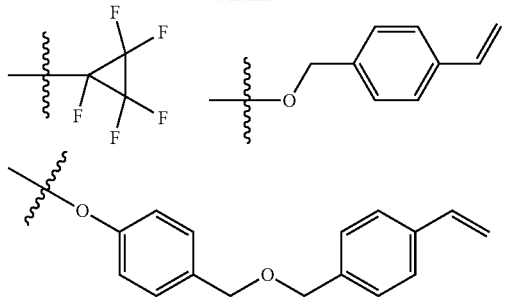

In the group of the curing groups, L is a direct bond; O; S; a substituted or unsubstituted alkylene group; a substituted or unsubstituted arylene group; or a substituted or unsubstituted divalent heterocyclic group, k is an integer of 1 or 2, and when k is 2, substituents in the parentheses are the same as or different from each other, and R21 is a substituted or unsubstituted alkyl group.

In one embodiment of the present specification, various curing groups may be used as the curing group as long as it is a curing group capable of curing, and the curing group is not limited to the group of the curing groups.

In the present specification, an onium compound means a compound produced through hydrogen ions or other organic radicals coordinate bonding to an unshared electron pair such as oxygen, sulfur, nitrogen or phosphorus.

Hereinafter, substituents of the present specification will be described below in detail, however, the substituents are not limited thereto.

In the present specification,

means a site bonding to other substituents or bonding sites.

The term "substitution" in the present specification means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one or more substituents selected from the group consisting of hydrogen; deuterium; a halogen group; an alkyl group; a cycloalkyl group; an alkoxy group; an aryloxy group; an aryl group; an amine group; an arylamine group; and a curing group, or being unsubstituted, or being substituted with a substituent linking two or more substituents among the substituents illustrated above, or being unsubstituted.

In the present specification, examples of the halogen group may include fluorine, chlorine, bromine or iodine.

In the present specification, the alkyl group may be linear, branched or cyclic, and although not particularly limited thereto, the number of carbon atoms is preferably from 1 to 50. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenxyloxy and the like, but are not limited thereto.

The alkyl group may be substituted with an aryl group or a heterocyclic group to function as an arylalkyl group or a heteroarylalkyl group. The aryl group and the heterocyclic group may be selected from among examples of an aryl group or a heterocyclic group to describe below.

In the present specification, the length of the alkyl group does not affect a conjugation length of the compound, and may affect the use of the compound in an organic light emitting device, for example, the use of a vacuum deposition method or a solution coating method.

In the present specification, the cycloalkyl group is not particularly limited, but preferably has 3 to 60 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

When the aryl group is a monocyclic aryl group in the present specification, the number of carbon atoms is not particularly limited, but is preferably from 6 to 25. Specific examples of the monocyclic aryl group may include a phenyl group, a biphenyl group, a terphenyl group, a quaterphenyl group and the like, but are not limited thereto.

When the aryl group is a multicyclic aryl group, the number of carbon atoms is not particularly limited, but is preferably from 10 to 30. Specific examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

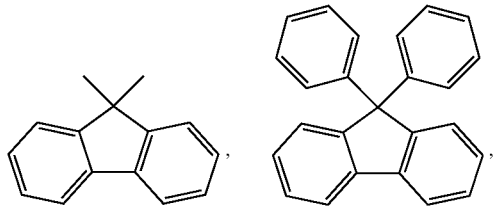

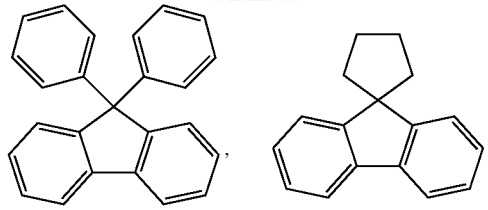

and the like may be included. However, the structure is not limited thereto.

The aryl group may be substituted with an alkyl group or an alkoxy group to function as an arylalkyl group or an aryloxy group. The alkyl group or the alkoxy group may be selected from among the examples described above.

In the present specification, the number of carbon atoms of the amine group is not particularly limited, but is preferably from 1 to 30. The amine group may be substituted with the above-described alkyl group, aryl group, heterocyclic group, alkenyl group, cycloalkyl group, combinations thereof, and the like, and specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups. For example, the aryl group in the arylamine group may be selected from among the examples of the aryl group described above. Specific examples of the arylamine group may include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, the heterocyclic group includes one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heteroaryl group may be monocyclic or multicyclic. Examples of the heterocyclic group may include a thiophene group, a furanyl group, a pyrrole group, an imidazolyl group, a triazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, a dibenzofuranyl group and the like, but are not limited thereto.

In the present specification, the divalent heterocyclic group means the heterocyclic group having two bonding sites, that is, a divalent group. Descriptions on the heterocyclic group provided above may be applied thereto except for each being a divalent.

In the present specification, the arylene group means the aryl group having two bonding sites, that is, a divalent group. Descriptions on the aryl group provided above may be applied thereto except for each being a divalent.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the ring formed by adjacent groups bonding to each other may be monocyclic or multicyclic, may be aliphatic, aromatic, or a fused ring of aliphatic or aromatic, and may form a hydrocarbon ring or a heteroring.

In one embodiment of the present specification, when the anion group represented by Chemical Formula 1 does not have a curing group, curing does not occur, and device properties may decline due to migration of a cation group and an anion group of the present specification between electrode layers. In addition, as the number of the curing group increases, a coating composition curing rate increases and a film retention rate is enhanced.

In one embodiment of the present specification, Ar1 is represented by Chemical Formula 2, and Ar2 to Ar4 are represented by Chemical Formula 3.

In one embodiment of the present specification, Ar1 and Ar2 are represented by Chemical Formula 2, and Ar3 and Ar4 are represented by Chemical Formula 3.

In one embodiment of the present specification, Ar1 to Ar3 are represented by Chemical Formula 2, and Ar4 is represented by Chemical Formula 3.

In one embodiment of the present specification, Ar1 to Ar4 are represented by Chemical Formula 2. Particularly, when Ar1 to Ar4 are all Chemical Formula 2 and when a proportion of the F, the cyano group or the fluoroalkyl group increases, a film retention rate is enhanced when heat treating.

In one embodiment of the present specification, the ionic compound including the anion group may be used in a hole injection layer of an organic light emitting device, and, when used in the hole injection layer, may be used as a dopant. Herein, when the F content of the anion group increases, an electron attracting force from other compounds (host compound) increases, and holes are more favorably formed in the host resulting in performance enhancement in the hole injection layer.

In one embodiment of the present specification, the F content may be analyzed using a COSA AQF-100 combustion furnace coupled to a Dionex ICS 2000 ion-chromatograph, or may be identified through 19F NMR, a method generally used for F analysis.

In one embodiment of the present specification, Chemical Formula 2 is represented by any one of the following Chemical Formulae 2-1 to 2-10.

[Chemical Formula 2-1]

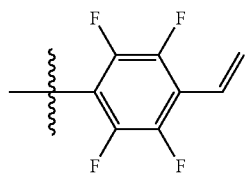

[Chemical Formula 2-2]

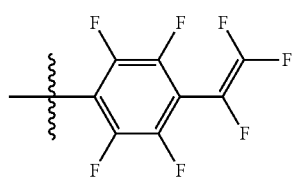

[Chemical Formula 2-3]

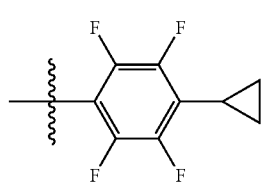

[Chemical Formula 2-4]

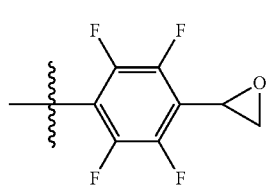

[Chemical Formula 2-5]

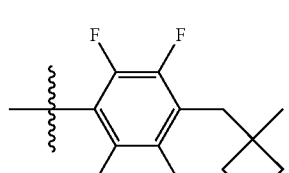

[Chemical Formula 2-6]

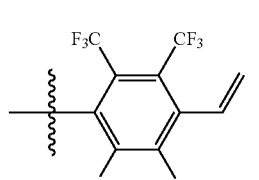

[Chemical Formula 2-7]

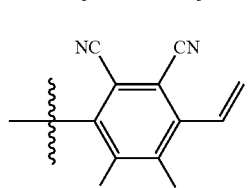

[Chemical Formula 2-8]

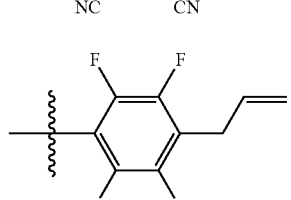

[Chemical Formula 2-9]

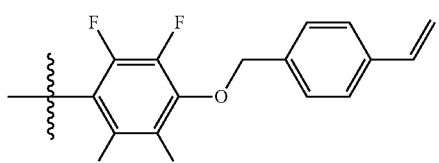

[Chemical Formula 2-10]

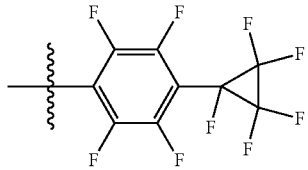

In one embodiment of the present specification, Chemical Formula 3 is represented by any one of the following Chemical Formulae 3-1 to 3-8.

[Chemical Formula 3-1]

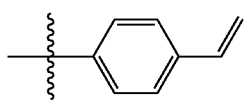

[Chemical Formula 3-2]

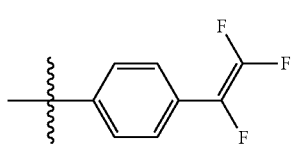

[Chemical Formula 3-3]

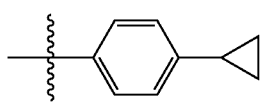

[Chemical Formula 3-4]

[Chemical Formula 3-5]

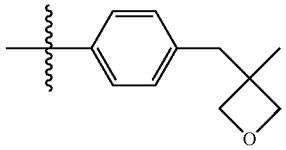

[Chemical Formula 3-6]

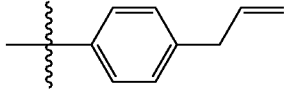

[Chemical Formula 3-7]

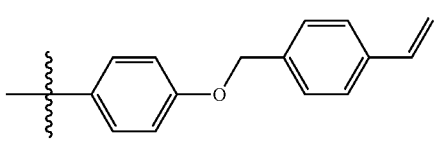

[Chemical Formula 3-8]

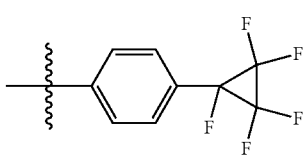

In one embodiment of the present specification, the anion group of Chemical Formula 1 is any one selected from among the following structural formulae.

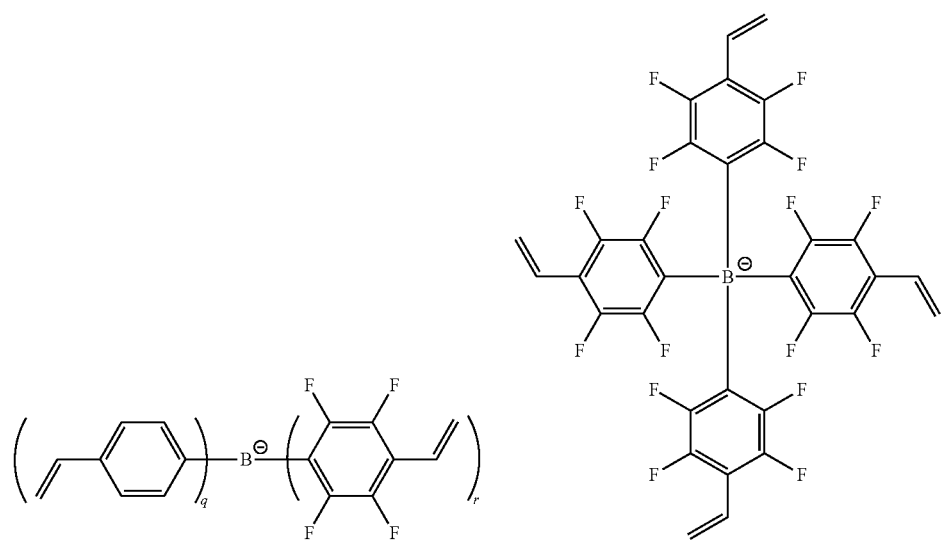

-continued
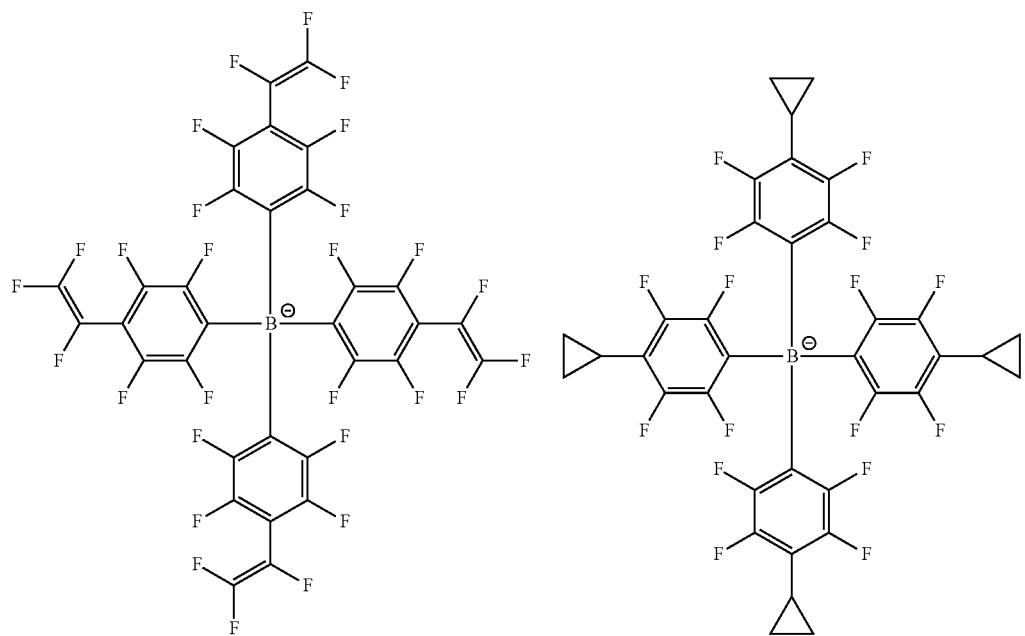
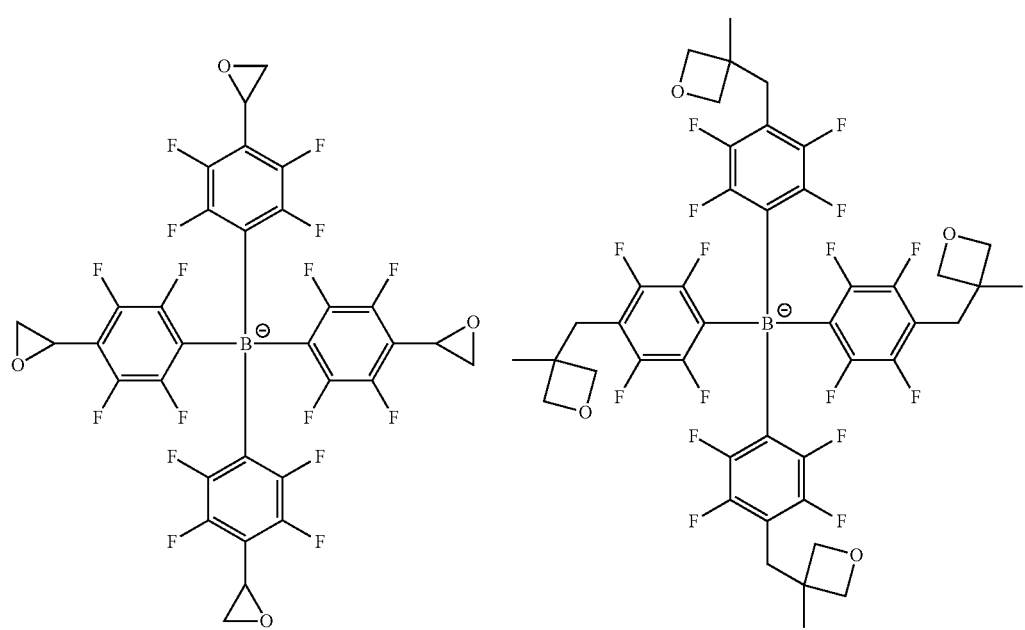

-continued
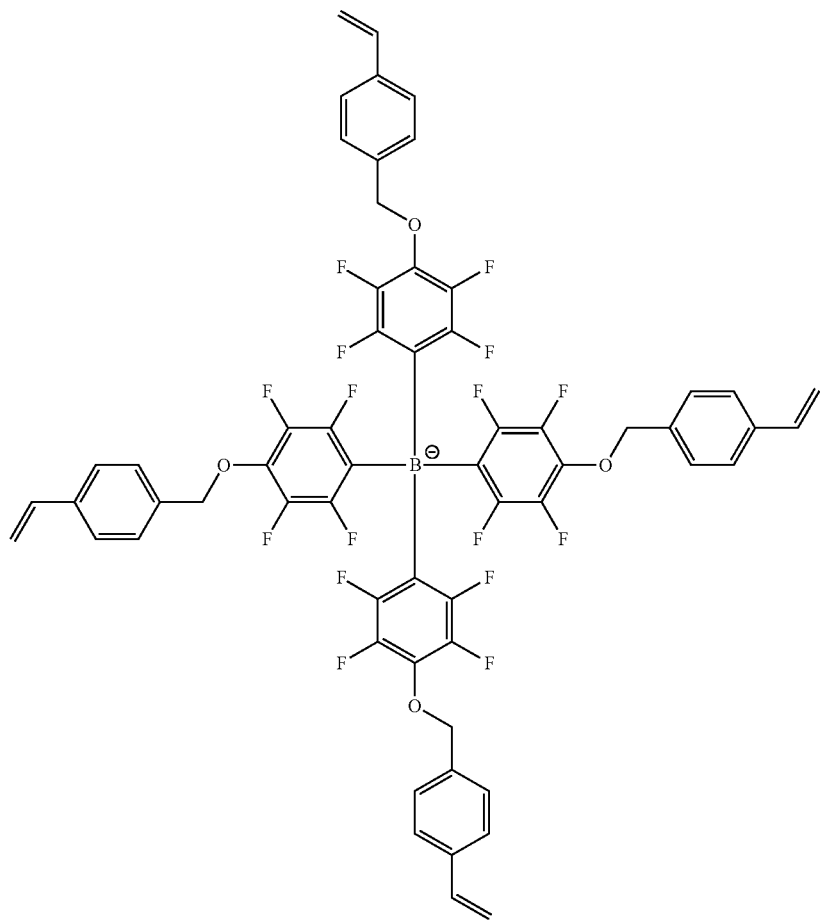
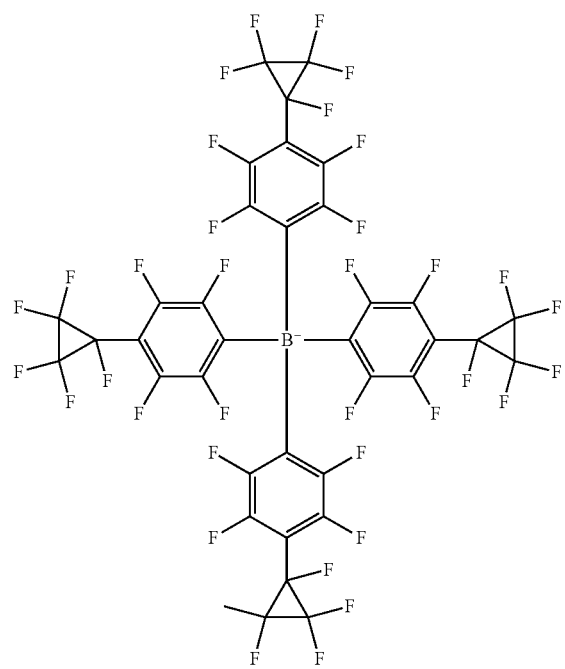

In the structural formulae, r is an integer of 1 to 4, q is an integer of 0 to 3, and q+r=4.

In one embodiment of the present specification, the ionic compound includes a cation group, and the cation group is selected from among monovalent cation groups, onium compounds or the following structural formulae.

In one embodiment of the present specification, the monovalent cation group may be an alkali-metal cation, and the alkali-metal cation may include $Na^+$, $Li^+$, $K^+$ and the like, but is not limited thereto.

In one embodiment of the present specification, the ionic compound includes a cation group, and the cation group is selected from among onium compounds or the following structural formulae.

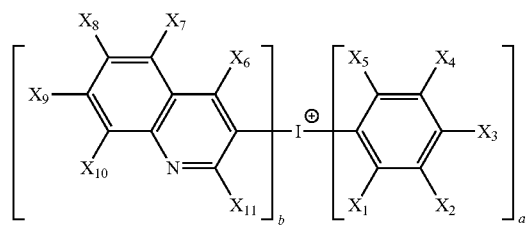

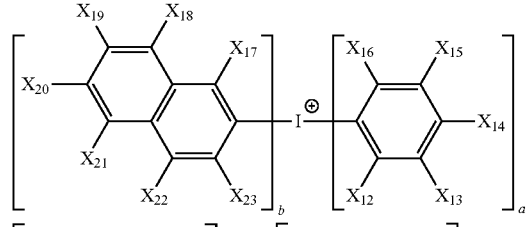

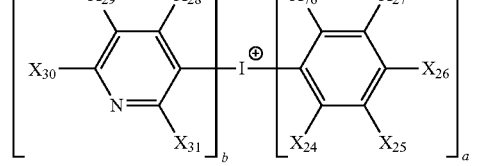

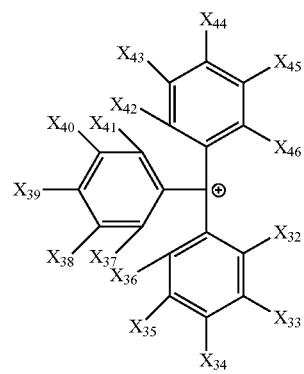

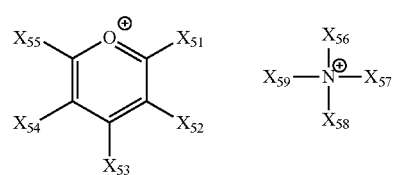

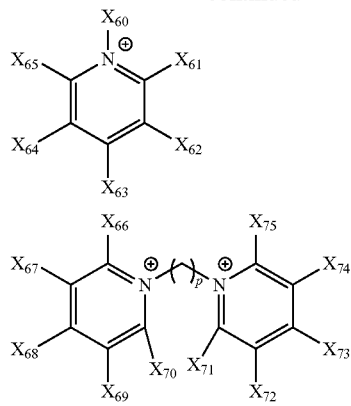

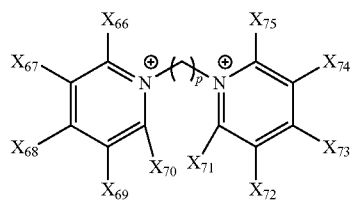

In the structural formulae, $X_1$ to $X_{76}$ are the same as or different from each other, and each independently hydrogen; a cyano group; a nitro group; a halogen group; $-COOR_{104}$; a substituted or unsubstituted alkyl group; a substituted or unsubstituted alkoxy group; a substituted or unsubstituted cycloalkyl group; a substituted or unsubstituted fluoroalkyl group; or a substituted or unsubstituted aryl group, or a curing group selected from the group of the curing groups, $R_{104}$ is hydrogen; deuterium; or a substituted or unsubstituted alkyl group, p is an integer of 0 to 10, and a is 1 or 2, b is 0 or 1, and a+b=2.

In one embodiment of the present specification, the cation group is represented by any one of the following Chemical Formula 10 to Chemical Formula 15.

[Chemical Formula 10]

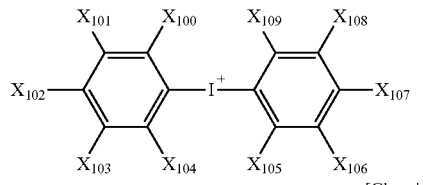

[Chemical Formula 11]

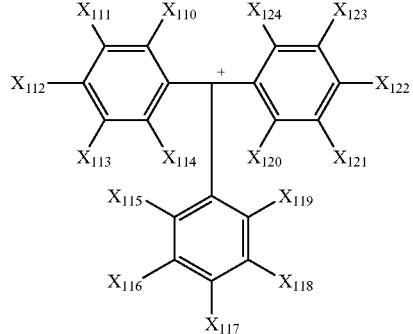

[Chemical Formula 12]

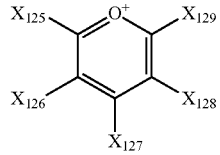

[Chemical Formula 13]

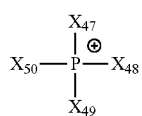

[Chemical Formula 14]

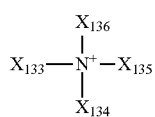

[Chemical Formula 15]

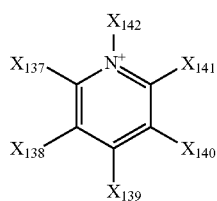

$X_{100}$ to $X_{142}$ are the same as or different from each other, and each independently hydrogen; a cyano group; a nitro group; a halogen group; —$COOR_{104}$; a substituted or unsubstituted alkyl group; a substituted or unsubstituted alkoxy group; a substituted or unsubstituted cycloalkyl group; a substituted or unsubstituted fluoroalkyl group; or a substituted or unsubstituted aryl group, or a curing group selected from the group of the curing groups, and $R_{104}$ is a substituted or unsubstituted alkyl group.

In one embodiment of the present specification, the cation group is any one selected from among the following structural formulae.

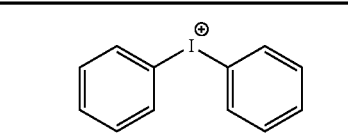
1-1

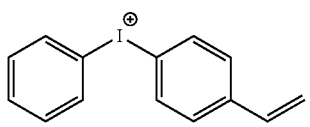
1-2

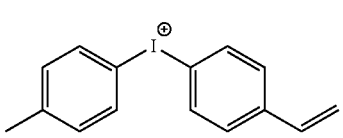 [SMILES: C=Cc1ccc([I+]c2ccc(C)cc2)cc1]
1-3

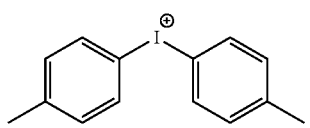
1-4

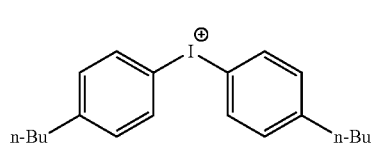
1-5

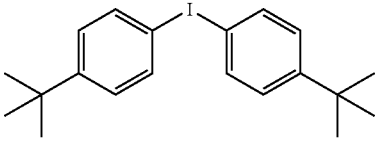
1-6

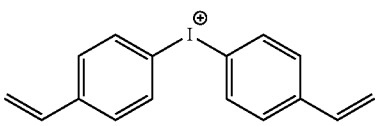 [SMILES: C=Cc1ccc([I+]c2ccc(C=C)cc2)cc1]
1-7

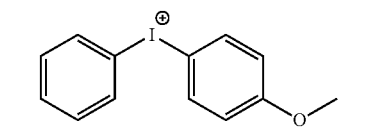
1-8

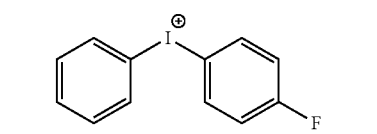 [SMILES: Fc1ccc([I+]c2ccccc2)cc1]
1-9

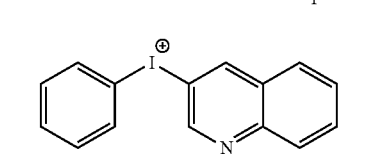
1-10

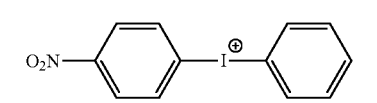
1-11

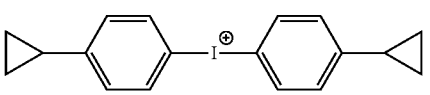 [SMILES: c1cc(C2CC2)ccc1[I+]c1ccc(C2CC2)cc1]
1-12

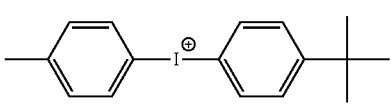
1-13

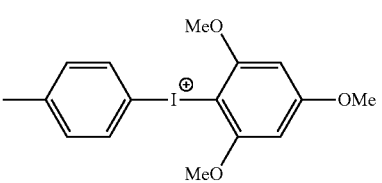 [SMILES: COc1cc(OC)c([I+]c2ccc(C)cc2)c(OC)c1]
1-14

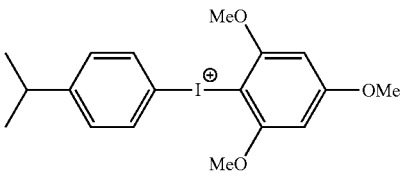 [SMILES: COc1cc(OC)c([I+]c2ccc(C(C)C)cc2)c(OC)c1]
1-15

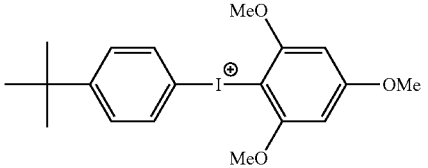 [SMILES: COc1cc(OC)c([I+]c2ccc(C(C)(C)C)cc2)c(OC)c1]
1-16

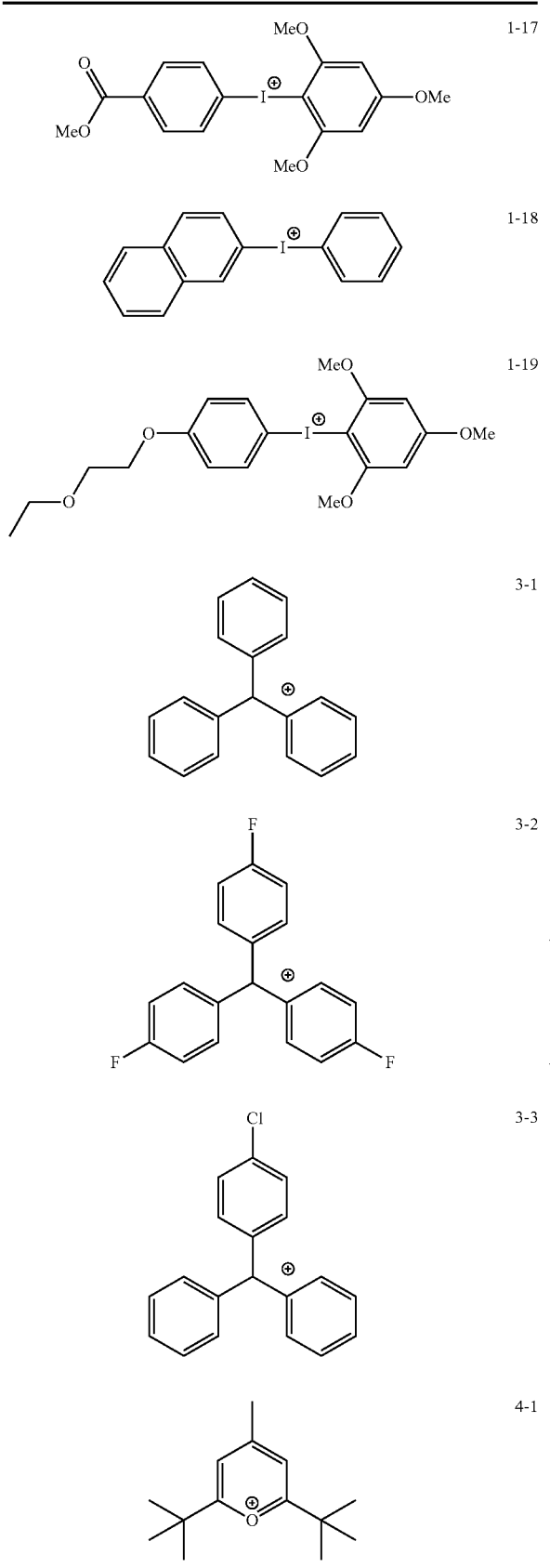
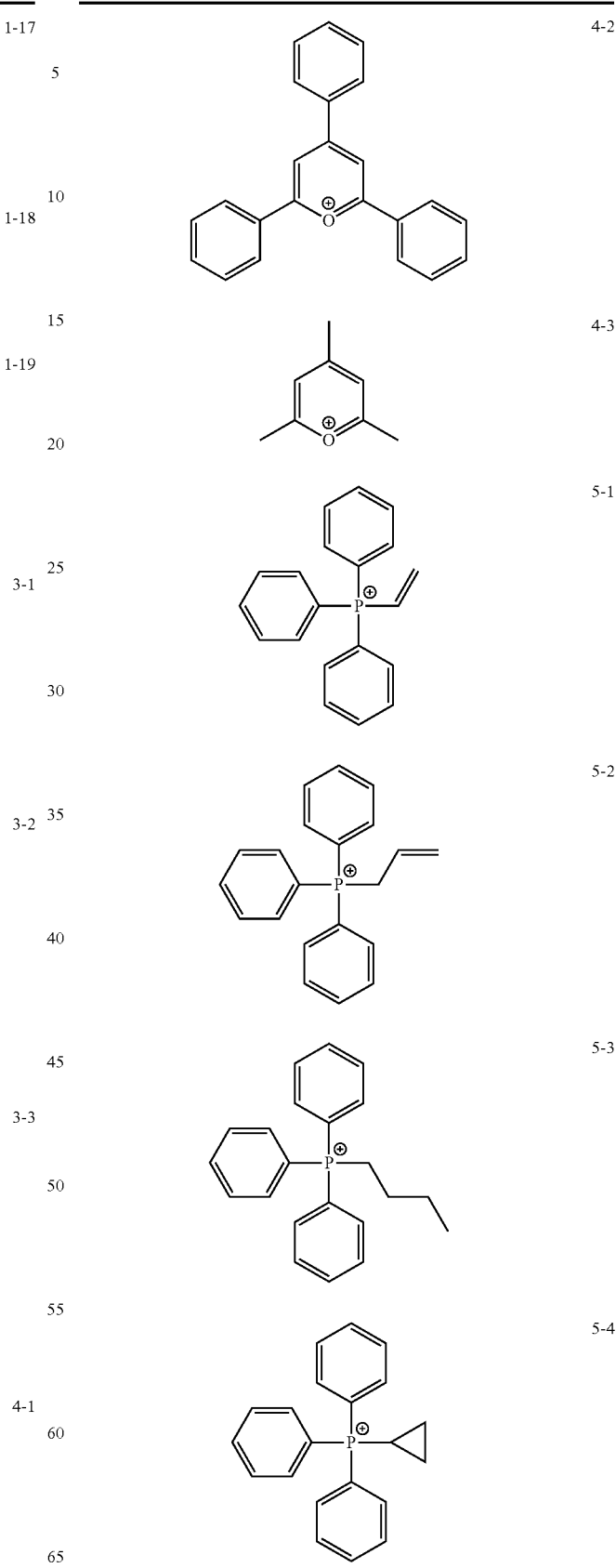

5-5
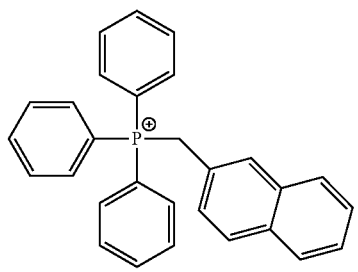
5-6
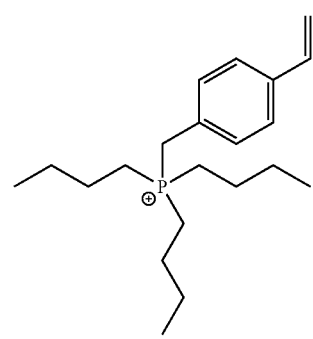
6-1
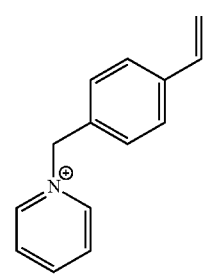
6-2
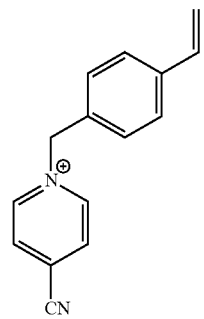
6-3
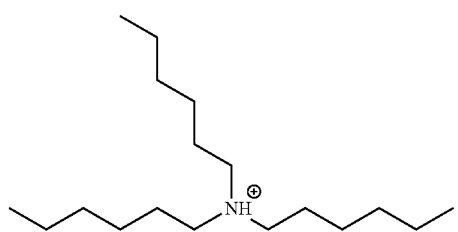
6-4
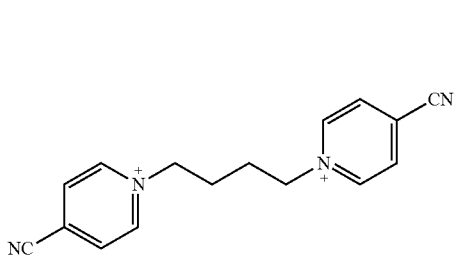
In one embodiment of the present specification, the ionic compound is selected from among the following structural formulae.
[Chemical Formula 1-1-1]
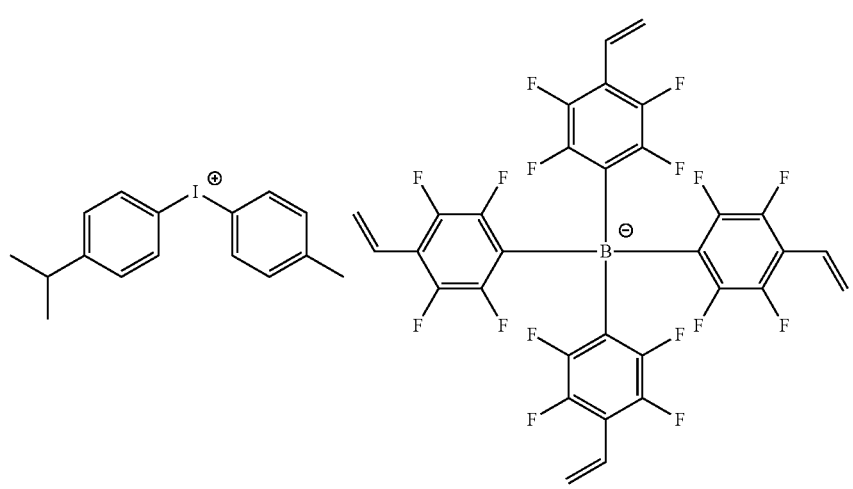

-continued
[Chemical Formula 1-1-2]
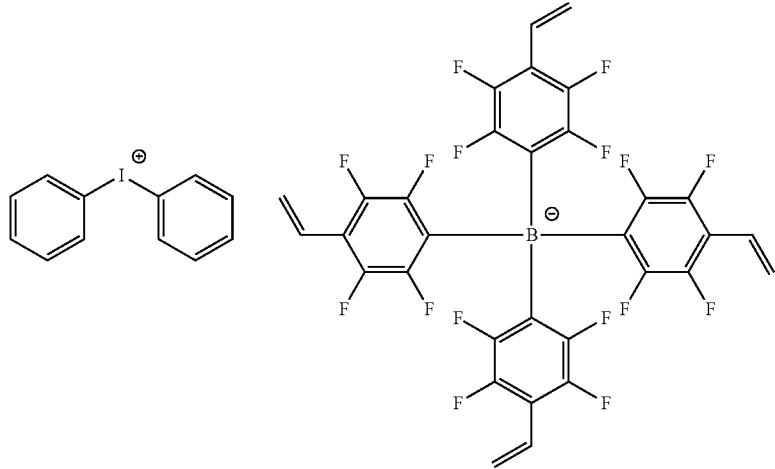
[Chemical Formula 1-1-3]
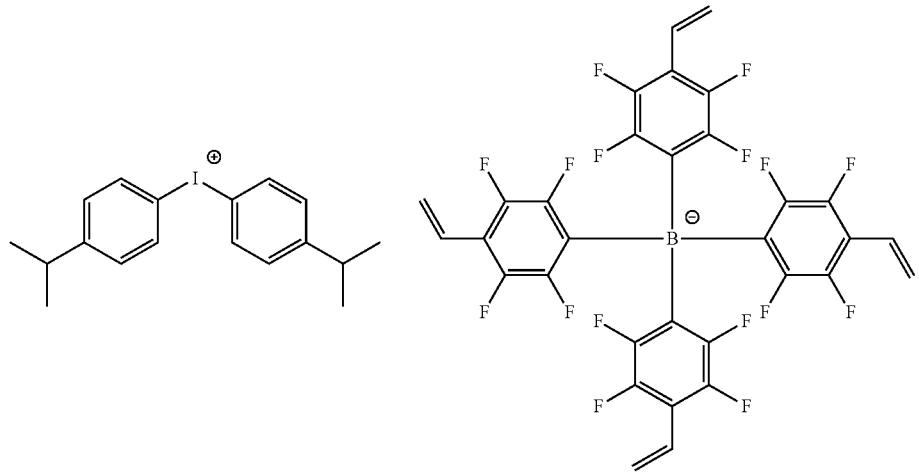
[Chemical Formula 1-1-4]
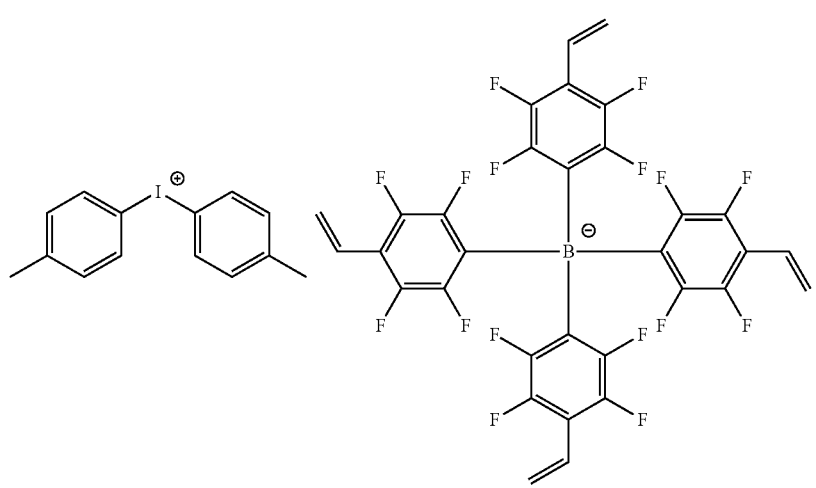

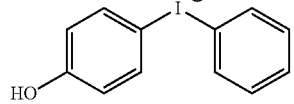 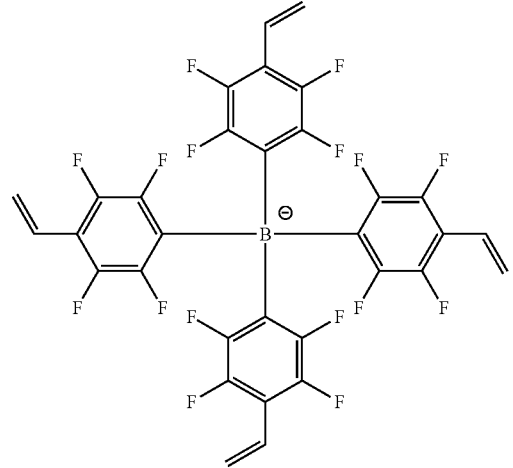
[Chemical Formula 1-1-5]
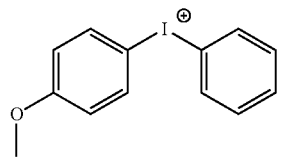 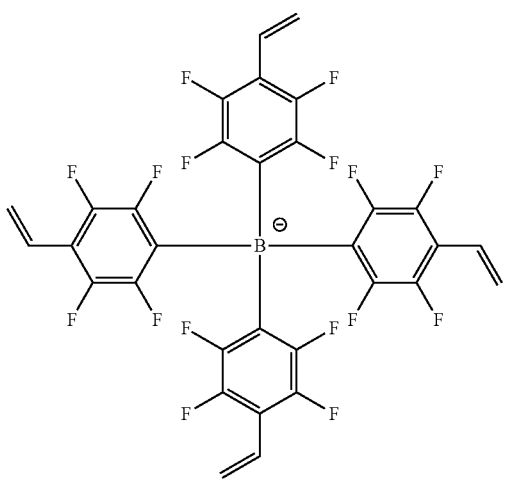
[Chemical Formula 1-1-6]
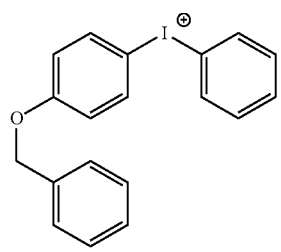 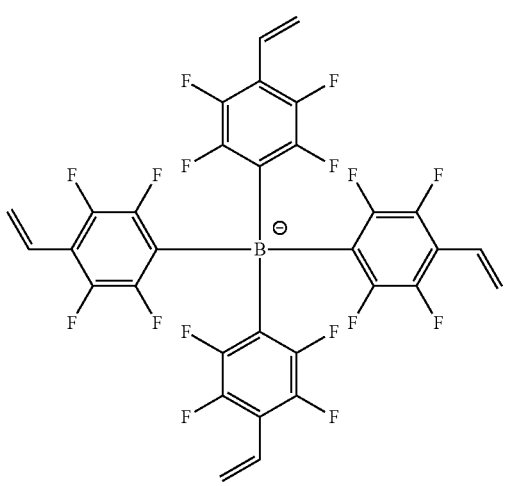
[Chemical Formula 1-1-7]

-continued
[Chemical Formula 1-1-8]
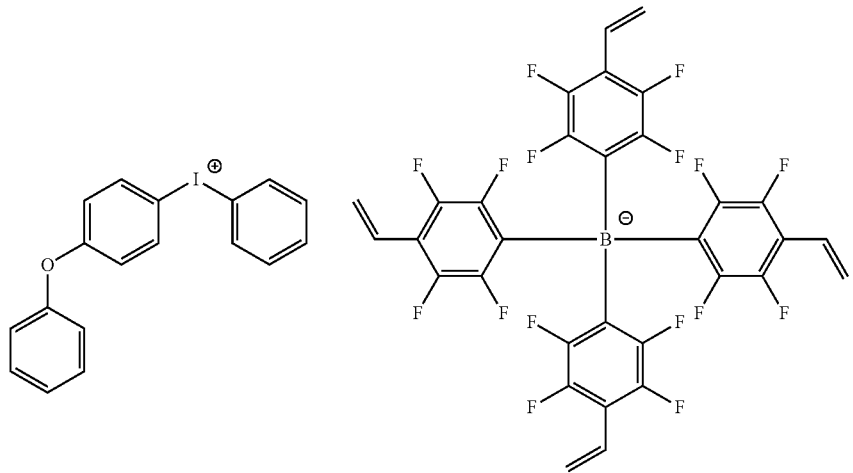
[Chemical Formula 1-1-9]
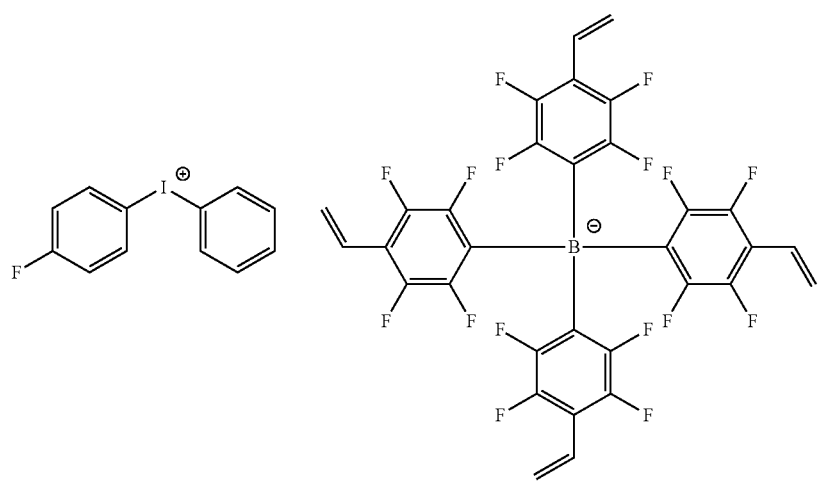
[Chemical Formula 1-1-10]
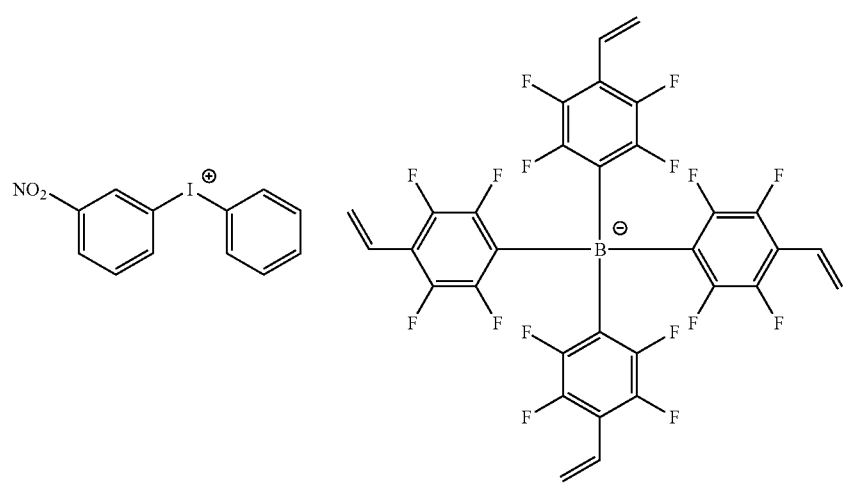

-continued
[Chemical Formula 1-1-11]
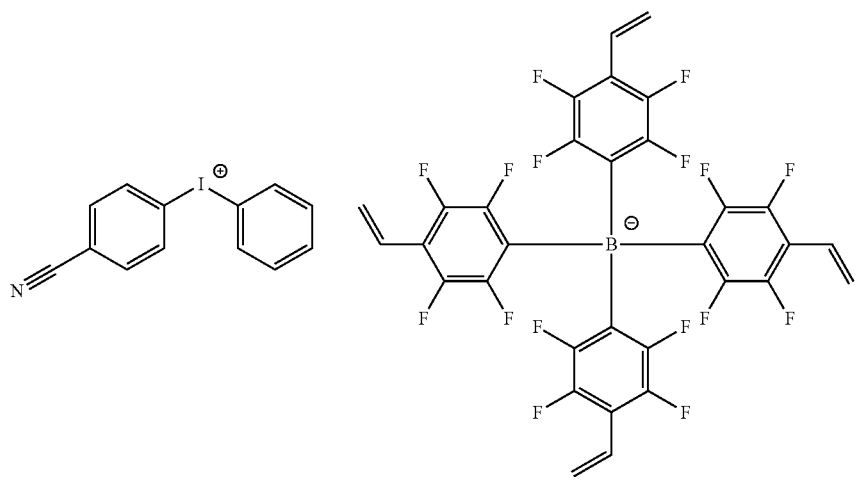
[Chemical Formula 1-1-12]
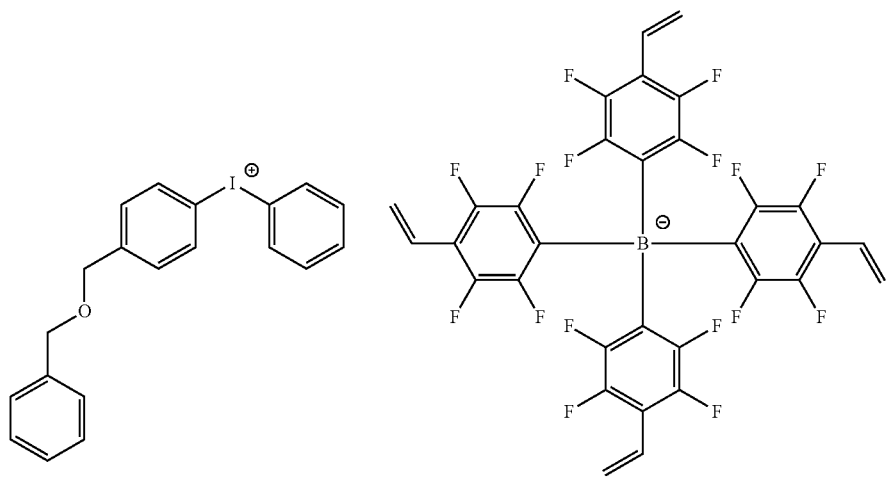
[Chemical Formula 1-1-13]
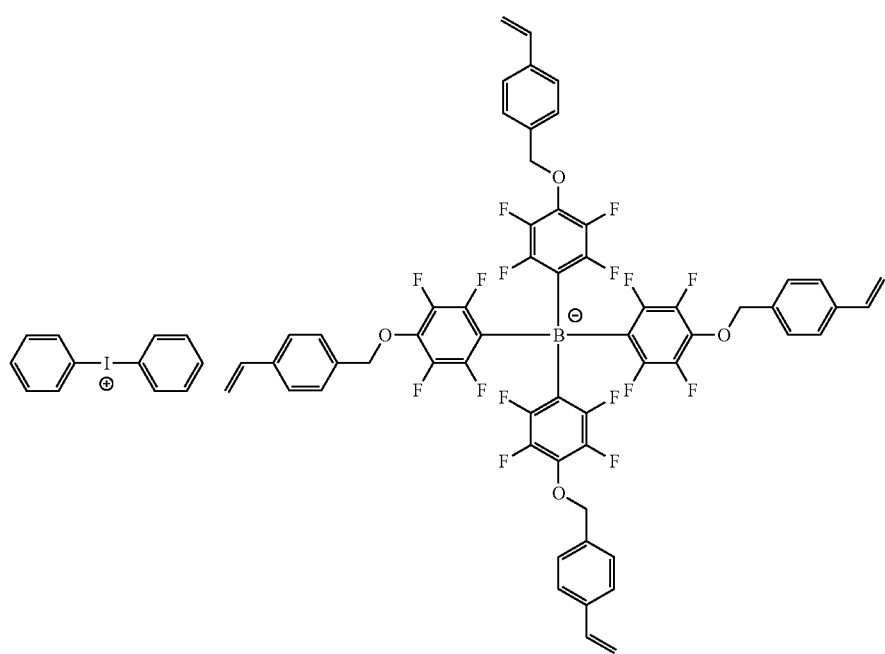

-continued
[Chemical Formula 1-1-14]
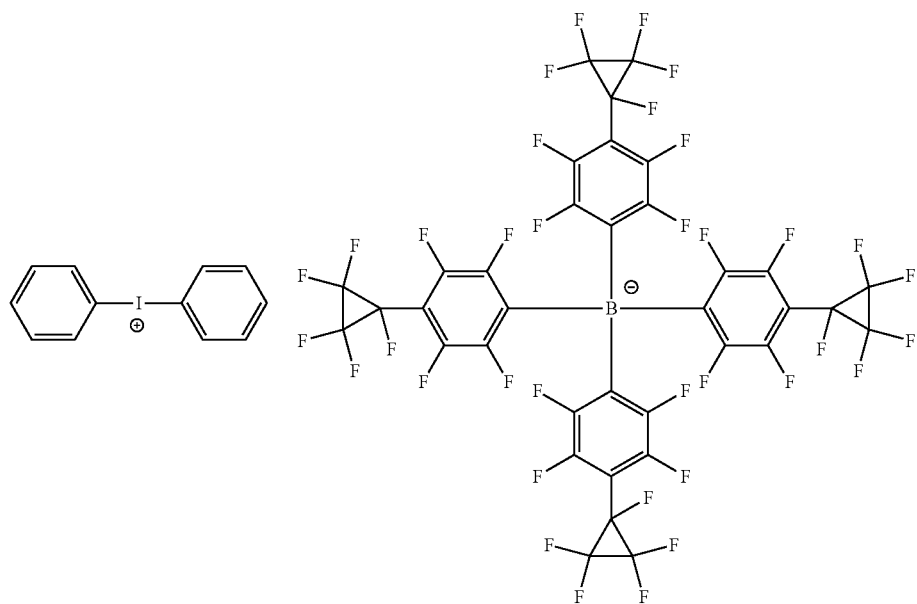
[Chemical Formula 1-1-15]
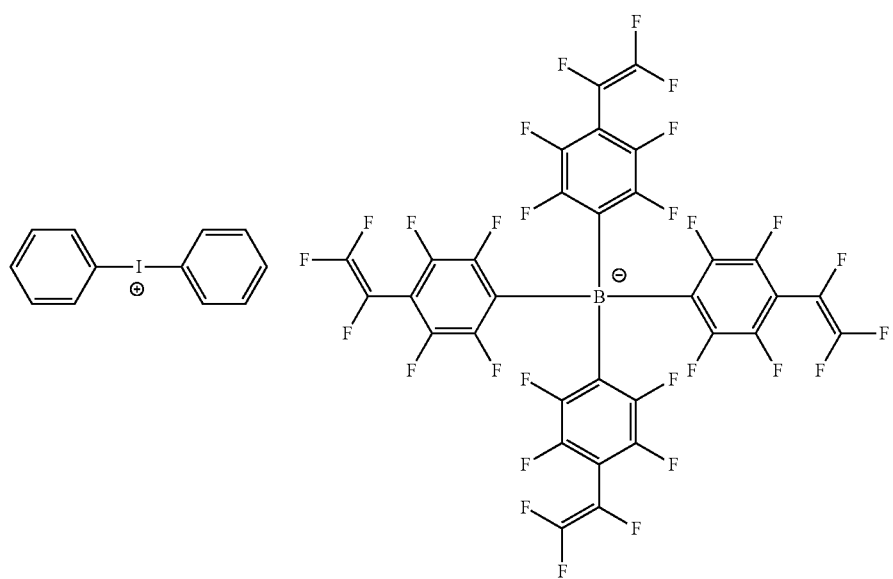
[Chemical Formula 1-1-16]
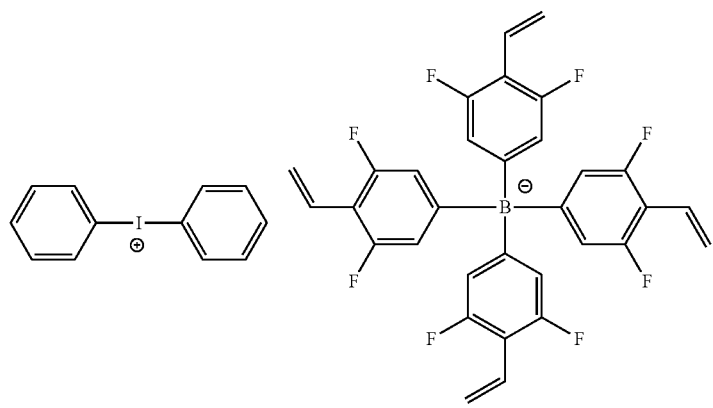

[Chemical Formula 1-1-17]
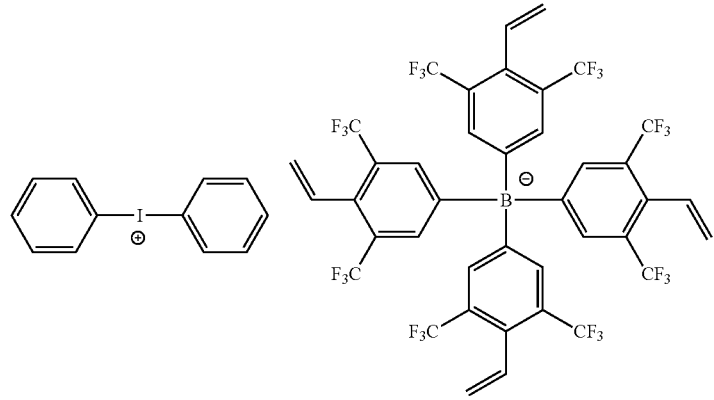
[Chemical Formula 1-1-18]
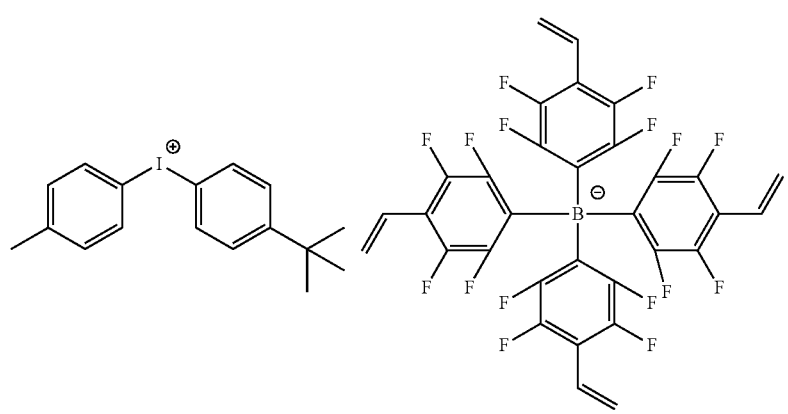
[Chemical Formula 1-1-19]
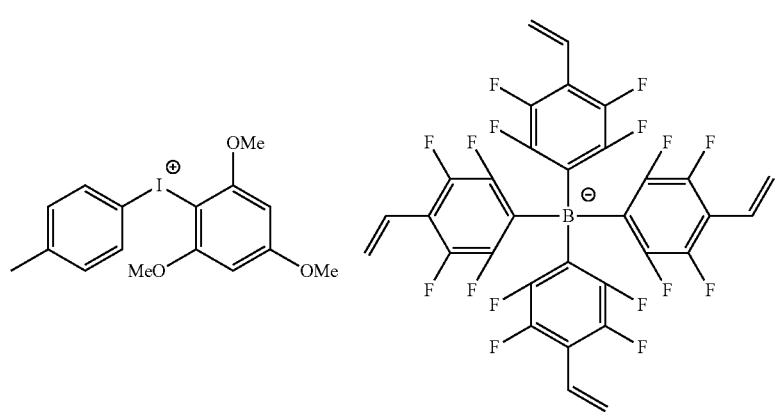

[Chemical Formula 1-2-1]
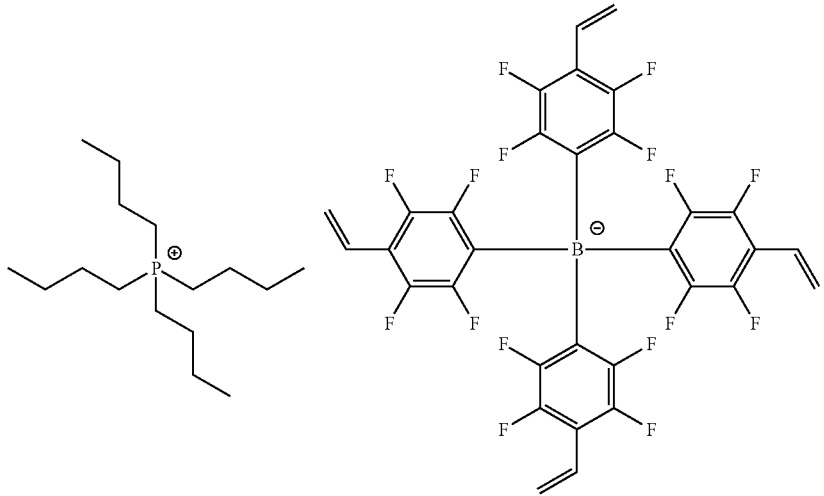
[Chemical 1-2-2]
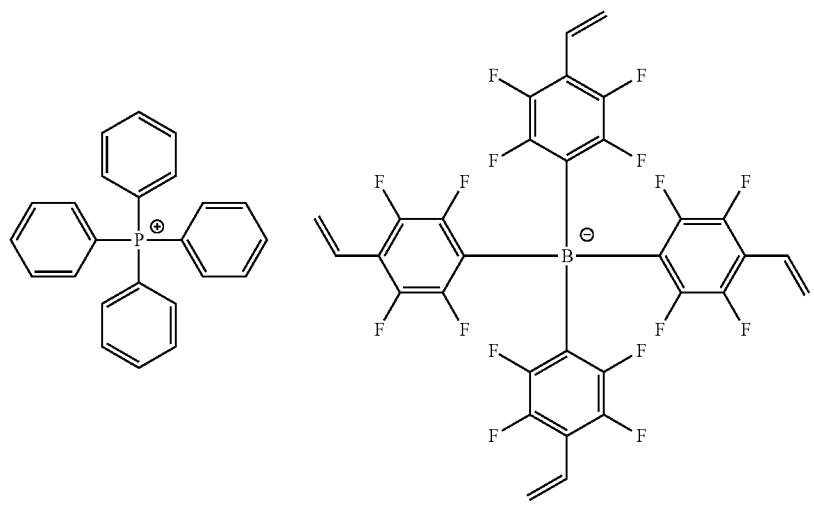
[Chemical Formula 1-2-3]
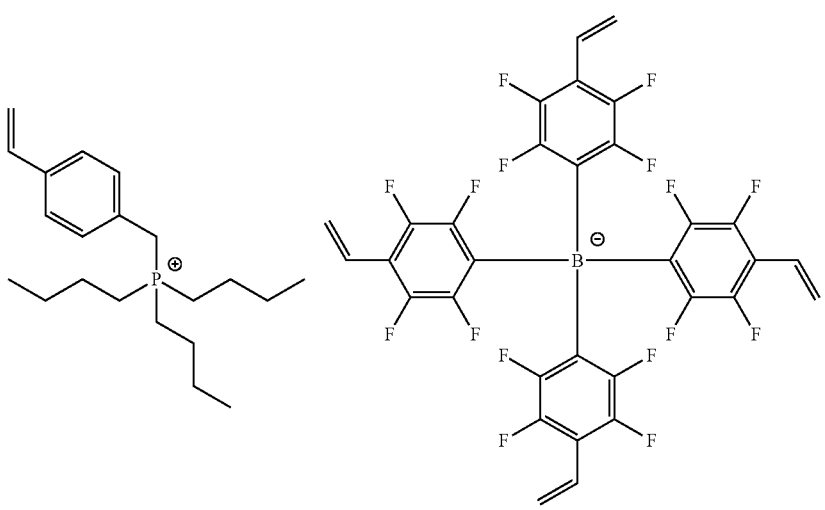

[Chemical Formula 1-2-4]
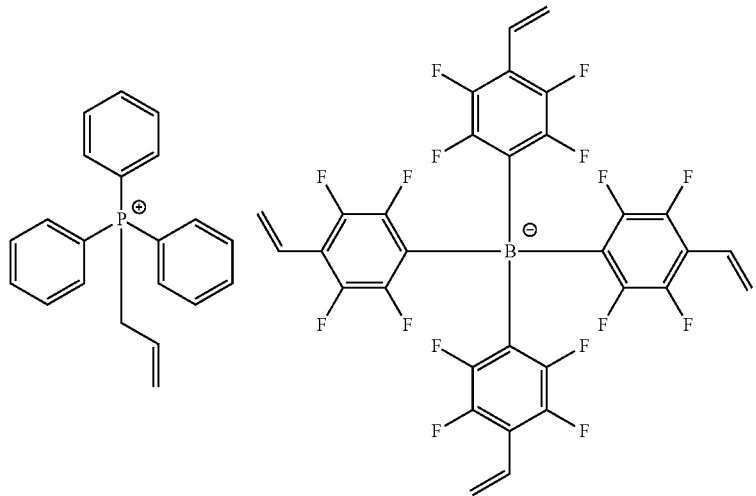
[Chemical Formula 1-2-5]
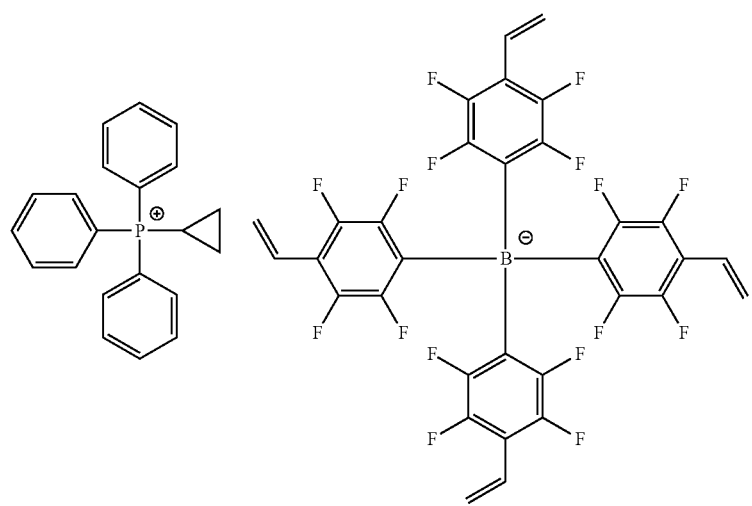
[Chemical 1-3-1]
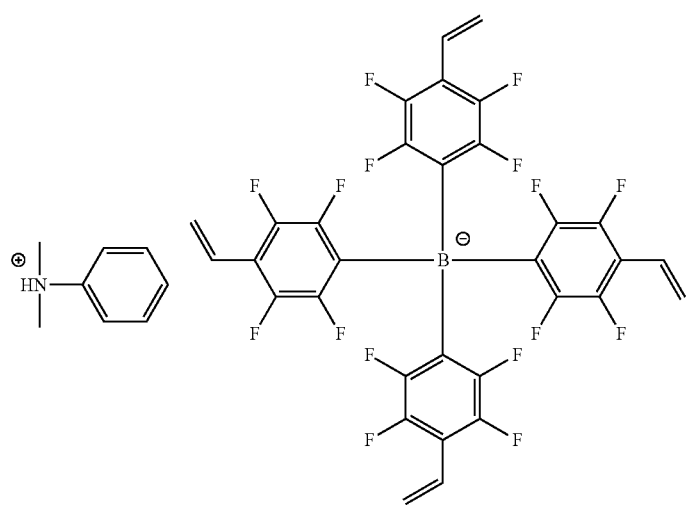

-continued
[Chemical Formula 1-3-2]
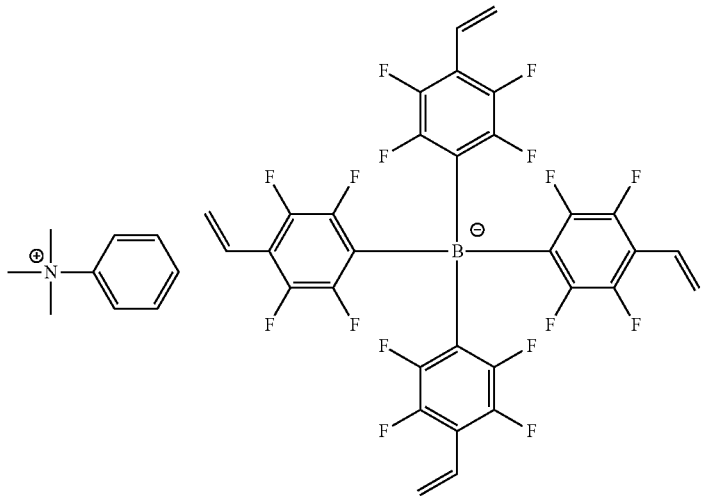
[Chemical Formula 1-3-3]
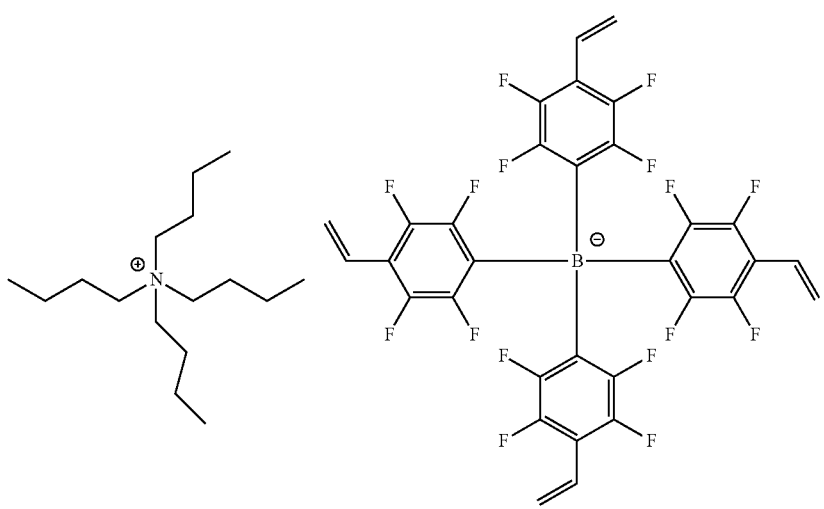
[Chemical Formula 1-3-4]
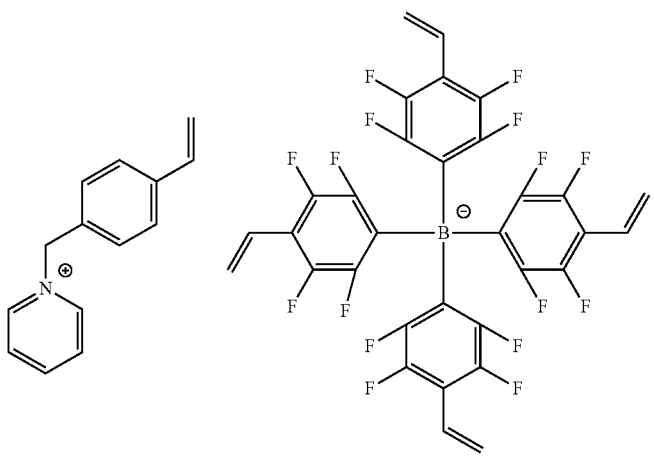

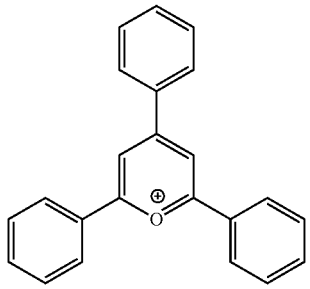

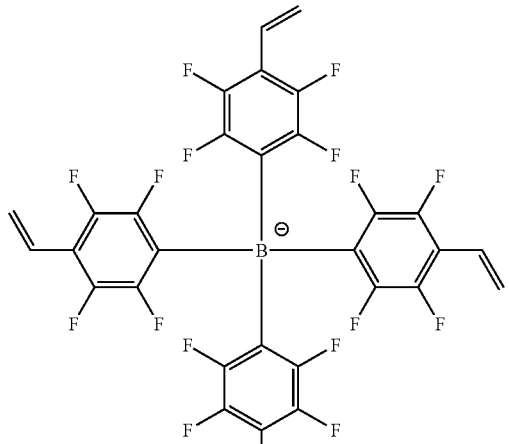

[Chemical Formula 1-4-1]

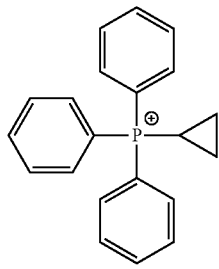

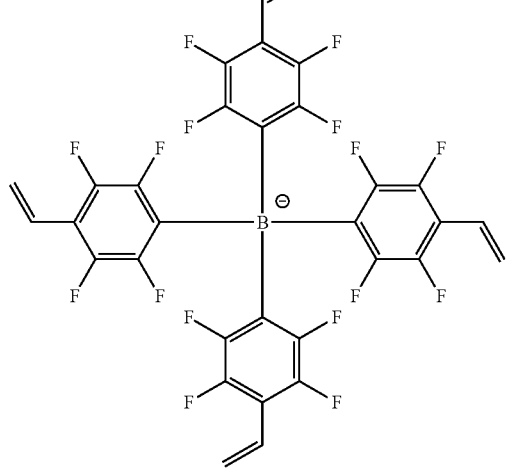

[Chemical Formula 1-5-1]

One embodiment of the present specification provides a coating composition including the ionic compound including the anion group of Chemical Formula 1.

In one embodiment of the present specification, the coating composition including the ionic compound is a coating composition for an organic light emitting device.

In one embodiment of the present specification, the coating composition may be a liquid phase. The "liquid phase" means in a liquid state at room temperature and atmospheric pressure.

In one embodiment of the present specification, examples of the solvent may include chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone or cyclohexanone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; benzoate-based solvents such as methyl benzoate, butyl benzoate or 3-phenoxybenzoate; tetraline, and the like, however, the solvent is not limited as long as it is a solvent capable of dissolving or dispersing the compound according to one embodiment of the present disclosure.

In another embodiment, the solvent may be used either alone as one type, or as a mixture mixing two or more solvent types.

In another embodiment, the solvent preferably has a boiling point of 40° C. to 250° C., and more preferably 60° C. to 230° C., however, the boiling point is not limited thereto.

In another embodiment, the single or mixed solvent preferably has viscosity of 1 CP to 10 CP, and more preferably 3 CP to 8 CP, however, the viscosity is not limited thereto.

In another embodiment, the coating composition preferably has a concentration of 0.1 wt/v % to 20 wt/v %, and more preferably 0.5 wt/v % to 5 wt/v %, however, the concentration is not limited thereto.

In one embodiment of the present specification, the coating composition may further include one, two or more types of additives selected from the group consisting of thermal polymerization initiators and photopolymerization initiators.

Examples of the thermal polymerization initiator may include peroxides such as methyl ethyl ketone peroxide, methyl isobutyl ketone peroxide, acetylacetone peroxide, methylcyclohexanone peroxide, cyclohexanone peroxide, isobutyryl peroxide, 2,4-dichlorobenzoyl peroxide, bis-3,5,5-trimethyl hexanoyl peroxide, lauryl peroxide, benzoyl peroxide, p-chlorobenzoyl peroxide, dicumyl peroxide, 2,5-dimethyl-2,5-(t-butyloxy)-hexane, 1,3-bis(t-butylperoxyisopropyl)benzene, t-butyl cumyl peroxide, di-t-butyl peroxide, 2,5-dimethyl-2,5-(di-t-butylperoxy)hexane-3, tris-(t-butylperoxy)triazine, 1,1-di-t-butylperoxy-3,3,5-trimethylcyclohexane, 1,1-di-t-butylperoxycyclohexane, 2,2-di(t-butylperoxy)butane, 4,4-di-t-butylperoxy valeric acid n-butyl ester, 2,2-bis(4,4-t-butylperoxycyclohexyl)propane, t-butyl peroxyisobutyrate, di-t-butyl peroxyhexahydroterephthalate, t-butylperoxy-3,5,5-trimethylhexate, t-butyl peroxybenzoate or di-t-butyl peroxytrimethyl adipate; or azo-based such as azobis isobutylnitrile, azobis dimethylvaleronitrile or azobis cyclohexyl nitrile, but are not limited thereto.

Examples of the photopolymerization initiator may include acetophenone-based or ketal-based photopolymerization initiators such as diethoxyacetophenone, 2,2-dimethoxy-1,2-diphenyl ethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl)propan-1-one or 1-phenyl-1,2-propanedion-2-(o-ethoxycarbonyl)oxime; benzoin ether-based photopolymerization initiators such as benzoin, benzoin methyl ether, benzoin ethyl ether, benzoin isobutyl ether or benzoin isopropyl ether; benzophenone-based photopolymerization initiators such as benzophenone, 4-hydroxybenzophenone, 2-benzoylnaphthalene, 4-benzoylbiphenyl, 4-benzoyl phenyl ether, acrylated benzophenone or 1,4-benzoylbenzene; thioxanthone-based photopolymerization initiators such as 2-isopropylthioxanthone, 2-chlorothioxanthone, 2,4-dimethylthioxanthone, 2,4-diethylthioxanthone or 2,4-dichlorothioxanthone; and, as other photopolymerization initiators, ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenylglyoxyester, 9,10-phenanthrene, acridine-based compounds, triazine-based compounds, imidazole-based compounds, and the like. In addition, those having a photopolymerization facilitating effect may be used either alone or together with the photopolymerization initiator. Examples thereof may include triethanolamine, methyldiethanolamine, ethyl 4-dimethylaminobenzoate, isoamyl 4-dimethylaminobenzoate, (2-dimethylamino)ethyl benzoate, 4,4'-dimethylaminobenzophenone and the like, but are not limited thereto.

Another embodiment of the present specification provides an organic light emitting device formed using the coating composition.

In one embodiment of the present specification, the organic light emitting device includes a first electrode; a second electrode; and one or more organic material layers provided between the first electrode and the second electrode, wherein one or more layers of the organic material layers are formed using a coating composition including an ionic compound including the anion group of Chemical Formula 1.

In one embodiment of the present specification, the organic light emitting device includes a first electrode; a second electrode; and one or more organic material layers provided between the first electrode and the second electrode, wherein one or more layers of the organic material layers include a cured material of a coating composition including an ionic compound including the anion group of Chemical Formula 1.

In one embodiment of the present specification, the cured material of the coating composition is in a cured state by heat treating or light treating the coating composition.

In one embodiment of the present specification, the organic material layer including the cured material of the coating composition is a hole injection layer.

In one embodiment of the present specification, the organic material layer including the cured material of the coating composition is a hole injection layer, and the ionic compound of the cured material of the coating composition is included as a p-doping material of the hole injection layer.

In one embodiment of the present specification, the organic material layer including the cured material of the coating composition is a hole injection layer, and the ionic compound including the anion group of Chemical Formula 1 is included as a dopant of the hole injection layer.

In one embodiment of the present specification, the organic material layer including the cured material of the coating composition is a hole injection layer, and the ionic compound including the anion group of Chemical Formula 1 is included as a p-doping material of the hole injection layer.

In the present specification, the p-doping material means a material enabling a host material to have a p semiconductor property. The p semiconductor property means a property receiving holes through injection or transferring holes at a highest occupied molecular orbital (HOMO) energy level, that is, a property of a material having high hole conductivity.

In one embodiment of the present specification, the organic material layer formed using the coating composition is a hole injection layer, and the ionic compound including the anion group of Chemical Formula 1 is a dopant of the hole injection layer, and an arylamine compound is included as a host of the hole injection layer.

In one embodiment of the present specification, the arylamine compound is a monomer or a polymer.

In one embodiment of the present specification, an arylamine compound that is a monomer or a polymer is further included as a host of the hole injection layer.

In one embodiment of the present specification, the arylamine compound includes one of the following-structured curing groups.

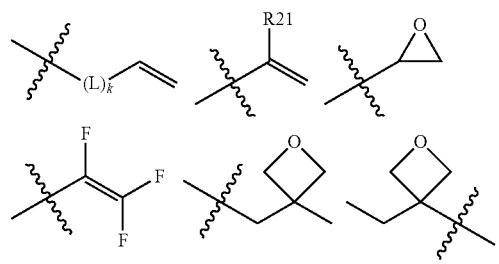

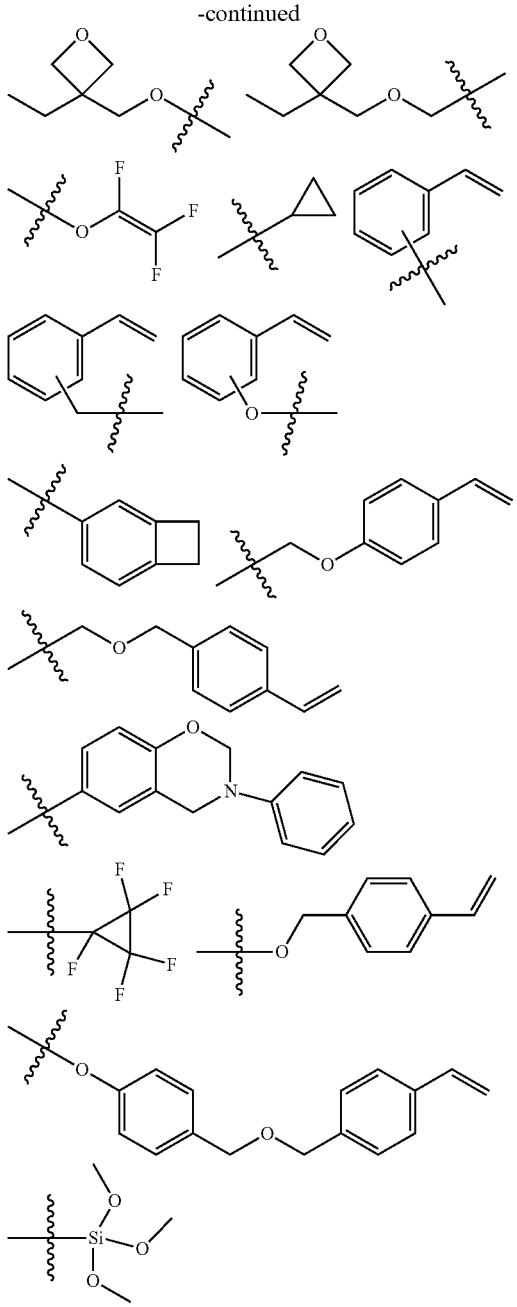

In the structural formulae, L is a direct bond; O; S; a substituted or unsubstituted alkylene group; a substituted or unsubstituted arylene group; or a substituted or unsubstituted divalent heterocyclic group, and k is an integer of 1 or 2, and when k is 2, substituents in the parentheses are different from each other, and R21 is a substituted or unsubstituted alkyl group.

In one embodiment of the present specification, the host of the hole injection layer has a HOMO level from 4.8 eV to 5.8 eV.

The HOMO level of the present specification is measured using an electrochemical cyclic voltammetry method (CV). Onset potential ($E_{onset}$) at which host material oxidation begins is measured, and ferrocene potential ($E_{1/2(Fc)}$) is measured under the same condition. The ferrocene potential is defined as 4.8 eV with respect to a vacuum energy level, and the HOMO level is calculated using the following equation.

$$\text{HOMO(eV)}=4.8+(E_{onset}-E_{1/2(Fc)})$$

The compound of the arylamine group forms crosslinking, and an organic material layer including a thin-filmed structure is capable of being provided. In this case, being dissolved by a solvent deposited on a surface of the organic material layer formed using the coating composition, or being morphologically influenced or decomposed may be prevented.

Accordingly, when the organic material layer formed using the coating composition is formed including a step of heat treatment or light treatment, resistance for a solvent increases, and a multilayer may be formed by repeatedly performing solution deposition and crosslinking method, and as a result, a lifetime property of a device may be enhanced due to increased stability.

In one embodiment of the present specification, the organic material layer formed using the coating composition is a hole transfer layer, a hole injection layer, or a layer carrying out hole transfer and hole injection at the same time.

In another embodiment, the organic material layer formed using the coating composition is a light emitting layer.

In one embodiment of the present specification, the organic light emitting device further includes one, two or more layers selected from the group consisting of a hole injection layer, a hole transfer layer. an electron transfer layer, an electron injection layer, an electron blocking layer and a hole blocking layer.

In one embodiment of the present specification, the first electrode is a cathode, and the second electrode is an anode.

In one embodiment of the present specification, the first electrode is an anode, and the second electrode is a cathode.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

Figure 1:
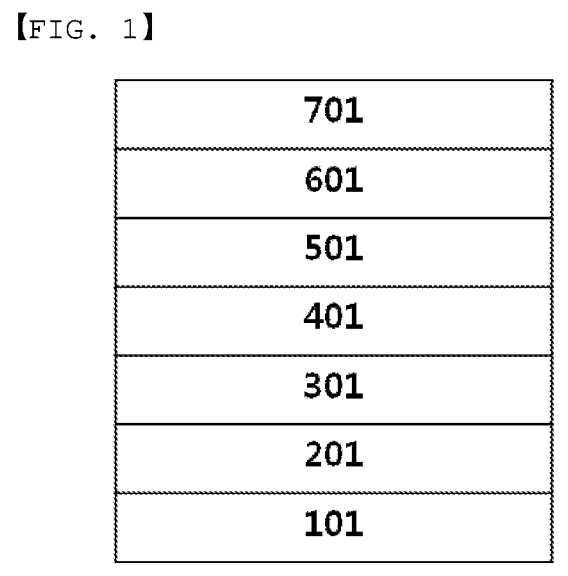

For example, a structure of the organic light emitting device according to one embodiment of the present specification is illustrated in FIG. 1.

FIG. 1 illustrates a structure of the organic light emitting device in which an anode (201), a hole injection layer (301), a hole transfer layer (401), a light emitting layer (501), an electron transfer layer (601) and a cathode (701) are consecutively laminated on a substrate (101).

In FIG. 1, the hole injection layer (301), the hole transfer layer (401) and the light emitting layer (501) are formed using a coating composition including the compound represented by Chemical Formula 1.

FIG. 1 illustrates the organic light emitting device, however, the organic light emitting device is not limited thereto.

When the organic light emitting device includes a plurality of organic material layers, the organic material layers may be formed with materials that are the same as or different from each other.

The organic light emitting device of the present specification may be manufactured using materials and methods known in the art, except that one or more layers of the organic material layers are formed using the coating composition including the compound.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

One embodiment of the present specification also provides a method for manufacturing an organic light emitting device formed using the coating composition.

Specifically, the method for manufacturing an organic light emitting device in one embodiment of the present specification includes preparing a substrate; forming a cathode or an anode on the substrate; forming one or more organic material layers on the cathode or the anode; and forming an anode or a cathode on the organic material layers, wherein one or more layers of the organic material layers are formed using the coating composition.

In one embodiment of the present specification, the organic material layer formed using the coating composition is formed using spin coating.

In another embodiment, the organic material layer formed using the coating composition is formed using a printing method.

In an embodiment of the present specification, examples of the printing method include inkjet printing, nozzle printing, offset printing, transfer printing, screen printing or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the forming of an organic material layer formed using the coating composition includes coating the coating composition on the cathode or the anode; and heat treating or light treating the coated coating composition.

In one embodiment of the present specification, the time of heat treating the organic material layer formed using the coating composition is preferably within 1 hour and more preferably within 30 minutes.

In one embodiment of the present specification, the atmosphere of heat treating the organic material layer formed using the coating composition is preferably inert gas such as argon or nitrogen.

In addition, the composition according to one embodiment of the present specification may be thin-filmed through heat treatment or light treatment, and may be included as a copolymer using a coating composition mixed with other monomers. In addition, a copolymer or a mixture may be included using a coating composition mixed with other polymers.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as $LiF/Al$ or $LiO_2/Al$, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)-based polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including Alq$_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, BCP, aluminum complexes and the like are included, however, the material is not limited thereto.

The organic light emitting device according to the present specification may be a top-emission type, a bottom-emission type or a dual-emission type depending on the materials used.

In one embodiment of the present specification, the coating composition may be included in organic solar cells or organic transistors in addition to organic light emitting devices.

Hereinafter, the present specification will be described in detail with reference to examples in order to specifically describe the present specification. However, the examples according to the present specification may be modified to various different forms, and the scope of the present specification is not to be construed as being limited to the examples described below. Examples of the present specification are provided in order to more fully describe the present specification to those having average knowledge in the art.

EXAMPLE

Preparation Example 1

Preparation of Compound 1

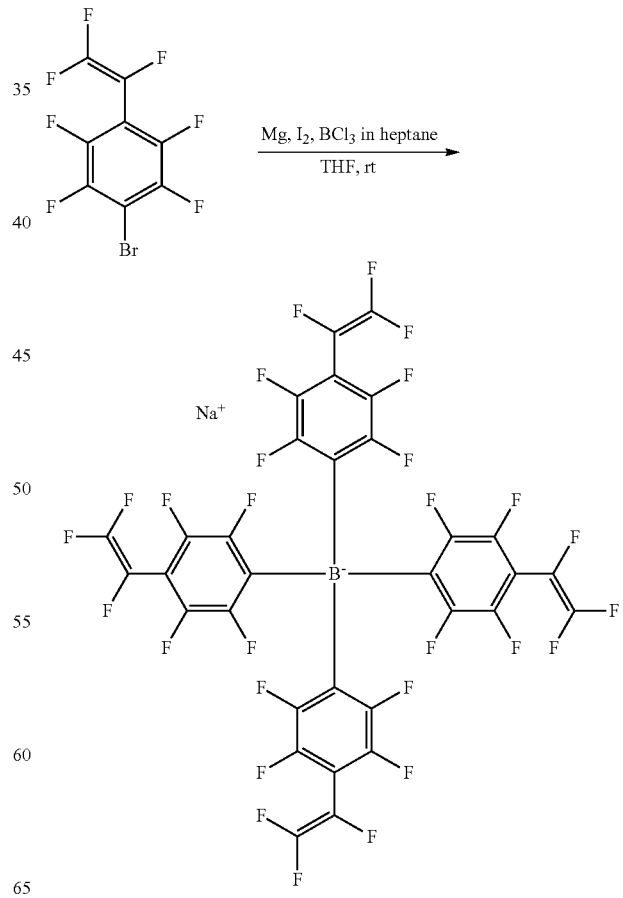

Mg (95 mg, 3.9214 mmol), THF (10 mL) and I$_2$ (4 mg) were placed in a 25 mL round bottom flask, and stirred. 1-Bromo-2,3,5,6-tetrafluoro-4-(1,2,2-trifluorovinyl)benzene (1.2 g, 3.9214 mmol) was introduced to the reaction solution, and the result was stirred at room temperature. After 10 hours, dissolution of Mg was identified by the solution becoming black, and ether (10 mL) and BCl$_3$ (1.3 mL, 1.3 mmol, 1 M in hexane solution) were added thereto over 30 minutes. After stirring the reaction solution for a day, Na$_2$CO$_3$ (30 mL, 3.0 mmol, 0.1 M in H$_2$O) was added thereto. The synthesized material was extracted using EA (3×10 mL), and then residual water was removed with MgSO$_4$. After removing all the solvent, water was completely removed with Dean-stark using benzene, and the solids were filtered to obtain a target compound (430 mg). (Yield: 35%)

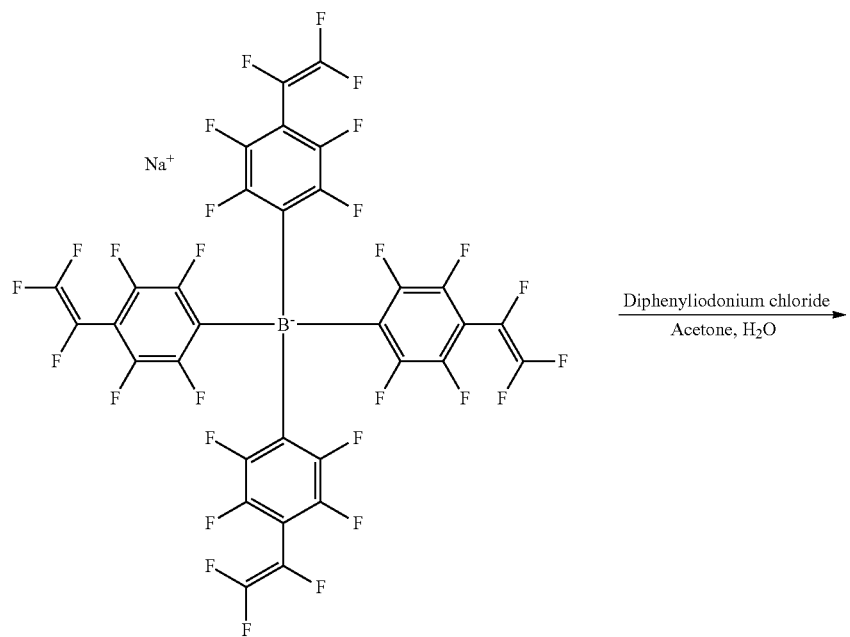

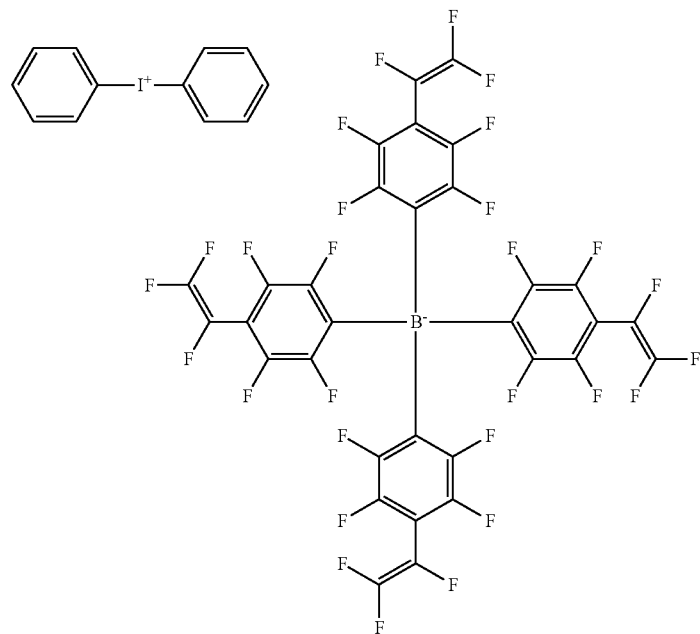

Sodium tetrakis(2,3,5,6-tetrafluoro-4-(1,2,2-trifluorovinyl)phenyl)borate (300 mg, 0.3158 mmol), diphenyliodonium chloride (100 mg, 0.3158 mmol), H₂O (10 mL) and acetone (10 mL) were placed in a 25 mL round bottom flask, and vigorously stirred for 30 minutes. The result was extracted using dichloromethane (10 mL×3), and then dried after removing the solvent to obtain a target compound (381 mg). (Yield: 100%)

Preparation Example 2

Preparation of Compound 2

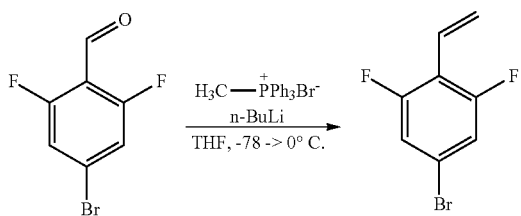

Methyltriphenyl potassium bromide (16 g, 45.2489 mmol) and tetrahydrofuran (THF) (100 mL) were placed in a 250 mL round bottom flask, and stirred for 30 minutes at 0° C. n-BuLi (18.1 mL, 45.2489 mmol, 2.5 M in hexane) was slowly added to the reaction solution, and the result was stirred for 30 minutes at 0° C. At 0° C., 4-bromo-2,6-difluorobenzaldehyde (5.0 g, 22.6244 mmol, in 30 mL tetrahydrofuran (THF)) was slowly added to the reaction solution. The reaction solution was stirred while slowly raising the temperature to room temperature. After 3 hours, ether (100 mL) and a saturated NH₄Cl solution (400 mL) were added to the reaction solution. The organic solvent was extracted using ether (2×200 mL), and residual water was removed with MgSO₄. The result was columned using EA:Hex=1:9 to obtain a target compound (3 g). (Yield: 60%)

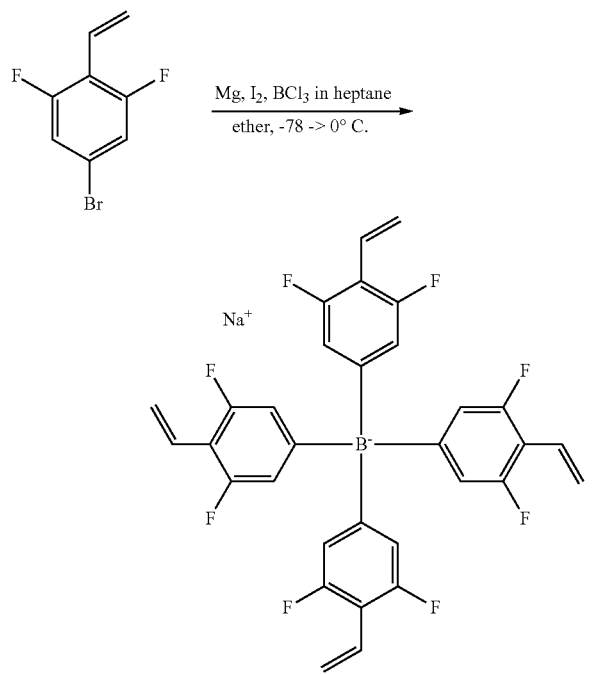

Mg (111 mg, 4.5656 mmol), THF (10 mL) and I₂ (4 mg) were placed in a 25 mL round bottom flask, and stirred. 5-Bromo-1,3-difluoro-2-vinylbenzene (1 g, 4.5656 mmol) was introduced to the reaction solution, and the result was stirred at room temperature. After 10 hours, dissolution of Mg was identified by the solution becoming black, and ether (10 mL) and BCl₃ (1.1 mL, 1.0957 mmol, 1 M in hexane solution) were added thereto over 30 minutes. After stirring the reaction solution for a day, Na₂CO₃ (30 mL, 3.0 mmol, 0.1 M in H₂O) was added thereto. The synthesized material was extracted using EA (3×10 mL), and residual water was removed with MgSO₄. After removing all the solvent, water was completely removed with Dean-stark using benzene, and the solids were filtered to obtain a target compound (400 mg). (Yield: 62%)

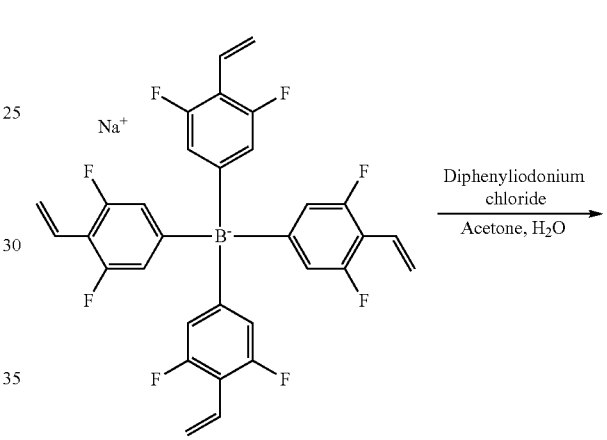

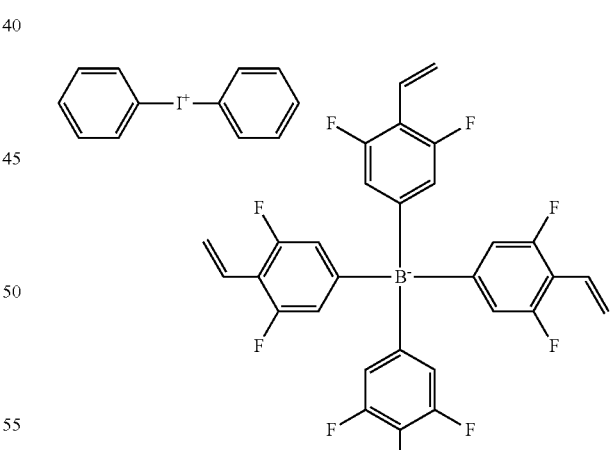

Sodium tetrakis(3,5-difluoro-4-vinylphenyl)borate (400 mg, 0.6776 mmol), diphenyliodonium chloride (215 mg, 0.6776 mmol), H₂O (10 mL) and acetone (10 mL) were placed in a 25 mL round bottom flask, and vigorously stirred for 30 minutes. The result was extracted using dichloromethane (10 mL×3), and then dried after removing the solvent to obtain a target compound (574 mg). (Yield: 100%)

Preparation Example 3

Preparation of Compound 3

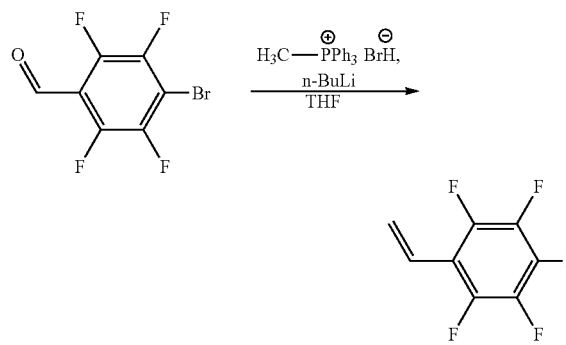

Methyltriphenyl potassium bromide (13.90 g, 38.9135 mmol) and tetrahydrofuran (THF) (100 mL) were placed in a 250 mL round bottom flask, and stirred for 30 minutes at 0° C. n-BuLi (15.6 mL, 38.9135 mmol, 2.5 M in hexane) was slowly added to the reaction solution, and the result was stirred for 30 minutes at 0° C. At 0° C., 4-formyl-2,3,5,6-tetrafluoro-1-bromobenzene (5.0 g, 19.4568 mmol, in 30 mL tetrahydrofuran (THF)) was slowly added to the reaction solution. The reaction solution was stirred while slowly raising the temperature to room temperature. After 3 hours, ether (100 mL) and a saturated NH$_4$Cl solution (400 mL) were added to the reaction solution. The organic solvent was extracted using ether (2×200 mL), and residual water was removed with MgSO$_4$. The result was columned using EA:Hex=1:9 to obtain a target compound (1.29 g). (Yield: 26%)

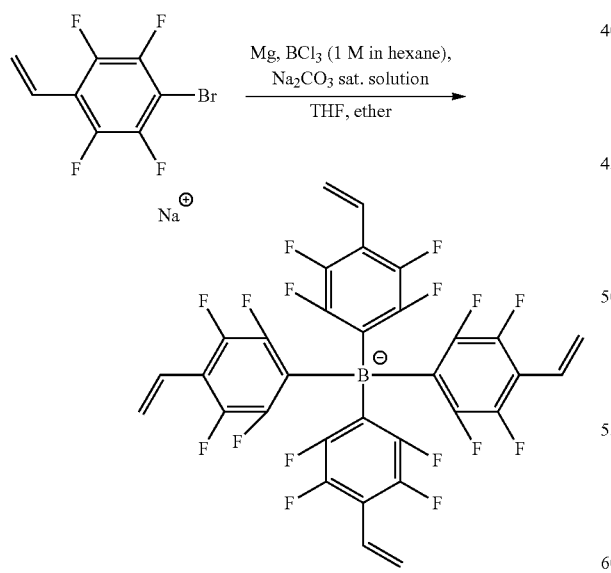

Mg (95 mg, 3.9214 mmol), THF (10 mL) and I$_2$ (4 mg) were placed in a 25 mL round bottom flask, and stirred. 1-Bromo-2,3,5,6-tetrafluoro-4-vinylbenzene (1.0 g, 3.9214 mmol) was introduced to the reaction solution, and the result was stirred at room temperature. After 10 hours, dissolution of Mg was identified by the solution becoming black, and ether (10 mL) and BCl$_3$ (1.3 mL, 1.3 mmol, 1 M in hexane solution) were added thereto over 30 minutes. After stirring the reaction solution for a day, Na$_2$CO$_3$ (30 mL, 3.0 mmol, 0.1 M in H$_2$O) was added thereto. The synthesized material was extracted using EA (3×10 mL), and residual water was removed with MgSO$_4$. After removing all the solvent, water was completely removed with Dean-stark using benzene, and the solids were filtered to obtain a target compound (340 mg). (Yield: 28%)

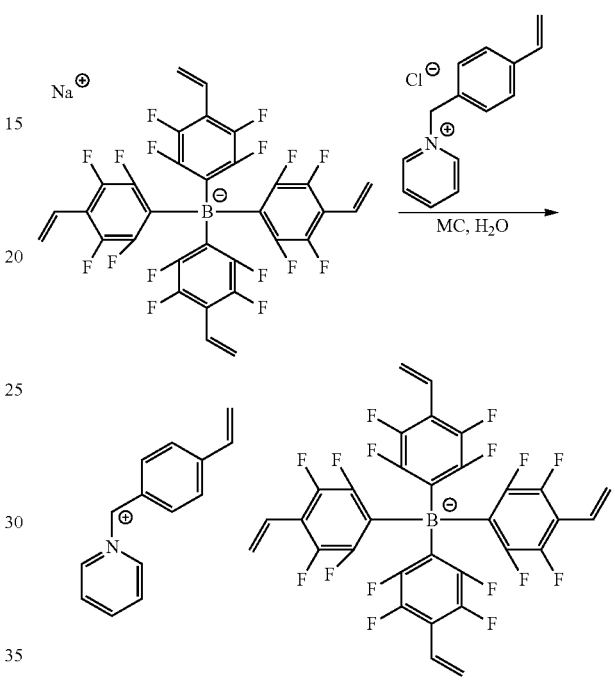

Sodium tetrakis (2,3,5,6-tetrafluoro-4-vinylphenyl)borate (200 mg, 0.2724 mmol), 1-(4-vinylbenzyl)pyridin-1-ium chloride (69 mg, 0.2996 mmol), H$_2$O (10 mL) and MC (10 mL) were placed in a 25 mL round bottom flask, and vigorously stirred for 30 minutes. The organic solvent was extracted using ether (3×10 mL), and residual water was removed with MgSO$_4$. The solvent was removed, and the result was vacuum dried to obtain Compound 3 (247 mg). (Yield: 100%)

Preparation Example 4

Preparation of Compound 4

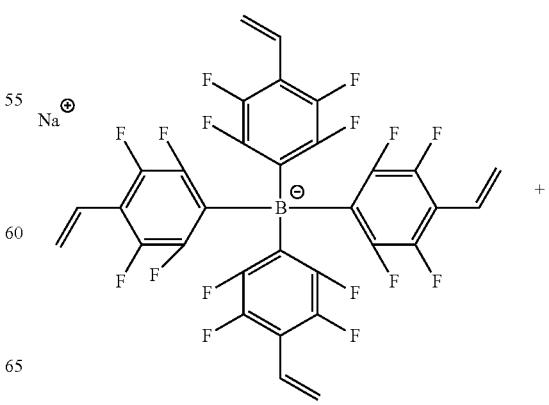

-continued

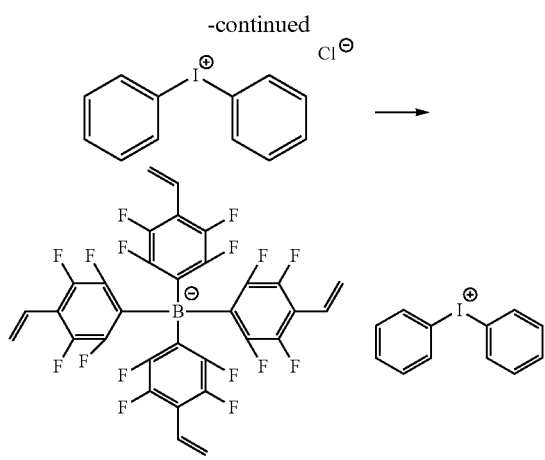

Sodium tetrakis (2,3,5,6-tetrafluoro-4-(perfluorocyclo-propyl)phenyl)borate (501 mg, 0.6823 mmol), diphenyliodonium chloride (216 mg, 0.6823 mmol), H₂O (10 mL) and acetone (10 mL) were placed in a 25 mL round bottom flask, and vigorously stirred for 30 minutes. When precipitates were produced, the precipitates were washed with water to obtain target Compound 4 (677 mg). (Yield: 100%)

MS data of Compound 4 are shown in FIG. 2, DSC data of Compound 4 are shown in FIG. 3, and an NMR spectrum of Compound 4 is shown in FIG. 4.

The DSC data are differential scanning calorimeter data, and curing of the dopant material was seen through FIG. 3.

Preparation Example 5

Preparation of Compound 5

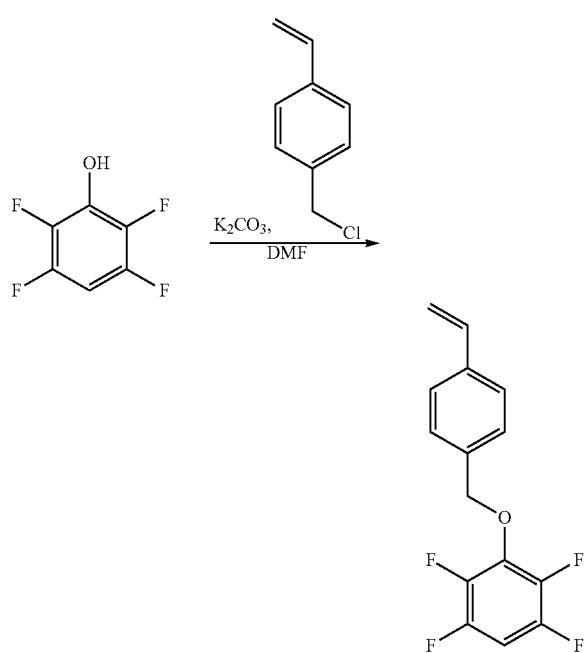

Potassium carbonate (10.4 g, 75.3 mmol) and then dimethylformamide (DMF) (200 ml) were placed in a 500 mL round bottom flask. To the flask, 2,3,5,6-tetrafluorophenol (10.0 g, 60.22 mmol) was introduced, and the result was stirred for 30 minutes at 60° C. 4-Vinylbenzyl chloride (7.66 g, 50.18 mmol) was slowly added to the reaction solution, and the result was stirred for 16 hours at 60° C. After that, H₂O (300 mL) and EA (200 ml) were added. The organic layer was extracted using EA (2×200 mL), and residual water was removed with MgSO₄. The result was columned using EA:Hex=1:9 to obtain a target compound (11.2 g). (Yield: 79%)

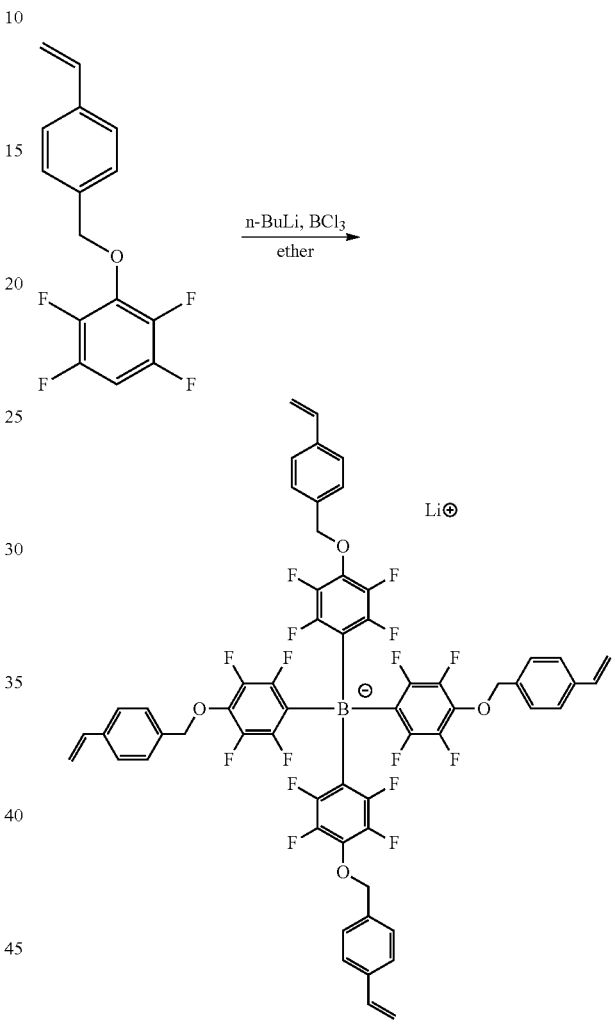

After placing 1,2,4,5-tetrafluoro-3-((4-vinylbenzyl)oxy) benzene (10 g, 35.43 mmol) in a 250 ml round bottom flask, ether (130 ml) was introduced thereto, and the result was stirred. The reaction solution was cooled to −78° C., and stirred for 30 minutes. n-BuLi (17 ml, 42.52 mmol, 2.5 M in hexane) was slowly injected thereto over 30 minutes. After that, the result was stirred for 1 hour. BCl₃ (8.15 ml, 8.15 mmol, 1 M in hexane) was slowly introduced thereto over 30 minutes. After that, the result was further stirred for 2 hours, and the temperature of the reaction solution was slowly raised to room temperature. After stirring the reaction solution for a day, H₂O (200 ml) was added thereto. The synthesized material was extracted using ether (3×100 mL), and all the solvent was removed. After that, water was completely removed with Dean-stark using benzene, and the solids were filtered to obtain a target compound (6.2 g). (Yield: 66%)

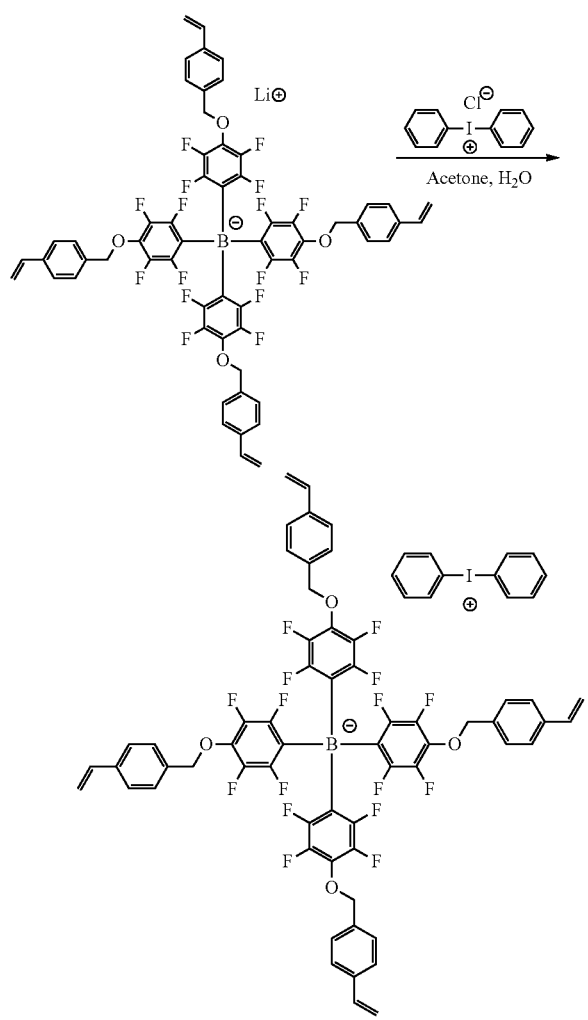

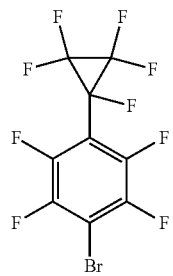

1-Bromo-2,3,5,6-tetrafluoro-4-(1,2,2-trifluorovinyl)benzene (3 g, 9.7093 mmol) and hexafluoropropylene oxide (3 g, 18.0701 mmol) were placed in a 15 mL stainless steel cylinder, and heated for 4 hours at 190° C. After slowly cooling the container, the solution inside the container was washed 3 times with water (5 mL). The organic solution was dried using magnesium sulfate. This mixture was silica column purified using a 9:1 hexane:ethyl acetate solvent to obtain a target compound (1.2 g). (Yield: 34%)

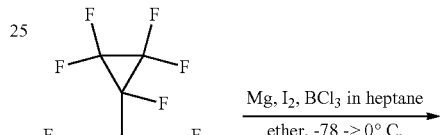

Lithium tetrakis (2,3,5,6-tetrafluoro-4-((4-vinylbenzyl)oxy)phenyl)borate (6.2 g, 5.42 mmol), diphenyliodonium chloride (2.57 g, 8.13 mmol), H₂O (50 mL) and acetone (10 mL) were placed in a 25 mL round bottom flask, and vigorously stirred for 30 minutes. The organic solvent was extracted using MC (3×20 mL), and the solvent was removed. The result was columned using MC:acetone=9:1 to obtain target Compound 7 (5.0 g). (Yield: 65%)

[FIG. 9]: NMR Spectrum of Compound 5

Preparation Example 6

Preparation of Compound 6

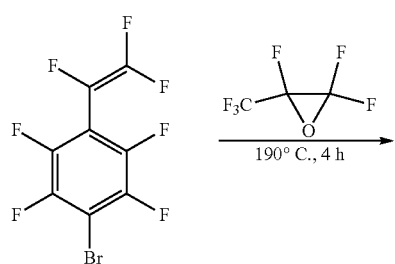

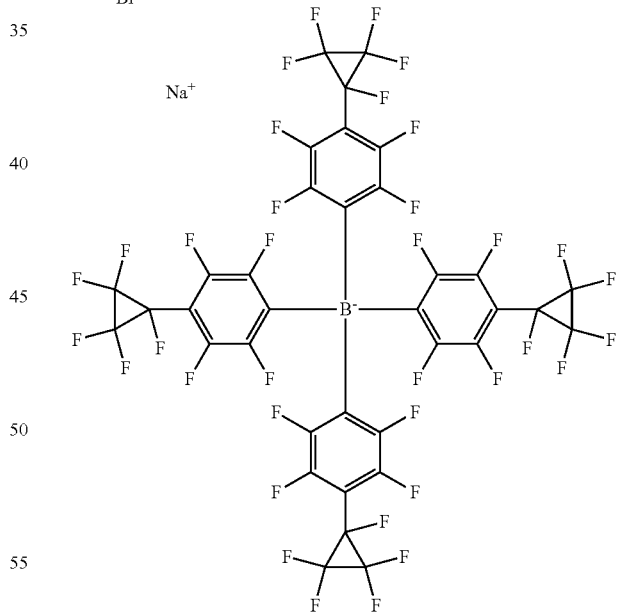

Mg (81 mg, 3.3427 mmol), THF (10 mL) and I₂ (4 mg) were placed in a 25 mL round bottom flask, and stirred. 1-Bromo-2,3,5,6-tetrafluoro-4-(perfluorocyclopropyl)benzene (1.2 g, 3.3427 mmol) was introduced to the reaction solution, and the result was stirred at room temperature. After 10 hours, complete dissolution of Mg was identified by the solution becoming black, and ether (10 mL) and BCl₃ (0.8 mL, 0.8022 mmol, 1 M in heptane solution) were added thereto over 30 minutes. After stirring the reaction solution for a day, Na₂CO₃ (30 mL, 3.0 mmol, 0.1 M in H₂O) was added thereto. The synthesized material was extracted using EA (3×10 mL), and then residual water was removed with MgSO₄. After removing all the solvent, water was completely removed with Dean-stark using benzene, and the solids were filtered to obtain a target compound (410 mg). (Yield: 44%)

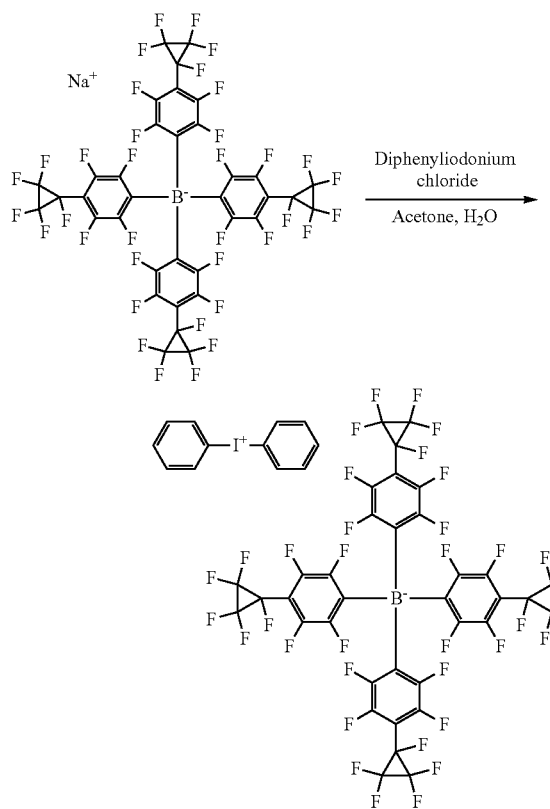

Sodium tetrakis(2,3,5,6-tetrafluoro-4-(perfluorocyclopropyl)phenyl)borate (410 mg, 0.3565 mmol), diphenyliodonium chloride (113 mg, 0.3565 mmol), H₂O (10 mL) and acetone (10 mL) were placed in a 25 mL round bottom flask, and vigorously stirred for 30 minutes. The result was extracted using dichloromethane (10 mL×3) and then dried after removing the solvent to obtain a target Compound 6 (502 mg). (Yield: 100%)

Preparation Example 7

Preparation of Compound 7

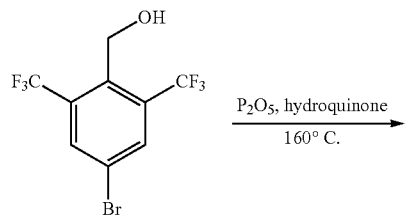

-continued

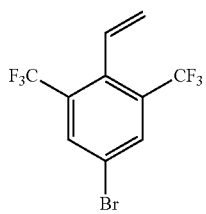

(4-Bromo-2,6-bis(trifluoromethyl)phenyl)methanol (4 g, 12.3828 mmol), phosphorus pentoxide (290 mg, 3.7148 mmol) and hydroquinone (82 mg, 0.7430 mmol) were placed in a 25 mL round bottom flask, and stirred for 1 hour at 160° C. After cooling the reaction solution to room temperature, a saturated aqueous sodium bicarbonate solution (15 mL) was slowly added thereto. The synthesized material was extracted using MC (3×10 mL), and residual water was removed with MgSO₄. After removing the MC solvent, the result was purified using silica gel column chromatography (10% ethyl acetate/hexane), and dried to obtain a target compound (2.6 g). (Yield: 65%)

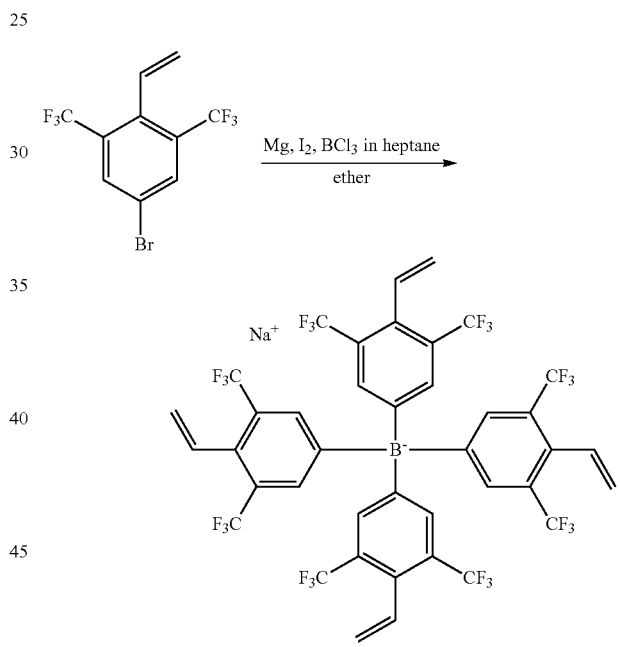

Mg (198 mg, 8.1494 mmol), THF (20 mL) and I₂ (8 mg) were placed in a 100 mL round bottom flask, and stirred. 5-Bromo-1,3-bis(trifluoromethyl)-2-vinylbenzene (2.6 g, 8.1494 mmol) was introduced to the reaction solution, and the result was stirred at room temperature. After 10 hours, dissolution of Mg was identified by the solution becoming black, and ether (20 mL) and BCl₃ (2.0 mL, 1.9559 mmol, 1 M in hexane solution) were added thereto over 30 minutes. After stirring the reaction solution for a day, Na₂CO₃ (40 mL, 3.0 mmol, 0.1 M in H₂O) was added thereto. The synthesized material was extracted using EA (3×20 mL), and residual water was removed with MgSO₄. After removing all the solvent, water was completely removed with Dean-stark using benzene, and the solids were filtered to obtain a target compound (1.1 g). (Yield: 59%)

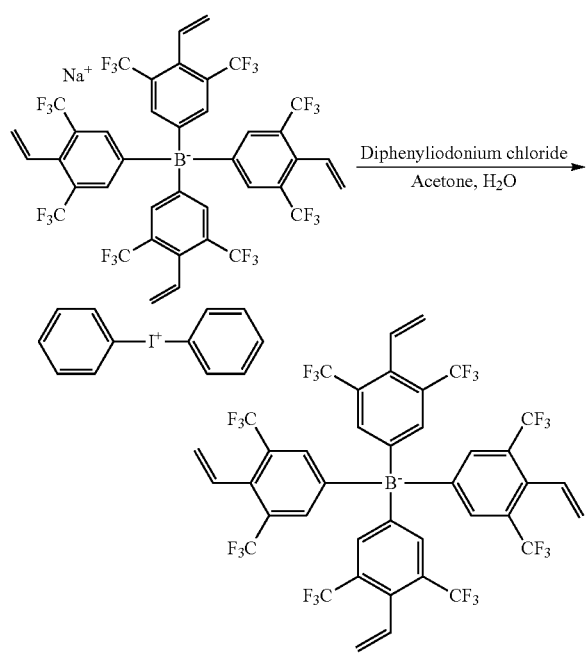

Sodium tetrakis(3,5-bis(trifluoromethyl)-4-vinylphenyl) borate (2 g, 2.0195 mmol), diphenyliodonium chloride (639 mg, 2.0195 mmol), H$_2$O (20 mL) and acetone (20 mL) were placed in a 50 mL round bottom flask, and vigorously stirred for 30 minutes. The result was extracted using dichloromethane (20 mL×3), and then dried after removing the solvent to obtain target Compound 7 (2.5 g). (Yield: 100%)

Experimental Example 1-1

Formation of Coating Layer Using Coating Composition

The coating composition was mixed as described in the following Table 1, and specifically, Coating Composition 1 was produced by mixing a p-doping material represented by the following Compound 1, a host compound that is the following [Compound A], and an organic solvent (cyclohexanone). Specifically, Compound 1, Compound A and the organic solvent were mixed in a weight ratio of 2:8:490 to produce the coating composition, and Coating Composition 1 was spin coated to form a coating layer, and the film was baked at 250° C. or lower.

Coating Composition 2 was produced in the same manner as Coating Composition 1 except that the following Compound 2 was used instead of Compound 1 of the present disclosure. Coating Composition 2 was spin coated to form a coating layer, and the film was baked at 250° C. or lower.

Coating Composition 3 was produced in the same manner as Coating Composition 1 except that the following Compound 3 was used instead of Compound 1 of the present disclosure. Coating Composition 3 was spin coated to form a coating layer, and the film was baked at 250° C. or lower.

Coating Composition 4 was produced in the same manner as Coating Composition 1 except that the following Compound 4 was used instead of Compound 1 of the present disclosure. Coating Composition 4 was spin coated to form a coating layer, and the film was baked at 250° C. or lower.

Coating Composition 5 was produced in the same manner as Coating Composition 4 except that the following [Compound B] was used instead of [Compound A] of the present disclosure. Coating Composition 5 was spin coated to form a coating layer, and the film was baked at 250° C. or lower.

Coating Composition 6 was produced in the same manner as Coating Composition 4 except that the following [Compound C] was used instead of [Compound A] of the present disclosure. Coating Composition 6 was spin coated to form a coating layer, and the film was baked at 250° C. or lower.

Coating Composition 7 was produced in the same manner as Coating Composition 1 except that the following Compound 7 was used instead of Compound 1 of the present disclosure. Coating Composition 7 was spin coated to form a coating layer, and the film was baked at 250° C. or lower.

Coating Composition 8 was produced in the same manner as Coating Composition 1 except that the following Comparative Compound 1 was used instead of Compound 1 of the present disclosure. Coating Composition 8 was spin coated to form a coating layer, and the film was baked at 250° C. or lower.

Coating Composition 9 was produced in the same manner as Coating Composition 1 except that the following Comparative Compound 2 was used instead of Compound 1 of the present disclosure. Coating Composition 9 was spin coated to form a coating layer, and the film was baked at 250° C. or lower.

Experimental Example 1-2

Experiments on Film Retention Rate of Coating Layer

In order to check the film retention rate of the coating layer formed using each of Coating Compositions 4, 8 and 9, a toluene solvent was spin treated on the top of the film, and the result was washed.

Specifically, Coating Composition 4 was spin coated for 60 seconds at a spin rate of 1000 rpm, and then baked through heating for 30 minutes on a hot plate at 230° C. to form a thin film. The result was immersed for 10 minutes in toluene, taken out, and the film retention rate was measured using UV-Visible spectroscopy and shown in FIG. 6.

FIG. 6 shows film retention rate data of Coating Composition 4.

The film retention rate was measured in the same manner except that Coating Composition 8 was used instead of Coating Composition 4, and shown in FIG. 7. FIG. 7 shows film retention rate data of Coating Composition 8.

The film retention rate was measured in the same manner except that Coating Composition 9 was used instead of Coating Composition 4, and shown in FIG. 8. FIG. 8 shows film retention rate data of Coating Composition 9.

The film retention rate data were obtained by comparing the degree of ultraviolet absorbance before and after the process of forming the film described above.

Through the above-mentioned results, it was seen that the result of FIG. 6 and the film retention rate data of FIG. 7 and FIG. 8 had a difference in the absorbance, and it means having a difference in the film-forming effect due to the difference in the absorbance. Accordingly, it was identified that Coating Composition 4 had increased chemical resistance and film retention rate compared to Coating Compositions 8 and 9.

[Compound 1]
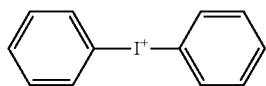 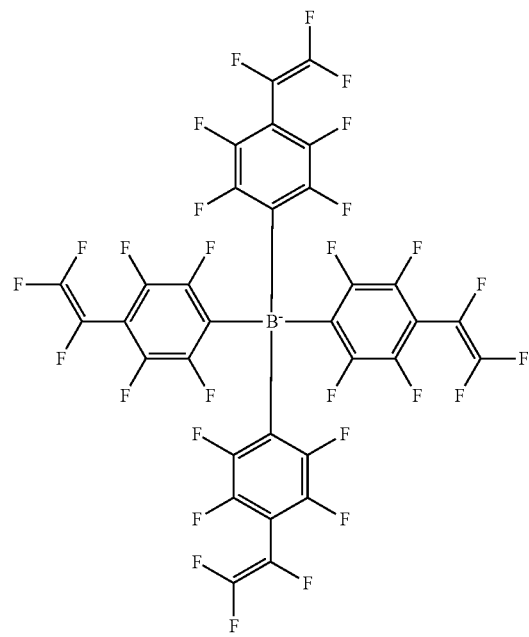
[Compound 2]
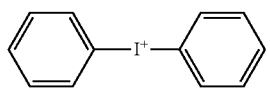
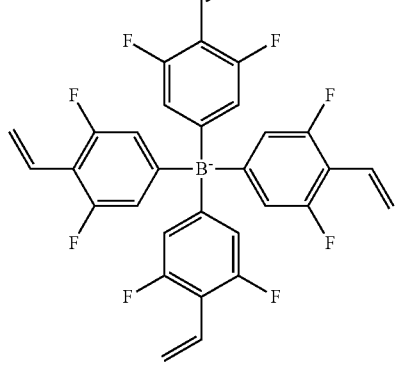
[Compound 3]
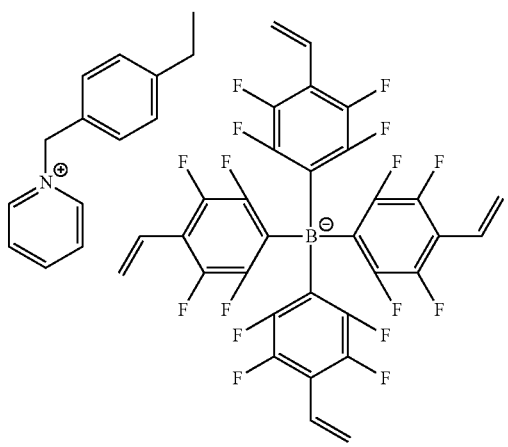
[Compound 4]
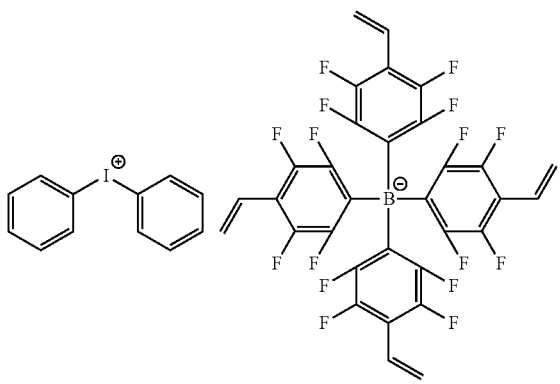
[Compound 7]
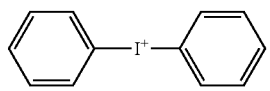
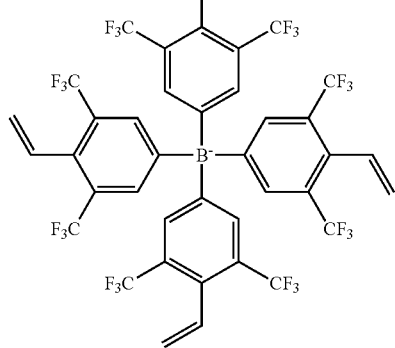

[Comparative Compound 1] 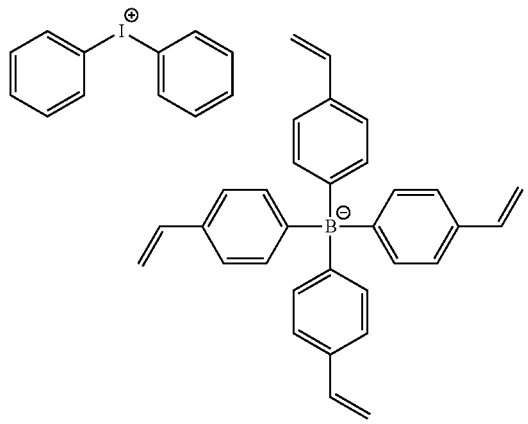

[Comparative Compound 2] 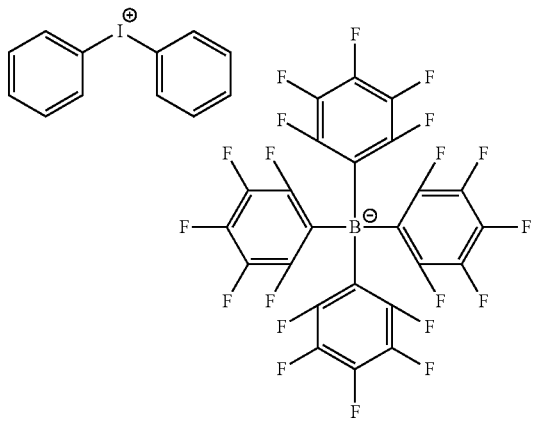

[Compound A]

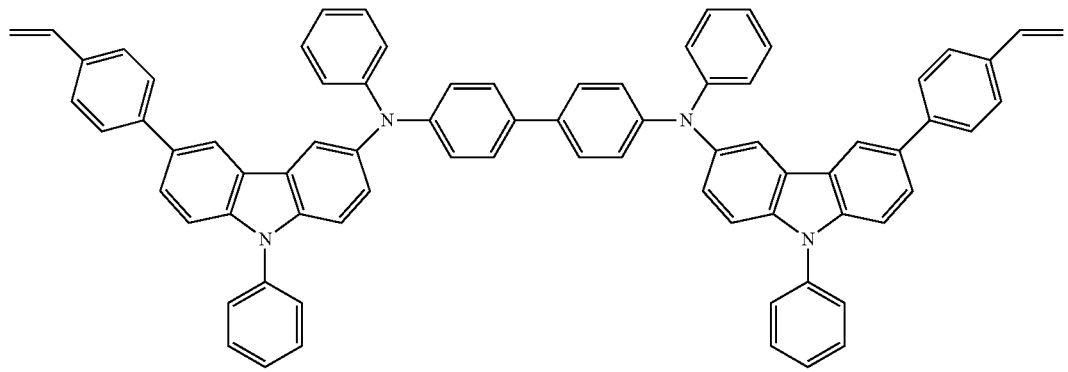

[Compound B] 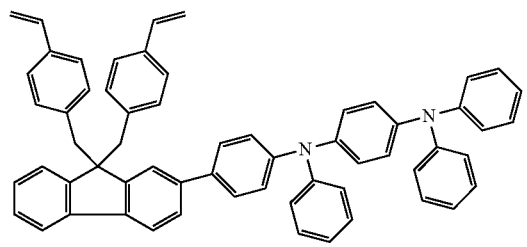

[Compound C] 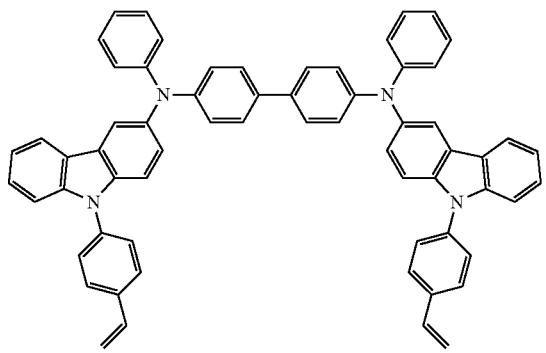

TABLE 1

| Coating Composition | Host | p-Doping Material | Spin Rate (rpm)/Time (s) | Baking Temperature (° C.)/Time (min) |
|---|---|---|---|---|
| 1 | Compound A | Compound 1 | 1000/60 | 230/30 |
| 2 | Compound A | Compound 2 | 1000/60 | 230/30 |
| 3 | Compound A | Compound 3 | 1000/60 | 230/30 |
| 4 | Compound A | Compound 4 | 1000/60 | 230/30 |
| 5 | Compound B | Compound 4 | 1000/60 | 230/30 |
| 6 | Compound C | Compound 4 | 1000/60 | 230/30 |
| 7 | Compound A | Compound 7 | 1000/60 | 230/30 |
| 8 | Compound A | Comparative Compound 1 | 1000/60 | 230/30 |
| 9 | Compound A | Comparative Compound 2 | 1000/60 | 230/30 |

Example 1

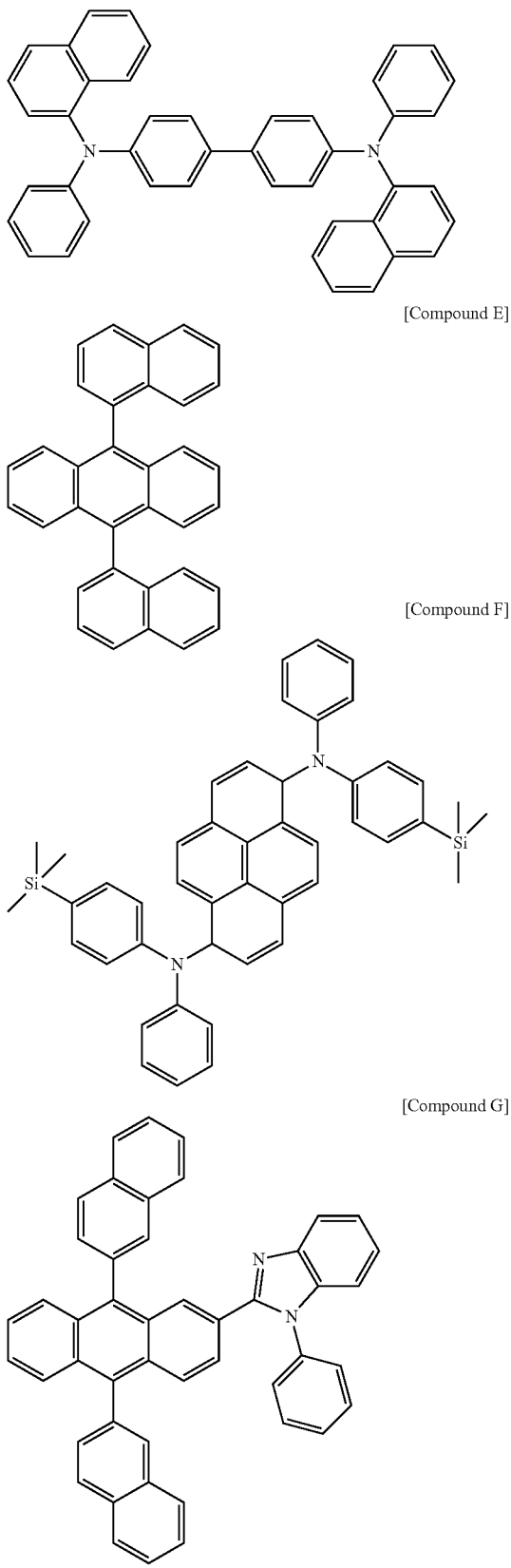

[Compound D]

[Compound E]

[Compound F]

[Compound G]

A glass substrate on which indium tin oxide (ITO) was deposited as a thin film to a thickness of 1,500 Å was placed in detergent-dissolved distilled water and ultrasonic cleaned. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone for 30 minutes each, dried, and then transferred to a glove box.

On the transparent ITO electrode prepared as above, Coating Composition 1 described in the table was spin coated to form a hole injection layer having a thickness of 300 Å, and the coating composition was cured for 30 minutes on a hot plate under $N_2$ atmosphere. After that, the result was transferred to a vacuum depositor, and then Compound D was vacuum deposited on the hole injection layer to form a hole transfer layer.

Subsequently, a light emitting layer was formed on the hole transfer layer by vacuum depositing Compound F in a concentration of 8% with respect to Compound E to a thickness of 300 Å. On the light emitting layer, Compound G was vacuum deposited to a thickness of 200 Å to form an electron injection and transfer layer. A cathode was formed on the electron injection and transfer layer by depositing LiF to a thickness of 12 Å and aluminum to a thickness of 2,000 Å in consecutive order.

In the above-mentioned processes, the deposition rates of the organic materials were maintained at 0.4 Å/sec to 0.7 Å/sec, the deposition rates of the LiF and the aluminum of the cathode were maintained at 0.3 Å/sec and 2 Å/sec, respectively, and the degree of vacuum during the deposition was maintained at $2\times10^{-7}$ to $5\times10^{-8}$ torr.

Example 2

An organic light emitting device was manufactured in the same manner as in Example 1 except that Coating Composition 2 was used instead of Coating Composition 1 as the hole injection layer.

Example 3

An organic light emitting device was manufactured in the same manner as in Example 1 except that Coating Composition 3 was used instead of Coating Composition 1 as the hole injection layer.

Example 4

An organic light emitting device was manufactured in the same manner as in Example 1 except that Coating Composition 4 was used instead of Coating Composition 1 as the hole injection layer.

Example 5

An organic light emitting device was manufactured in the same manner as in Example 1 except that Coating Composition 5 was used instead of Coating Composition 1 as the hole injection layer.

Example 6

An organic light emitting device was manufactured in the same manner as in Example 1 except that Coating Composition 6 was used instead of Coating Composition 1 as the hole injection layer.

Example 7

An organic light emitting device was manufactured in the same manner as in Example 1 except that Coating Composition 7 was used instead of Coating Composition 1 as the hole injection layer.

Comparative Example 1

An organic light emitting device was manufactured in the same manner as in Example 1 except that Coating Composition 8 was used instead of Coating Composition 1 as the hole injection layer.

Comparative Example 2

An organic light emitting device was manufactured in the same manner as in Example 1 except that Coating Composition 9 was used instead of Coating Composition 1 as the hole injection layer.

Results of measuring driving voltage and light emission efficiency for the organic light emitting devices manufactured using the above-described method at current density of 10 mA/cm² are shown in the following Table 2.

TABLE 2

| Example | Driving Voltage (V) | Current Efficiency (cd/A) | Power Efficiency (lm/W) | Lifetime (95%, h) |
|---|---|---|---|---|
| Example 1 | 5.20 | 7.02 | 4.24 | 37 |
| Example 2 | 3.60 | 6.40 | 5.58 | 41 |
| Example 3 | 5.80 | 7.70 | 4.17 | 80 |
| Example 4 | 4.70 | 7.69 | 5.14 | 39 |
| Example 5 | 4.80 | 7.74 | 5.06 | 40 |
| Example 6 | 4.40 | 7.34 | 5.24 | 43 |
| Example 7 | 4.20 | 6.77 | 5.06 | 32 |
| Comparative Example 1 | 9.70 | 11.96 | 3.87 | 1 |
| Comparative Example 2 | 4.30 | 6.60 | 4.82 | 20 |

Based on the results of Table 2, it was identified that the dopant having the structure of Chemical Formula 1 of the present specification had superior solubility for an organic solvent compared to generally-used dopants, and was thereby suited for solution processes, and, since a coating composition was readily prepared, a uniform coating layer may be formed using the coating composition. In addition, unlike existing dopants, a curing group was present preventing a lifetime decrease caused by interlayer inflow, and therefore, the dopant was able to be used in an organic light emitting device.

The invention claimed is:

1. An ionic compound comprising an anion group represented by the following Chemical Formula 1:

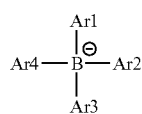

[Chemical Formula 1]

wherein, in Chemical Formula 1,
Ar1 to Ar4 are the same as or different from each other,
at least one of Ar1 to Ar4 is represented by the following Chemical Formula 2, and the remaining Ar1 to Ar4 if present are represented by the following Chemical Formula 3,

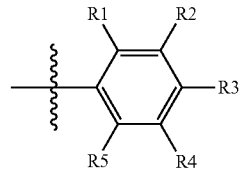

[Chemical Formula 2]

in Chemical Formula 2, at least one of R1 to R5 is F, a cyano group, or a substituted or unsubstituted fluoroalkyl group;
at least one of the remaining R1 to R5 is a curing group;
the remaining R1 to R5 if present are the same as or different from each other, and each independently hydrogen; deuterium; a nitro group; —C(O)R$_{100}$; —OR$_{101}$; —SR$_{102}$; —SO$_3$R$_{103}$; —COOR$_{104}$; —OC(O)R$_{105}$; —C(O)NR$_{106}$R$_{107}$; a substituted or unsubstituted alkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group;
R$_{100}$ to R$_{107}$ are the same as or different from each other, and each independently hydrogen; deuterium; or a substituted or unsubstituted alkyl group,

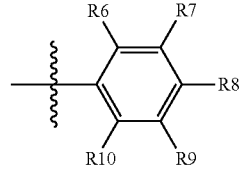

[Chemical Formula 3]

in Chemical Formula 3, at least one of R6 to R10 is a curing group;
the remaining R6 to R10 if present are the same as or different from each other, and each independently hydrogen; deuterium; a nitro group; —C(O)R$_{100}$; —OR$_{101}$; —SR$_{102}$; —SO$_3$R$_{103}$; —COOR$_{104}$; —OC(O)R$_{105}$; —C(O)NR$_{106}$R$_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group; and
R$_{100}$ to R$_{107}$ are the same as or different from each other, and each independently hydrogen; deuterium; or a substituted or unsubstituted alkyl group,
wherein the curing group is selected from the group consisting of the following curing groups:

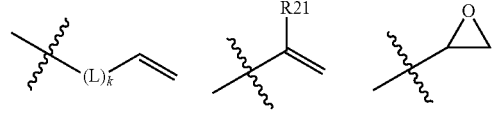

-continued

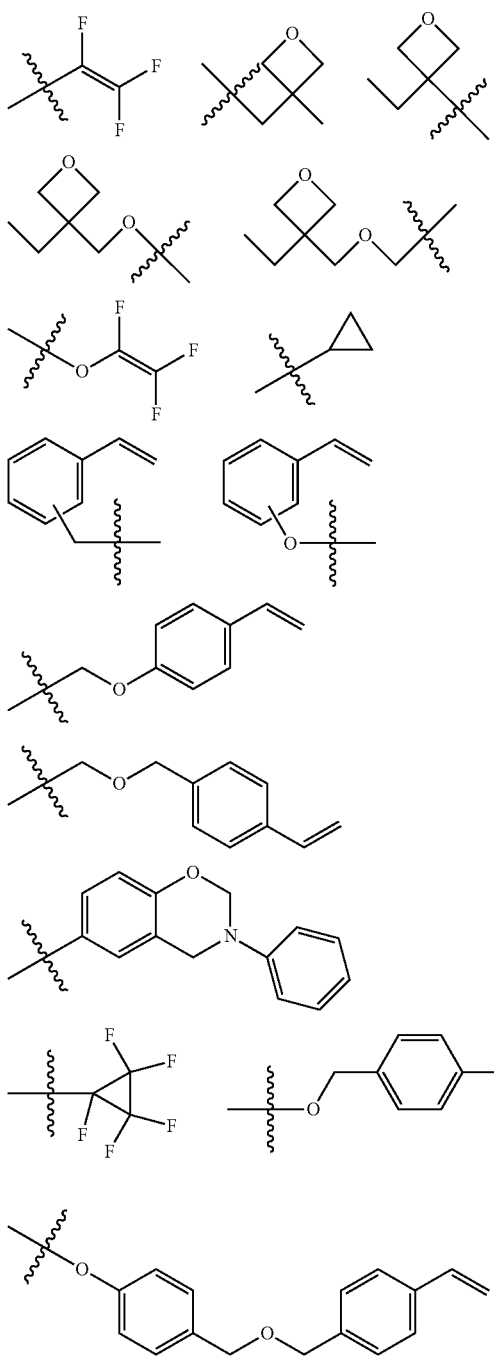

wherein, L is a direct bond; O; S; a substituted or unsubstituted alkylene group; a substituted or unsubstituted arylene group; or a substituted or unsubstituted divalent heterocyclic group, provided that the arylene group is not a phenyl group, k is an integer of 1 or 2, and when k is 2, the Ls are the same as or different from each other; and R21 is a substituted or unsubstituted alkyl group.

2. The ionic compound of claim 1, wherein Chemical Formula 2 is represented by any one of the following Chemical Formulae 2-1 to 2-10:

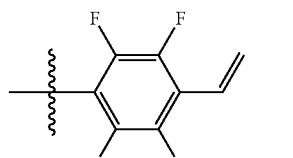
[Chemical Formula 2-1]

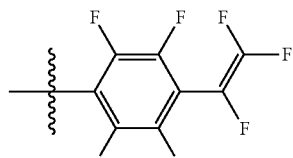
[Chemical Formula 2-2]

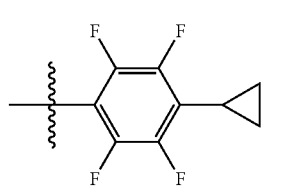
[Chemical Formula 2-3]

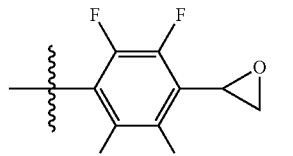
[Chemical Formula 2-4]

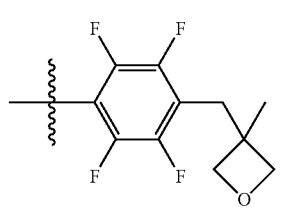
[Chemical Formula 2-5]

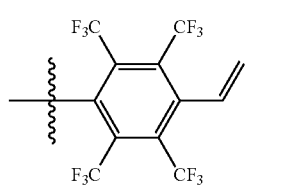
[Chemical Formula 2-6]

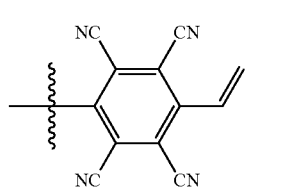
[Chemical Formula 2-7]

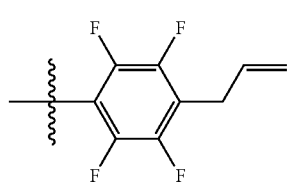
[Chemical Formula 2-8]

-continued

[Chemical Formula 2-9]

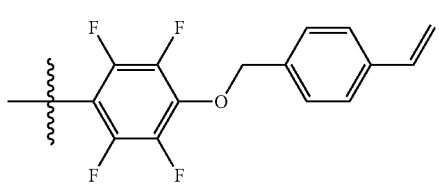

[Chemical Formula 2-10]

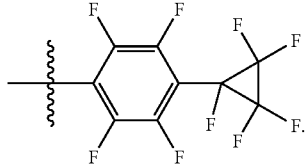

3. The ionic compound of claim 1, wherein Chemical Formula 3 is represented by any one of the following Chemical Formulae 3-1 to 3-8:

[Chemical Formula 3-1]

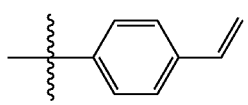

[Chemical Formula 3-2]

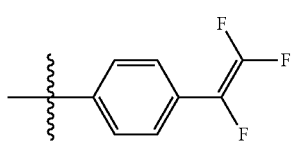

[Chemical Formula 3-3]

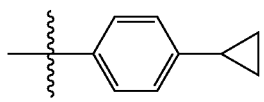

-continued

[Chemical Formula 3-4]

[Chemical Formula 3-5]

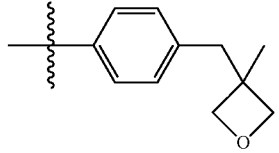

[Chemical Formula 3-6]

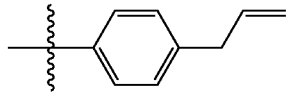

[Chemical Formula 3-7]

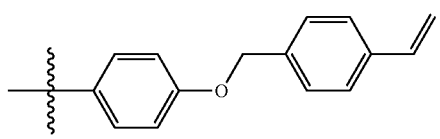

[Chemical Formula 3-8]

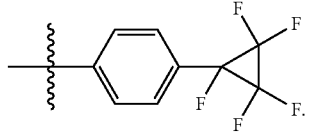

4. The ionic compound of claim 1, wherein the anion group of Chemical Formula 1 is any one selected from among the following structural formulae:

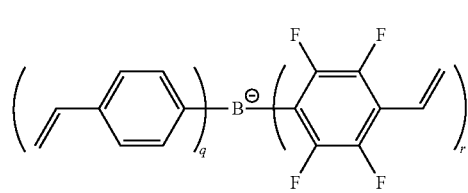

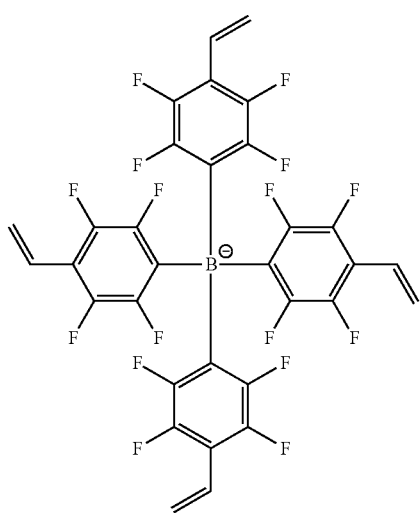

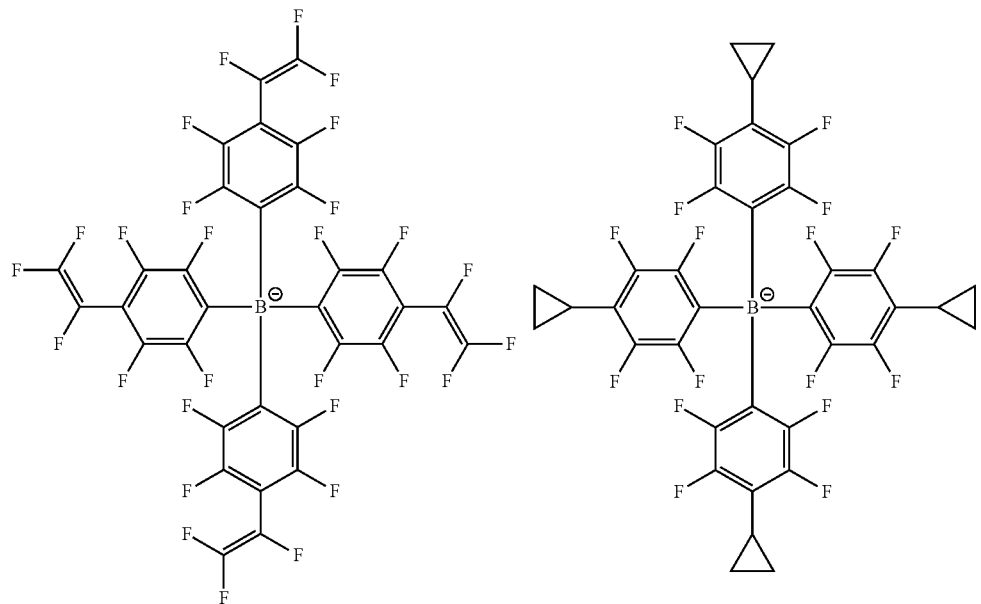
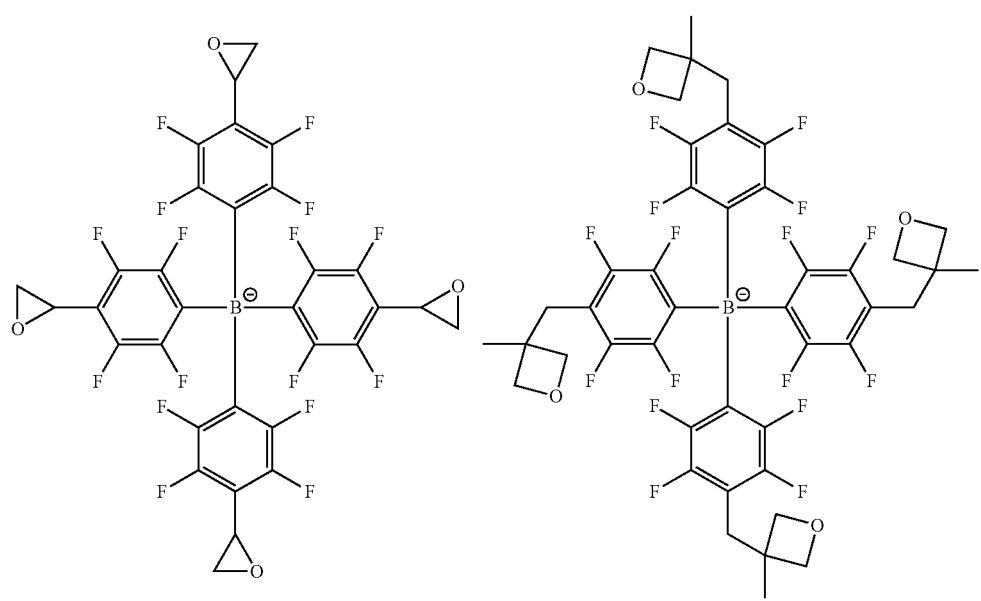

-continued
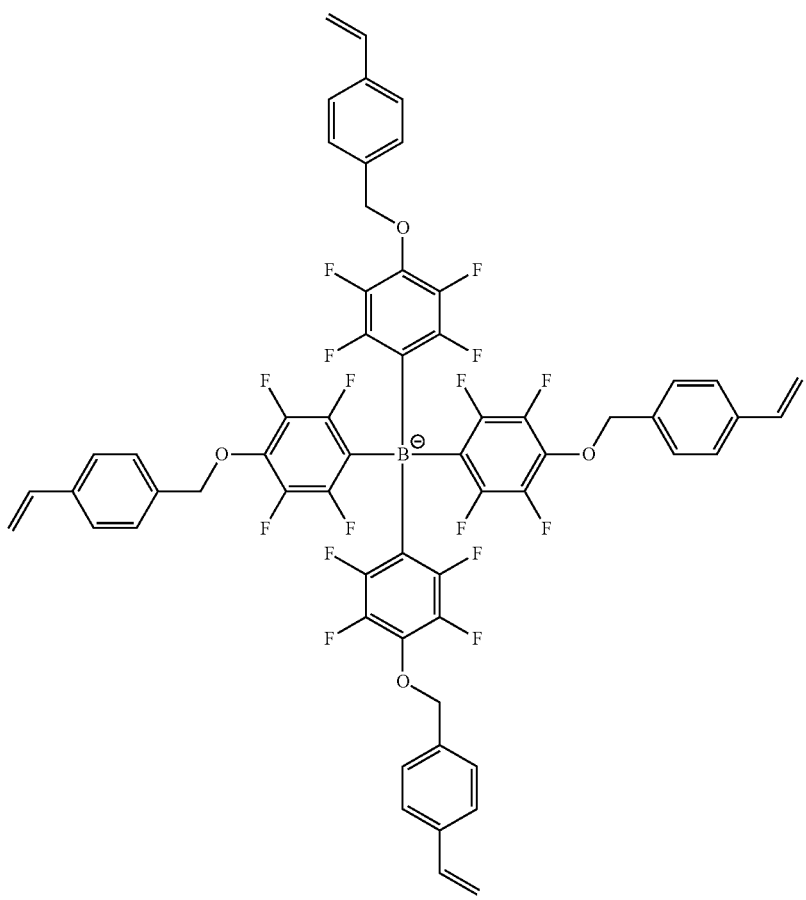
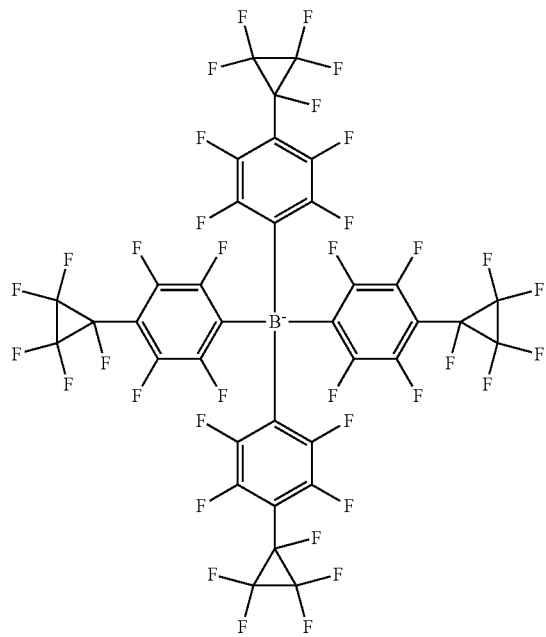
in the structural formulae, r is an integer of 1 to 4, q is an integer of 0 to 3, and q+r=4.

5. The ionic compound of claim 1, further comprising a cation group, wherein the cation group is selected from among monovalent cation groups, onium compounds or the following structural formulae:

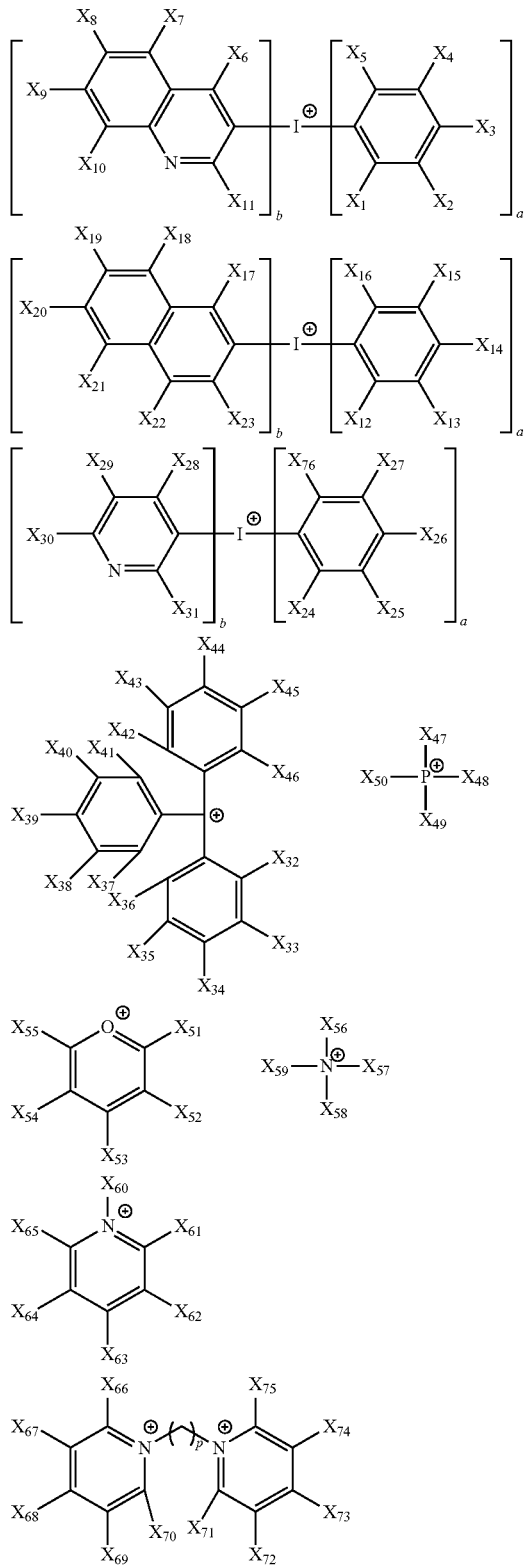

in the structural formulae, $X_1$ to $X_{75}$ are the same as or different from each other, and each independently hydrogen; a cyano group; a nitro group; a halogen group; $-COOR_{104}$; a substituted or unsubstituted alkyl group; a substituted or unsubstituted alkoxy group; a substituted or unsubstituted cycloalkyl group; a substituted or unsubstituted fluoroalkyl group; or a substituted or unsubstituted aryl group, or a curing group;

$R_{104}$ is hydrogen; deuterium; a substituted or unsubstituted alkyl group;

p is an integer of 0 to 10; and a is 1 or 2, b is 0 or 1, and a+b=2.

6. The ionic compound of claim 5, wherein the cation group is represented by any one of the following Chemical Formula 10 to Chemical Formula 15:

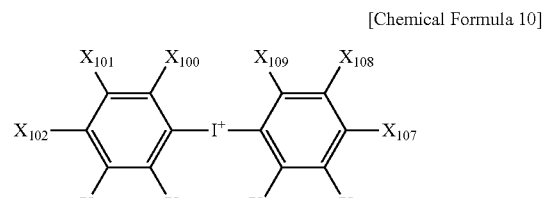

[Chemical Formula 10]

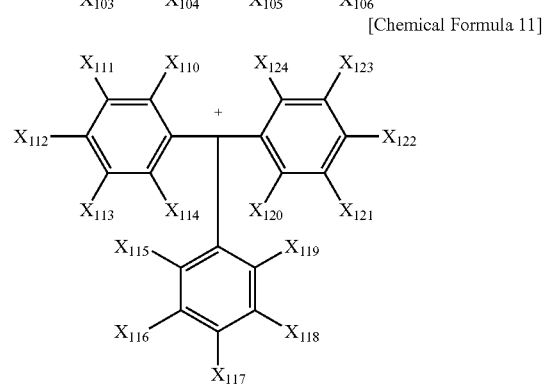

[Chemical Formula 11]

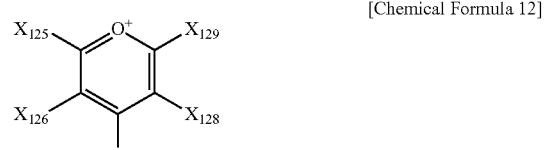

[Chemical Formula 12]

[Chemical Formula 13]

[Chemical Formula 14]

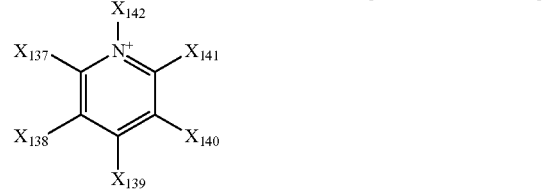

[Chemical Formula 15]

$X_{47}$ to $X_{50}$, $X_{100}$ to $X_{129}$ and $X_{133}$ to $X_{142}$ are the same as or different from each other, and each independently hydrogen; a cyano group; a nitro group; a halogen group; —COOR$_{104}$; a substituted or unsubstituted alkyl group; a substituted or unsubstituted alkoxy group; a substituted or unsubstituted cycloalkyl group; a substituted or unsubstituted fluoroalkyl group; or a substituted or unsubstituted aryl group, or a curing group; and R$_{104}$ is a substituted or unsubstituted alkyl group.

7. The ionic compound of claim 5, wherein the cation group is any one selected from among the following structural formulae:

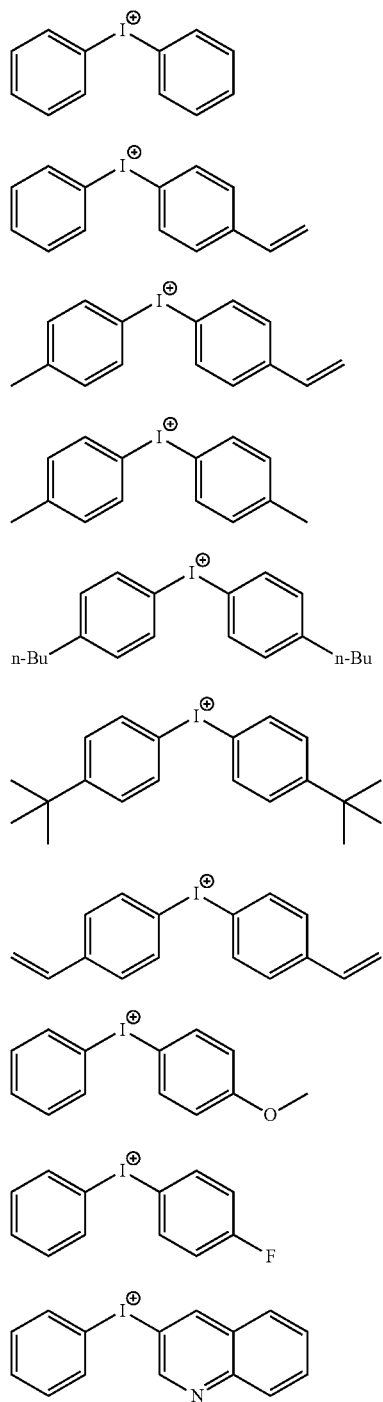

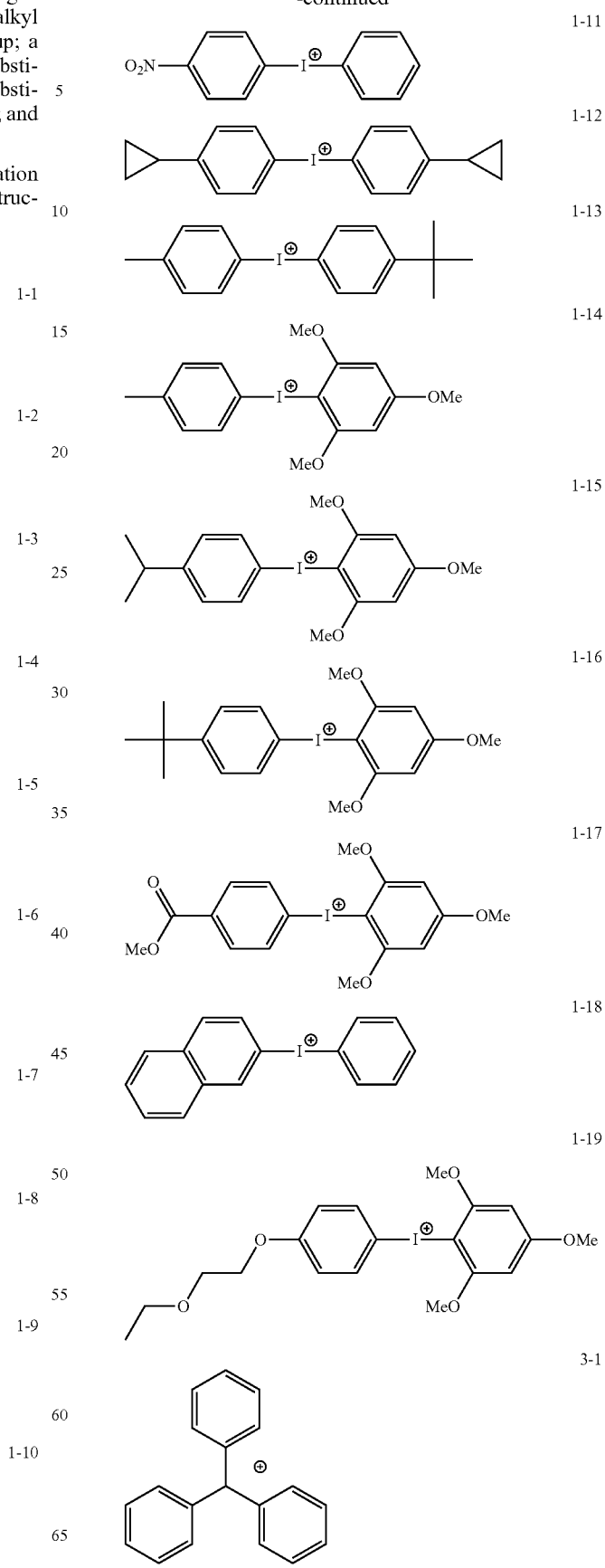

-continued
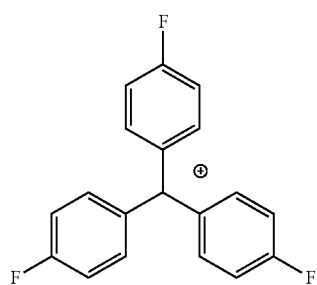 [SMILES: Fc1ccc(C(c2ccc(F)cc2)c2ccc(F)cc2)cc1]
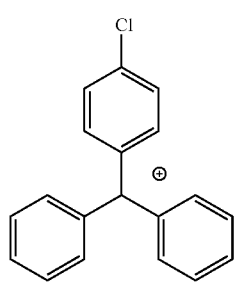 [SMILES: Clc1ccc(C(c2ccccc2)c2ccccc2)cc1]
4-1
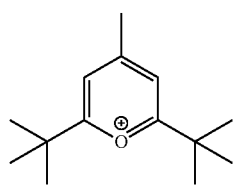
4-2
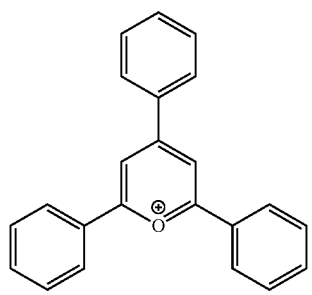 [SMILES: c1ccc(-c2cc(-c3ccccc3)[o+]c(-c3ccccc3)c2)cc1]
4-3
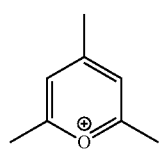
5-1
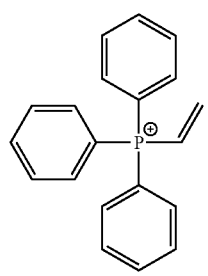 [SMILES: C=C[P+](c1ccccc1)(c1ccccc1)c1ccccc1]
-continued
3-2
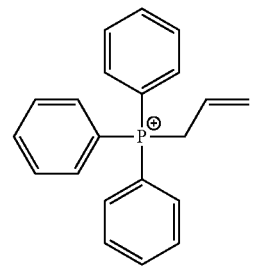 [SMILES: C=CC[P+](c1ccccc1)(c1ccccc1)c1ccccc1]
3-3
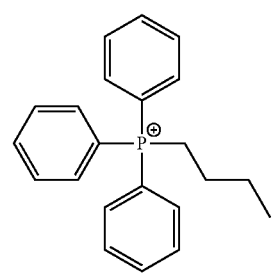 [SMILES: CCCC[P+](c1ccccc1)(c1ccccc1)c1ccccc1]
4-1
4-2
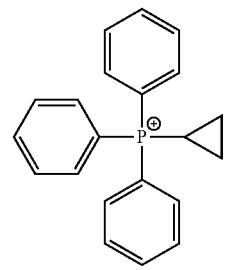 [SMILES: c1ccc([P+](c2ccccc2)(c2ccccc2)C2CC2)cc1]
5-5
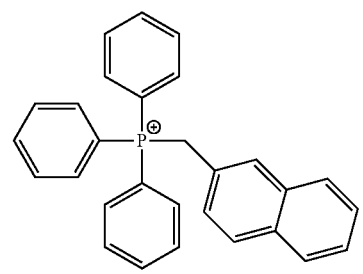 [SMILES: c1ccc([P+](Cc2ccc3ccccc3c2)(c2ccccc2)c2ccccc2)cc1]
5-6
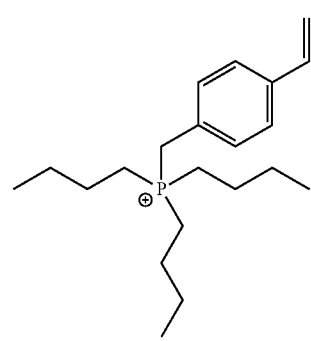 [SMILES: C=Cc1ccc(C[P+](CCCC)(CCCC)CCCC)cc1]

6-1
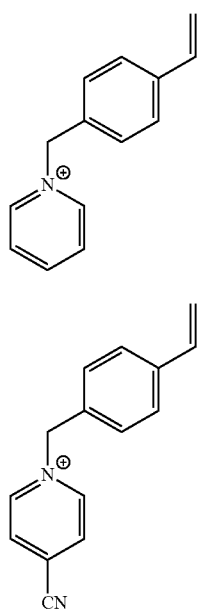
6-2
6-3
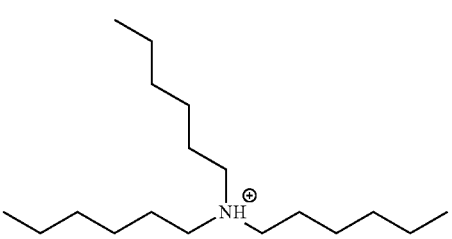 [SMILES: CCCCCC[NH+](CCCCCC)CCCCCC]
6-4
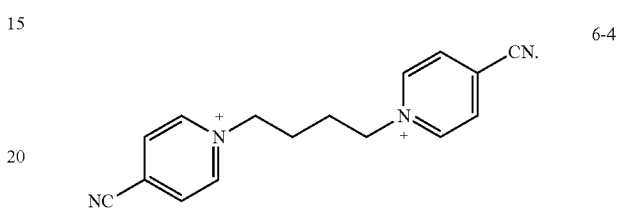
8. The ionic compound of claim 1, which is selected from among the following structural formulae:
[Chemical Formula 1-1-1]
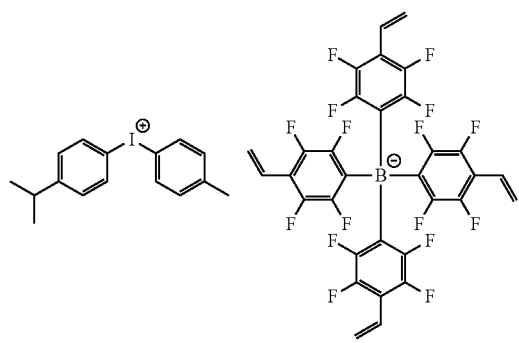
[Chemical Formula 1-1-2]
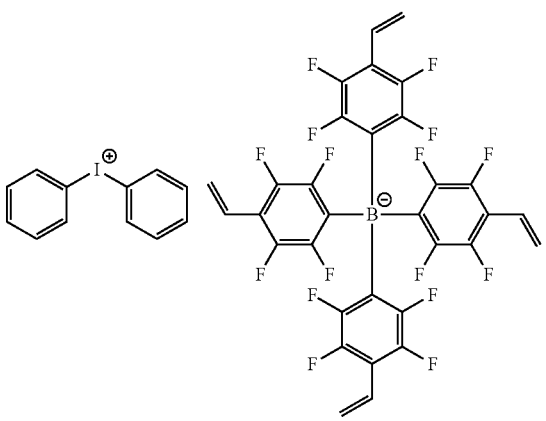
[Chemical Formula 1-1-3]
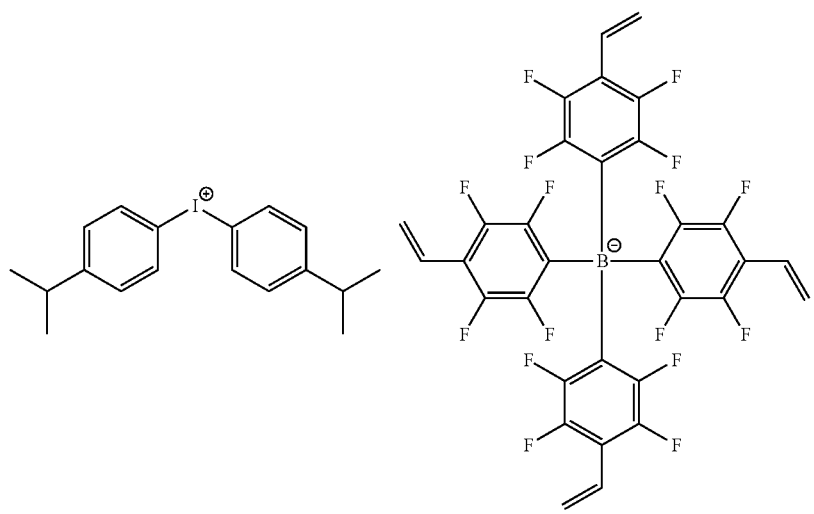

-continued
[Chemical Formula 1-1-4]
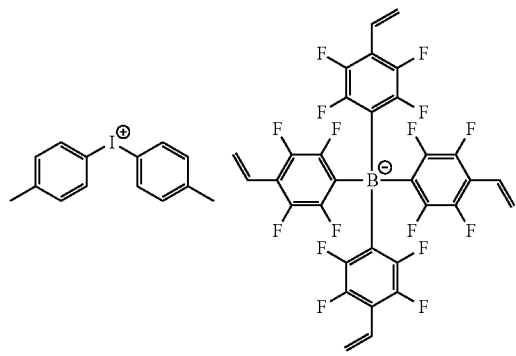
[Chemical Formula 1-1-5]
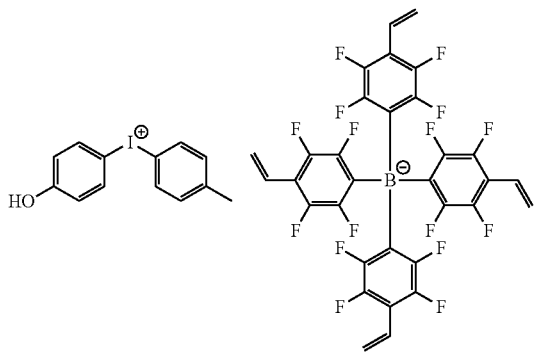
[Chemical Formula 1-1-6]
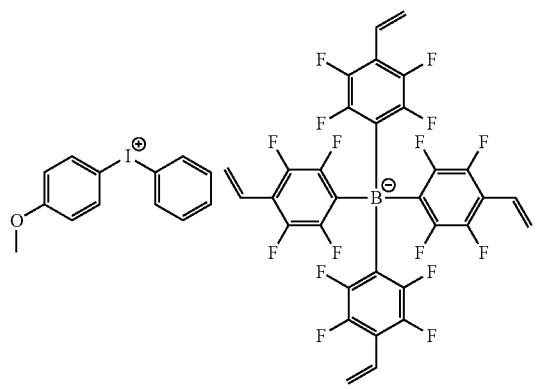
[Chemical Formula 1-1-7]
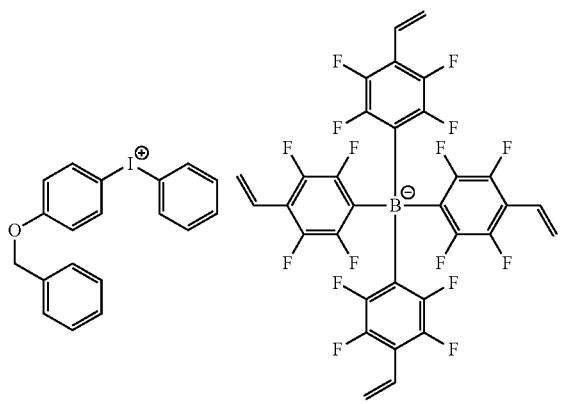
[Chemical Formula 1-1-8]
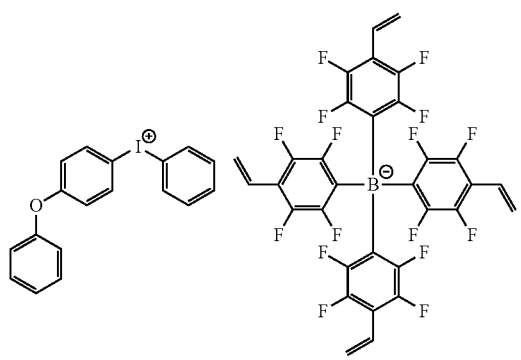
[Chemical Formula 1-1-9]
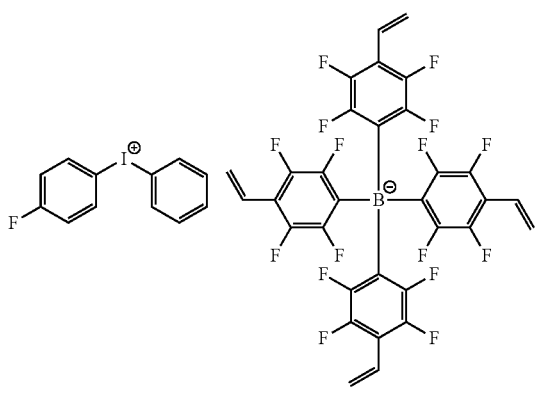
[Chemical Formula 1-1-10]
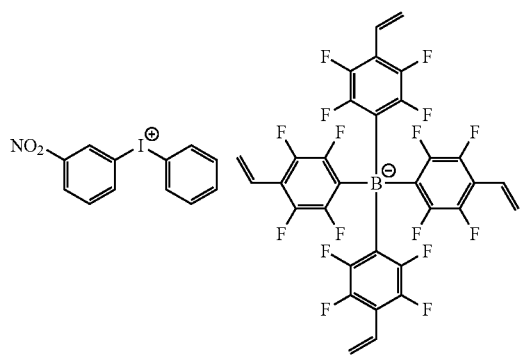
[Chemical Formula 1-1-11]
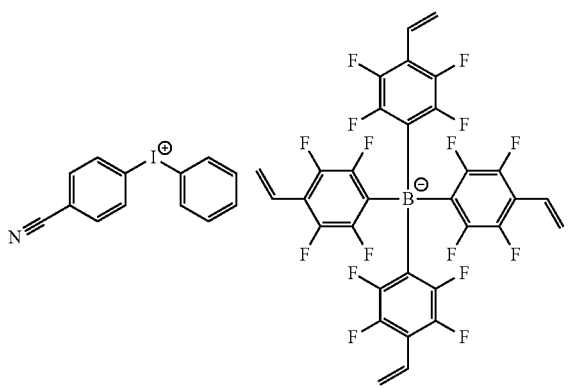

[Chemical Formula 1-1-12]
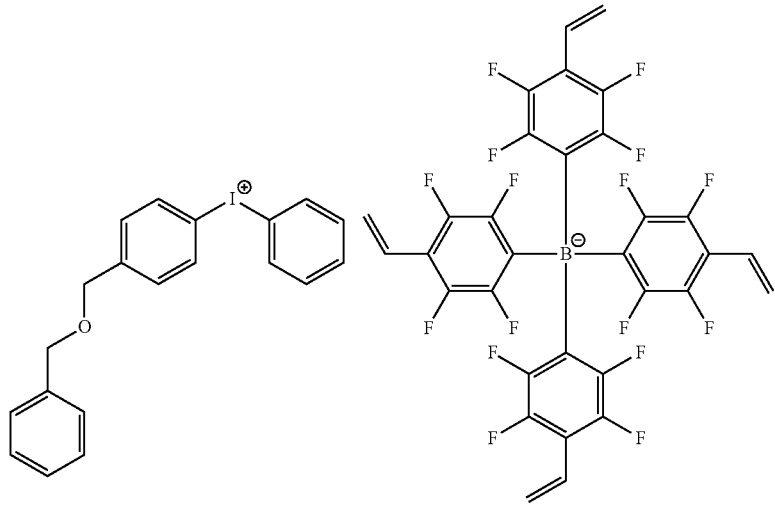
[Chemical Formula 1-1-13]
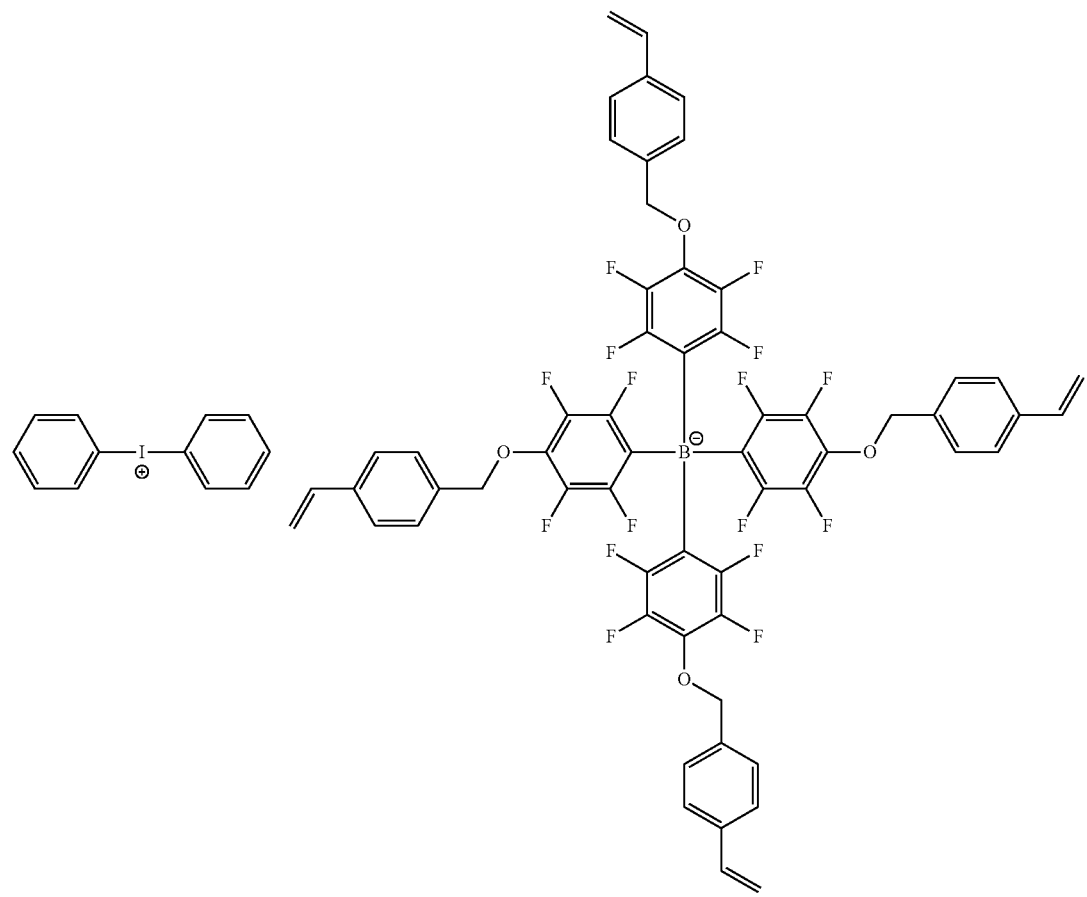

[Chemical Formula 1-1-14]
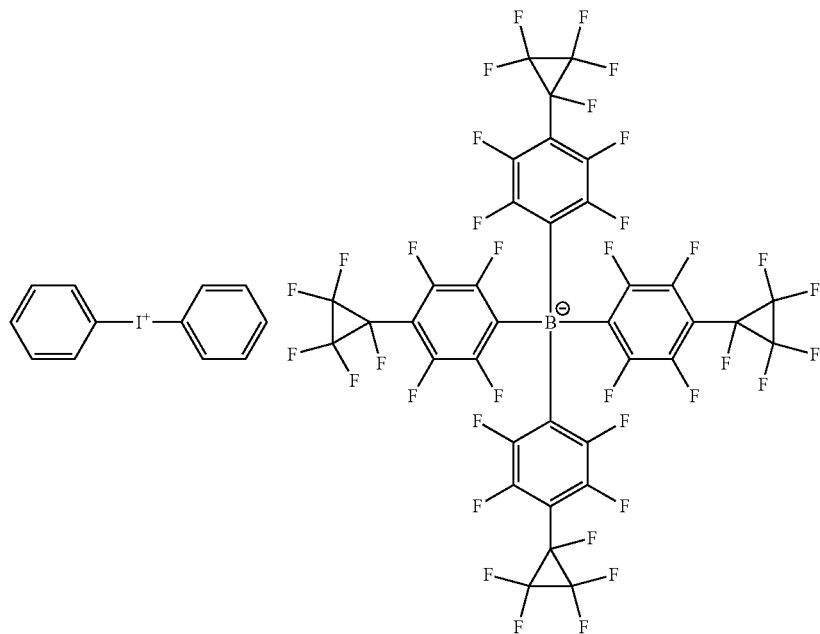
[Chemical Formula 1-1-15]
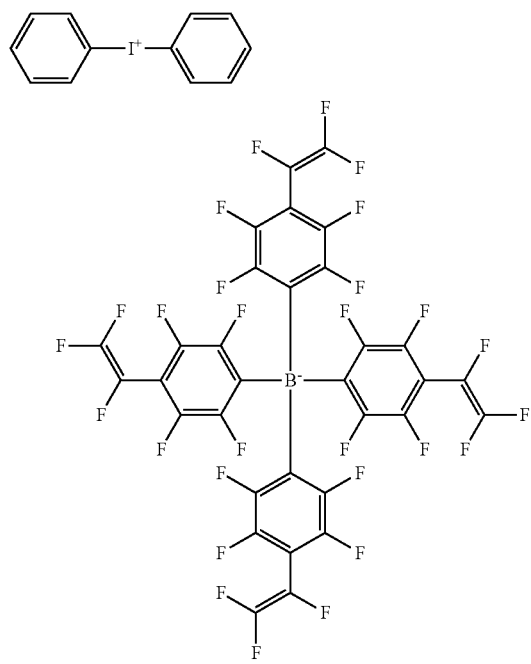
[Chemical Formula 1-1-16]
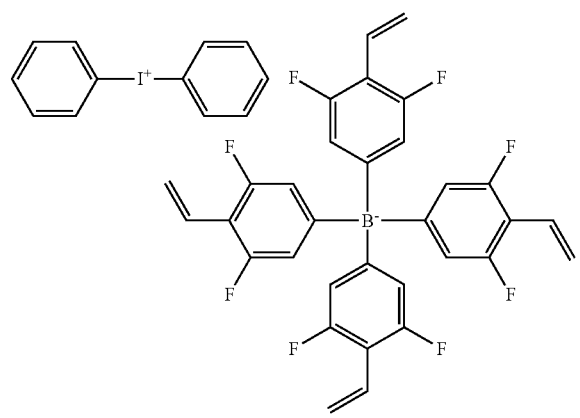

-continued
[Chemical Formula 1-1-17]
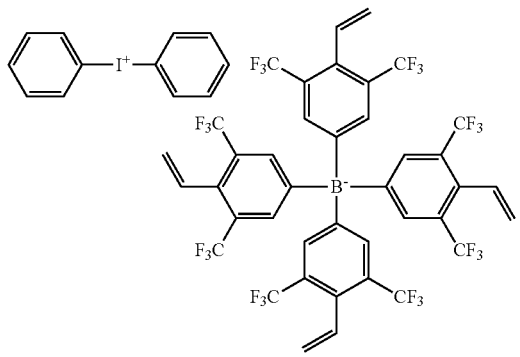
[Chemical Formula 1-1-18]
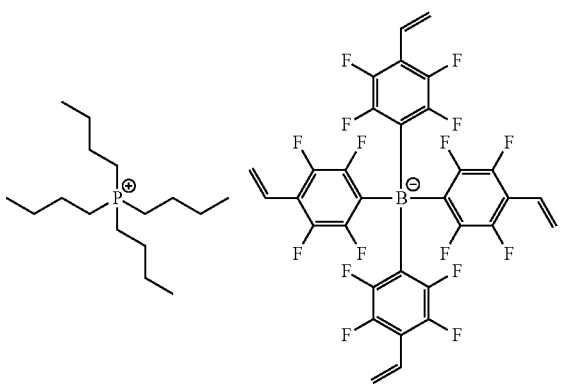
[Chemical Formula 1-1-19]
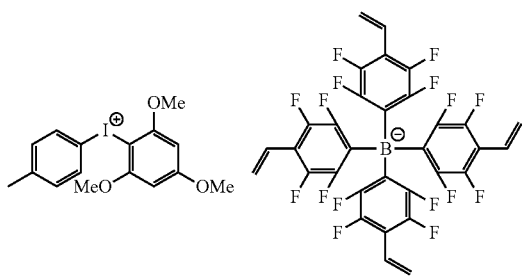
[Chemical Formula 1-2-1]
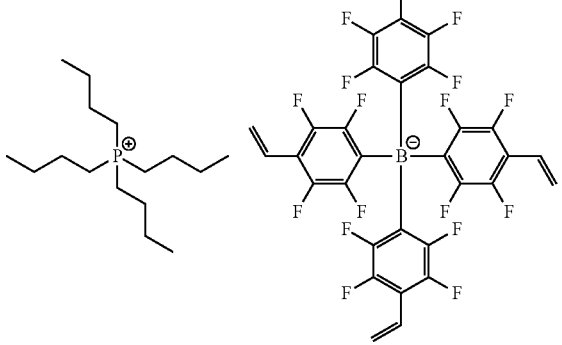
[Chemical Formula 1-2-2]
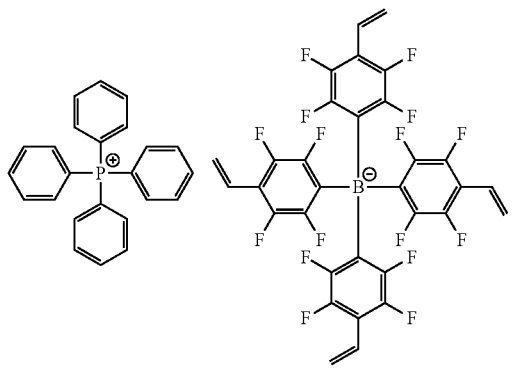
[Chemical Formula 1-2-3]
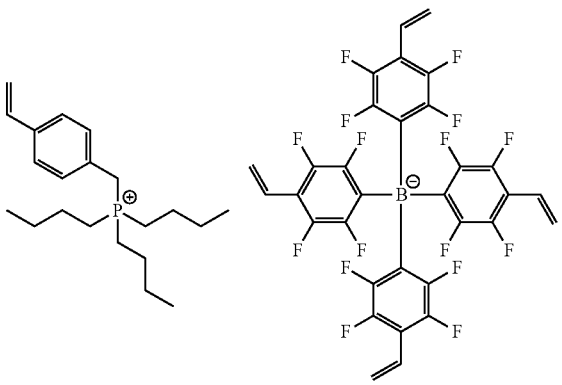
[Chemical Formula 1-2-4]
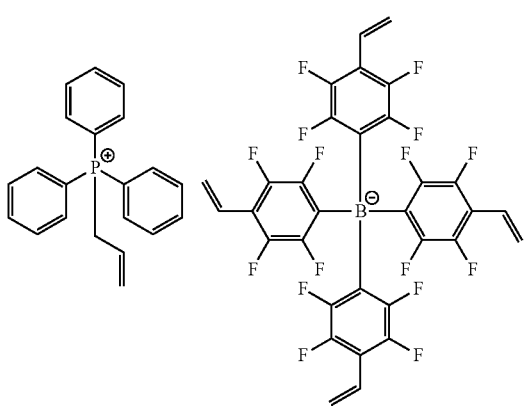
[Chemical Formula 1-2-5]
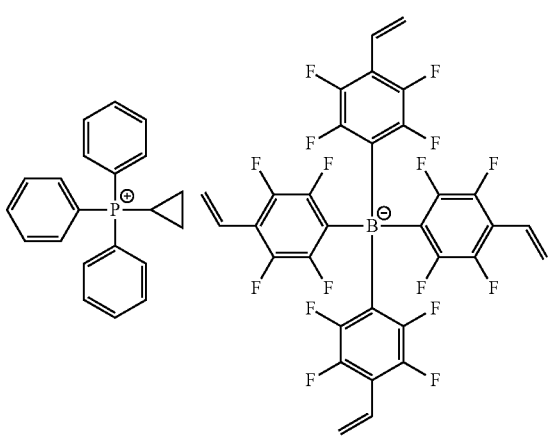

-continued

[Chemical Formula 1-3-1]

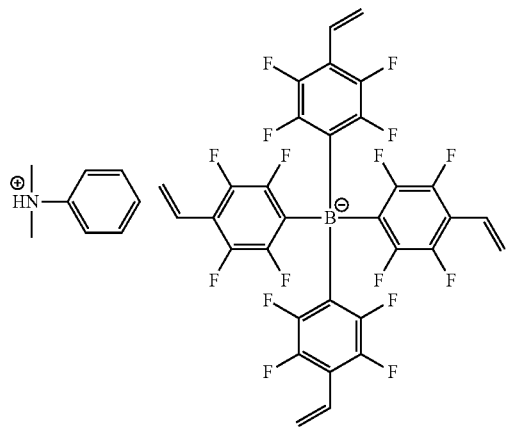

[Chemical Formula 1-3-2]

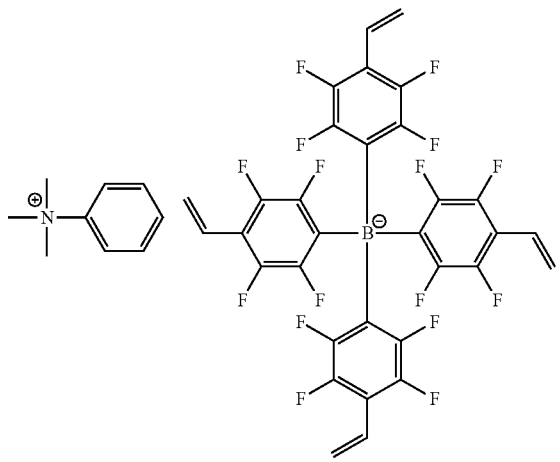

[Chemical Formula 1-3-3]

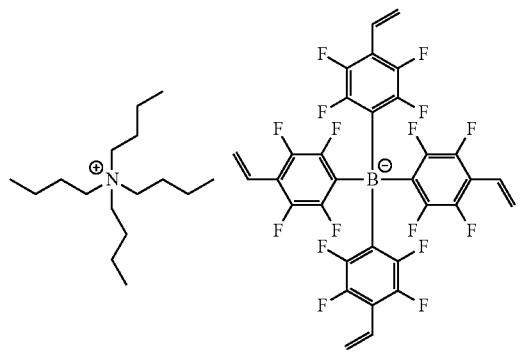

[Chemical Formula 1-3-4]

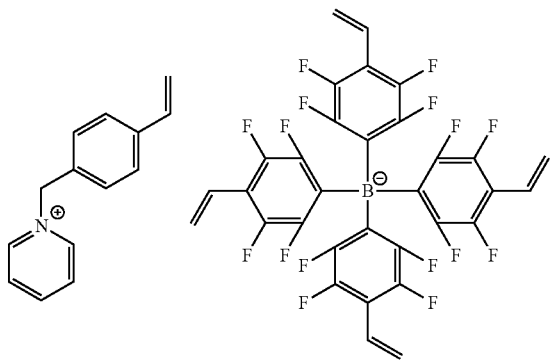

[Chemical Formula 1-4-1]

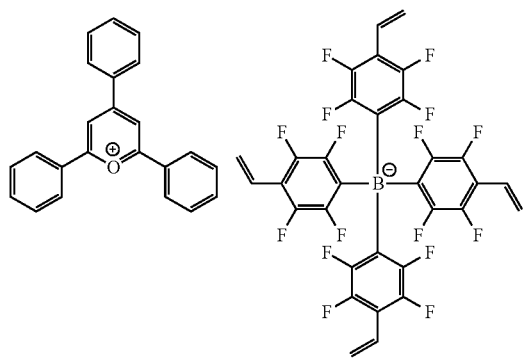

[Chemical Formula 1-5-1]

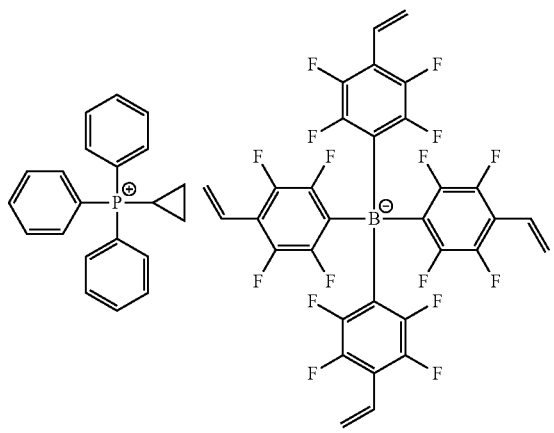

9. A coating composition comprising the ionic compound of claim 1.

10. The coating composition of claim 9, which is for an organic light emitting device.

11. The coating composition of claim 9, further comprising an arylamine compound that is a monomer or a polymer.

12. The coating composition of claim 11, wherein the arylamine compound includes at least one of the following-structured curing groups:

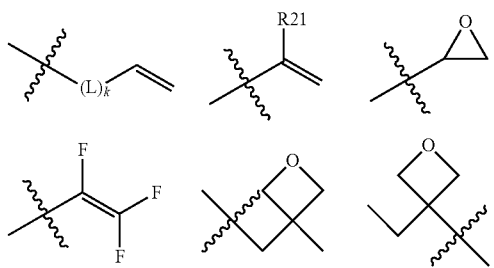

-continued

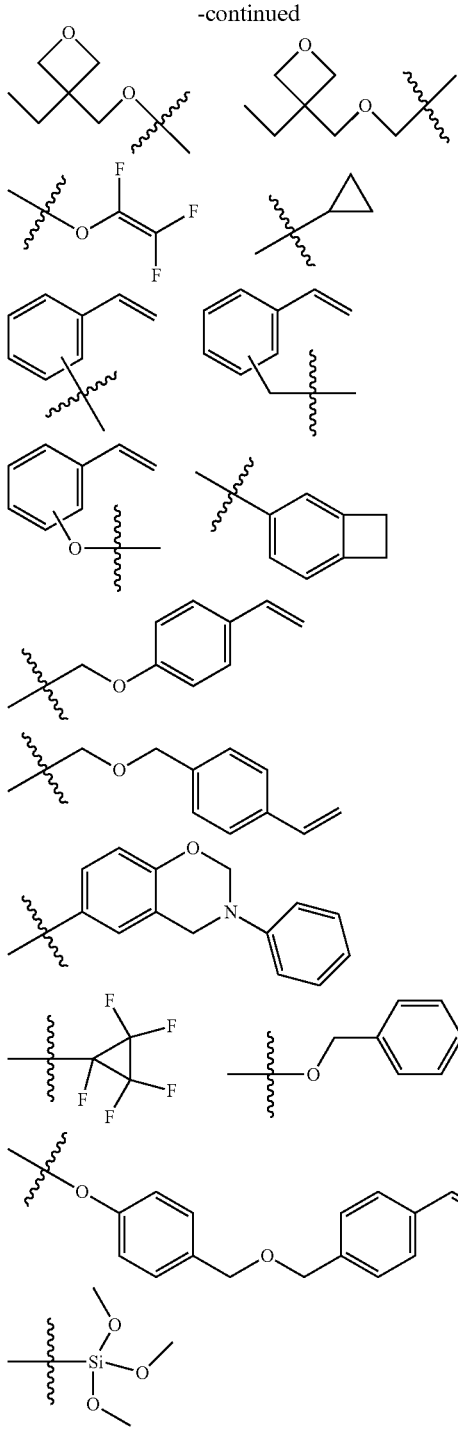

in the structural formulae, L is a direct bond; O; S; a substituted or unsubstituted alkylene group; a substituted or unsubstituted arylene group; or a substituted or unsubstituted divalent heterocyclic group; and k is an integer of 1 or 2, and when k is 2, the Ls are different from each other, and R21 is a substituted or unsubstituted alkyl group.

13. An organic light emitting device comprising:
a first electrode;
a second electrode provided opposite to the first electrode; and
one or more organic material layers provided between the first electrode and the second electrode,
wherein one or more layers of the organic material layers include a cured material of the coating composition of claim 9.

14. The organic light emitting device of claim 13, wherein the cured material of the coating composition is in a cured state by heat treating or light treating the coating composition.

15. The organic light emitting device of claim 13, wherein the organic material layer including the cured material of the coating composition is a hole transfer layer, a hole injection layer, or a layer carrying out hole transfer and hole injection at the same time.

16. The organic light emitting device of claim 13, wherein the organic material layer including the cured material of the coating composition is a hole transfer layer, and the ionic compound of the cured material of the coating composition is included as a p-doping material of the hole injection layer.

17. The organic light emitting device of claim 16, further comprising an arylamine compound that is a monomer or a polymer as a host of the hole injection layer.

18. The organic light emitting device of claim 17, wherein the arylamine compound includes at least one of the following-structured curing groups:

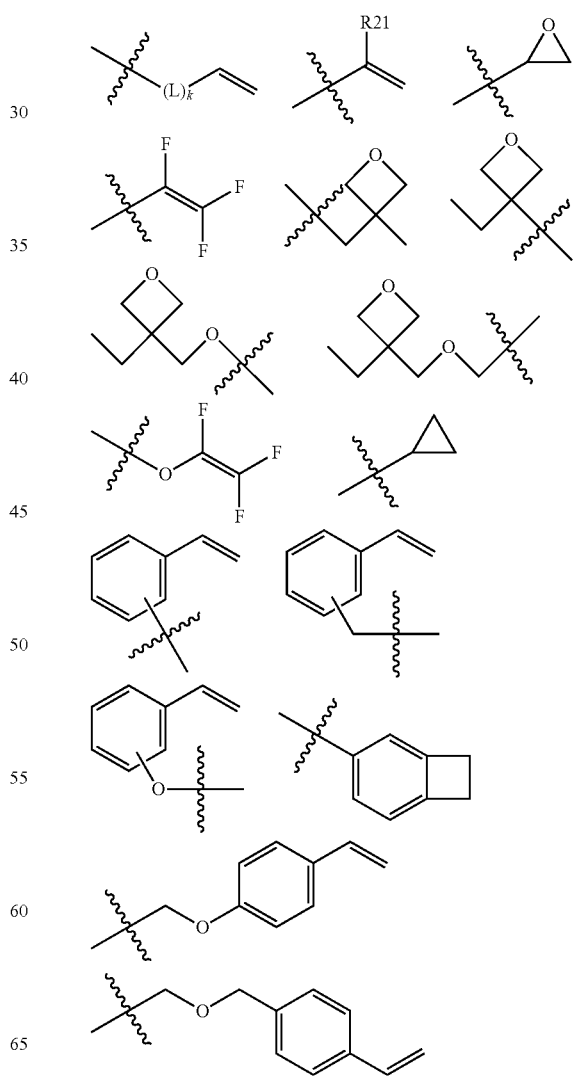

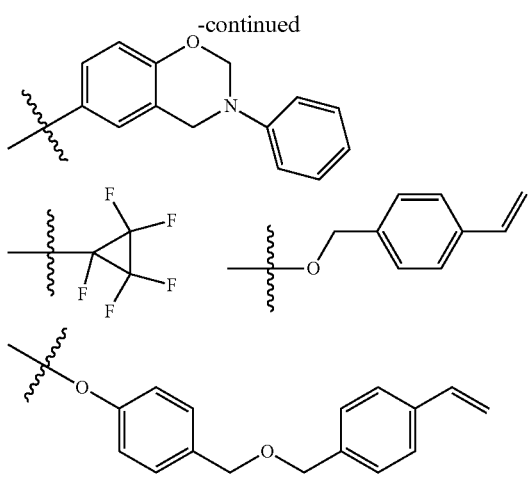
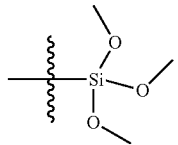 [SMILES: *[Si](OC)(OC)OC]

in the structural formulae, L is a direct bond; O; S; a substituted or unsubstituted alkylene group; a substituted or unsubstituted arylene group; or a substituted or unsubstituted divalent heterocyclic group; and k is an integer of 1 or 2, and when k is 2, the Ls are different from each other, and R21 is a substituted or unsubstituted alkyl group.

19. The organic light emitting device of claim 16, wherein a host of the hole injection layer is a compound having a HOMO level from 4.8 eV to 5.8 eV.

* * * * *